(12) United States Patent
Bury et al.

(10) Patent No.: US 9,994,529 B2
(45) Date of Patent: Jun. 12, 2018

(54) AMINO QUINAZOLINES AS KINASE INHIBITORS

(71) Applicant: GlaxoSmithKline Intellectual Property Development Limited, Brentford, Middlesex (GB)

(72) Inventors: Michael Jonathan Bury, Collegeville, PA (US); Linda N. Casillas, Collegeville, PA (US); Adam K. Charnley, Collegeville, PA (US); Michael P. Demartino, Collegeville, PA (US); Xiaoyang Dong, Collegeville, PA (US); Patrick M. Eidam, Collegeville, PA (US); Pamela A. Haile, Collegeville, PA (US); Robert W. Marquis, Jr., Collegeville, PA (US); Joshi M. Ramanjulu, Collegeville, PA (US); Joseph J. Romano, Collegeville, PA (US); Ami Lakdawala Shah, King of Prussia, PA (US); Robert R. Singhaus, Jr., Collegeville, PA (US); Gren Wang, Collegeville, PA (US)

(73) Assignee: GlaxoSmithKline Intellectual Property Development Limited (GB)

( * ) Notice: Subject to any disclaimer, the term of this patent is extended or adjusted under 35 U.S.C. 154(b) by 0 days. days.

(21) Appl. No.: 15/431,942

(22) Filed: Feb. 14, 2017

(65) Prior Publication Data
US 2017/0152233 A1    Jun. 1, 2017

Related U.S. Application Data

(63) Continuation of application No. 14/239,193, filed as application No. PCT/US2012/051247 on Aug. 17, 2012, now Pat. No. 9,604,938.

(60) Provisional application No. 61/524,925, filed on Aug. 18, 2011.

(51) Int. Cl.
| C07D 239/94 | (2006.01) |
| C07D 403/12 | (2006.01) |
| C07D 417/12 | (2006.01) |
| C07D 417/14 | (2006.01) |
| C07D 471/04 | (2006.01) |

(52) U.S. Cl.
CPC ......... *C07D 239/94* (2013.01); *C07D 403/12* (2013.01); *C07D 417/12* (2013.01); *C07D 417/14* (2013.01); *C07D 471/04* (2013.01)

(58) Field of Classification Search
CPC .................................................. C07D 239/94
See application file for complete search history.

(56) References Cited

U.S. PATENT DOCUMENTS

| 5,457,105 A | 10/1995 | Barker ...................... 514/234.5 |
| 5,576,322 A | 11/1996 | Takase et al. |
| 5,710,158 A | 1/1998 | Myers et al. |
| 5,747,498 A | 5/1998 | Schnur et al. |
| 5,801,180 A | 9/1998 | Takase et al. |
| 6,046,206 A | 4/2000 | Pamukcu et al. ............. 514/259 |
| 6,548,508 B2 | 4/2003 | Westbrook et al. |
| 6,589,758 B1 | 7/2003 | Zhu ................................ 435/15 |
| 6,743,799 B2 | 6/2004 | Westbrook et al. |
| 6,809,097 B1 | 10/2004 | Thomas et al. ............ 514/235.2 |
| 7,282,504 B2 | 10/2007 | Armistead et al. ........... 514/275 |
| 7,566,786 B2 | 7/2009 | Baldwin et al. |
| 7,569,577 B2 | 8/2009 | Hennequin et al. ..... 514/266.22 |
| 7,618,975 B2 | 11/2009 | Cai et al. ................... 514/262.1 |
| 7,709,479 B1 | 5/2010 | Mortlock et al. |
| 9,216,965 B2 | 12/2015 | Casillas et al. |
| 9,604,938 B2 * | 3/2017 | Bury .................... C07D 403/12 |
| 2002/0026052 A1 | 2/2002 | Boschelli et al. ............ 546/122 |
| 2003/0087919 A1 | 5/2003 | Nagarathnam et al. |
| 2003/0125344 A1 | 7/2003 | Nagarathnam et al. |
| 2003/0212276 A1 | 11/2003 | Boschelli et al. ............ 546/153 |
| 2003/0220357 A1 | 11/2003 | Bankston et al. |
| 2005/0070561 A1 | 3/2005 | Jung et al. |
| 2005/0267101 A1 | 12/2005 | Randle ......................... 514/221 |
| 2006/0116357 A1 | 6/2006 | Heron et al. |
| 2008/0032996 A1 | 2/2008 | Mitsuya et al. |
| 2008/0221132 A1 | 9/2008 | Cai et al. |

(Continued)

FOREIGN PATENT DOCUMENTS

| EP | 0 973 746 B1 | 9/2003 |
| EP | 2 072 502 A1 | 6/2009 |

(Continued)

OTHER PUBLICATIONS

Tigno-Aranjuez, *Genes & Development*, vol. 24, 2666-2677, 2010.
Amendment, U.S. Appl. No. 14/762,905, filed Jul. 23, 2015.
Amendment, U.S. Appl. No. 14/397,218, filed Nov. 17, 2015.
Amendment, U.S. Appl. No. 14/002,147, filed Dec. 4, 2015.
Amendment, U.S. Appl. No. 14/933,201, filed Nov. 19, 2015.
Amendment, U.S. Appl. No. 14/934,395, filed Nov. 19, 2015.
Arostegui, et al., *Arthritis & Rheumatism*, 56(11):3805-3813 (2007).
Biancheri, et al., *Digestive and Liver Disease, Abstract*, 45S:S71 (2013).
Body-Malapel, et al., *Laboratory Investigation*, 88:318-327 (2008).
Carreno, et al., *Acta Ophthalmologica, Abstract*, 2014.
Corridoni, et al., *PNAS*, 110(42):16999-17004 (2013).
Denou, et al., *EMBO Molecular Medicine*, 7(3):259-274 (2015).
Dharancy, et al., *Gastroenterology*, 138:1546-1556 (2010).
Du, et al., *Kidney International*, 84:265-276 (2013).
Ermann, et al., *PNAS*, E2559-E2566 (2014).

(Continued)

*Primary Examiner* — Paul V Ward
(74) *Attorney, Agent, or Firm* — Fang Qian

(57) ABSTRACT

Disclosed are compounds having the formula:

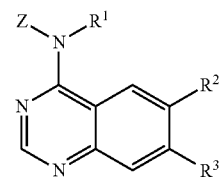

wherein $R^1$, $R^2$, $R^3$, and Z are as defined herein, and methods of making and using the same.

11 Claims, 4 Drawing Sheets

(56) References Cited

U.S. PATENT DOCUMENTS

| | | |
|---|---|---|
| 2008/0234267 A1 | 9/2008 | Lackey ................. 514/235.2 |
| 2009/0215770 A1 | 8/2009 | Jung et al. |
| 2009/0226443 A1 | 9/2009 | Filvaroff et al. ........... 424/138.1 |
| 2010/0069412 A1 | 3/2010 | Heron et al. |
| 2011/0053935 A1 | 3/2011 | Folkes et al. .............. 514/235.2 |
| 2011/0237629 A1 | 9/2011 | Meibom et al. ............. 514/340 |
| 2011/0262436 A1 | 10/2011 | Bender et al. ............. 424/133.1 |
| 2012/0041024 A1 | 2/2012 | Charnley et al. ............ 514/313 |
| 2012/0053183 A1 | 3/2012 | Russu et al. |
| 2012/0219522 A1 | 8/2012 | Xi ............................... 424/85.4 |
| 2013/0018039 A1 | 1/2013 | Bodmer et al. .......... 514/210.21 |
| 2013/0023532 A1 | 1/2013 | Casillas et al. ............ 514/234.2 |
| 2013/0023534 A1 | 1/2013 | Casillas et al. ............ 514/236.5 |
| 2013/0053375 A1 | 2/2013 | Bury et al. ................. 514/228.2 |
| 2013/0345258 A1 | 12/2013 | Bury et al. ................... 514/313 |
| 2014/0256949 A1 | 9/2014 | Casillas et al. |

FOREIGN PATENT DOCUMENTS

| | | | |
|---|---|---|---|
| WO | WO 96/09294 A1 | 3/1996 | |
| WO | WO 98/05647 A1 | 2/1998 | |
| WO | WO 99/35146 A1 | 7/1999 | |
| WO | WO 02/068394 A1 | 9/2002 | |
| WO | WO 02/092571 A1 | 11/2002 | |
| WO | WO 03/018022 A1 | 3/2003 | |
| WO | WO 03/026666 A1 | 4/2003 | |
| WO | WO 04/037814 A1 | 5/2004 | |
| WO | WO 2008/33748 A2 | 3/2008 | |
| WO | WO 2008/33749 A2 | 3/2008 | |
| WO | WO 2009/080200 A1 | 7/2009 | |
| WO | WO2009080200 | 7/2009 | ............. C07D 44/42 |
| WO | WO 2011/011522 A2 | 1/2011 | |
| WO | WO 2011/112588 A1 | 9/2011 | |
| WO | WO 2011/120025 A1 | 9/2011 | |
| WO | WO 2011/120026 A1 | 9/2011 | |
| WO | WO 2011/123609 A1 | 10/2011 | |
| WO | WO 2011/140442 A1 | 11/2011 | |
| WO | WO 2012/021580 A1 | 2/2012 | |
| WO | WO 2012/122011 A2 | 9/2012 | |
| WO | WO 2013/025958 A1 | 2/2013 | |
| WO | WO 2014/043437 A1 | 3/2014 | |
| WO | WO 2014/043446 A1 | 3/2014 | |
| WO | WO 2014/128622 | 8/2014 | |

OTHER PUBLICATIONS

Ferrero-Miliani, et al., *Clinical and Experimental Immunology*, 147:227-235 (2006).
Foley, et al., *Pediatric Rheumatology*, 11 (Suppl. 1):A3 (2013).
Geddes, et al., *Infection and Immunity*, 78(12):5107-5115 (2010).
Goh, et al., *The Journal of Immunology*, 191:2691-2699 (2013).
Goncalves, et al., *The Scandanavian Journal of Immunology*, 73:428-435 (2011).
Hedegaard, et al., *Plos One*, 6(5):e20253 (2011).
Heinhuis, et al., *Ann Rheum Dis*, 69:1866-1872 (2009).
Hysi, et al., *Human Molecular Genetics*, 14(7):935-941 (2005).
Ikeda, et al., *Arthritis Research & Therapy*, 16:R89 (2014).
Jamontt, et al., *Journal of Immunology*, 190:2948-2958 (2013).
Jun, et al., *Journal of Leukocyte Biology*, 94:927-932 (2013).
Kruger, et al., *European Society for Organ Transplantation*, 20:600-607 (2007).
Kvarnhammar, et al., *Plos One*, 8(7):e68701 (2013).
Liu, et al., *Journal of Biological Sciences*, 11(5):525-535 (2015).
McGovern, et al., *Human Molecular Genetics*, 14(10):1245-1250 (2005).
Murias, et al., *Pediatric Rheumatology*, 12(Suppl. 1):P293 (2014).
Nachbur, et al., *Nature Communications*, 6:6442 (2015).
Natarajan, et al., *Journal of Neuroimmunology*, 265:51-60 (2013).
Oh, et al., *Plos Pathogens*, 9(5):e1003351 (2013).
Ospelt, et al., *Arthritis & Rheumatism*, 60(2):355-363 (2009).
Paim-Marque, et al., *Pediatric Rheumatology*, 12(Suppl. 1):P272 (2014).
Penack, et al., *The Journal of Experimental Medicine*, 206(10):2101-2110 (2009).
Peng, et al., *International Immunopharmacology*, 13:440-445 (2012).
Pillai, et al., *Seminars in Ophthalmology*, 28(5-6):327-332 (2013).
Plantinga, et al., *Rheumatology*, 52:806-814 (2013).
Rebane, et al., *The Journal of Allergy & Clinical Immunology*, 129:1297-1306 (2012).
Rosenzweig, et al., *Arthritis & Rheumatism*, 62(4):1051-1059 (2010).
Rosenzweig, et al., *Inflammation Research*, 60:705-714 2011).
Rosenzweig, et al., *Investigative Ophthalmology & Visual Science*, 50(4):1746-1753 (2009).
Rosenzweig, et al., *Investigative Ophthalmology & Visual Science*, 50(4):1739-1745 (2009).
Saha, et al., *Cell Host & Microbe*, 5:137-150 (2009).
Sfriso, et al., *Autoimmunity Reviews*, 12:44-51 (2012).
Shaw, et al., *Immunity*, 34:75-84 (2011).
Shigeoka, et al., *The Journal of Immunology*, 184:2297-2304 (2010).
Uehara, et al., *Diagnostic Pathology*, 4(23):1746 (2009).
Vieira, et al., *The Journal of Immunology*, 188:5116-5122 (2012).
Walsh, et al., *Cytokine & Growth Factor Reviews*, 24:91-104 (2013).
Wiken, et al., *The Journal of Clinical Immunology*, 29:78-89 (2009).
Yu, et al., *Plos One*, 6(8):e23855 (2011).
Zhou, et al., *Diabetes & Metabolism*, 38:538-543 (2012).
Cai, et al. Journal of Medicinal Chemistry, 53(5): 2000-2009 (2010).
EP Supplementary Search Report for PCT/US2012/027439, dated Dec. 16, 2014.
Amendment, U.S. Appl. No. 14/283,352, filed Apr. 7, 2015.
Amendment, U.S. Appl. No. 14/396,559, filed Apr. 7, 2015.
Amendment, U.S. Appl. No. 14/002,147, filed Oct. 9, 2014.
Amendment, U.S. Appl. No. 13/696,603, filed Feb. 6, 2015.
Foley et al., Pediatric Rheumatology, 2013,11 (Suppl)A3 (published Nov. 8, 2013; presented 7th Congress of ISSAID, Lusanne, Switzerland May 22-26, 2013).
Poster: C.R Hanning, AAI Annual Meeting, Pittsburgh PA (May 4, 2014).
Poster. B. J Votta, et al., Keystone Symposia on Innate Immunity, Keystone, CO (Mar. 7, 2012).
EP Supplementary Search Report for PCT/US2012/051247,dated Feb. 18, 2015.
Sheth, et al. Archives of Biochemistry & Biophysics, 503: 191-201 (2010).
Amendment, U.S. Appl. No. 14/397,218, filed Nov. 24, 2014.
Amendment, U.S. Appl. No. 14/396,559, filed Nov. 24, 2014.
Poster: B. J. Votta, et al., Keystone Symposia on Innate Immunity, Keystone, CO (Mar. 7, 2012).
Poster (Word): B. J. Votta, et al., Keystone Symposia on Innate Immunity, Keystone, CO (Mar. 7, 2012).
Poster: C.R. Hanning, AAI Annual Meeting, Pittsburgh PA (May 4, 2014).
Poster (Word): C.R. Hanning, AAI Annual Meeting, Pittsburgh PA (May 4, 2014).
Cavasotto, et al. Bioorg. & Med. Chem. Lett., 16: 1969-1974 (2006).
Kumar, et al. J. Clin. Oncol., 26: 1742-1751 (Apr. 1, 2008).
Manon, et al. J. Molec. Biol., 365: 160-174 (2007).
Robinett, et al. Bioorg. Med. Chem. Lett., 17: 5886-5893 (2007).
Argast, et al. Molec. & Cell. Biochem., (Kluwer Academic Pubs) 268(1-2): 129-140 (2005).
PCT International Preliminary Report on Patentability & PCT Written Opinion of the International Searching Authority, PCT/US11/35521, dated Aug. 9, 2011.
PCT International Preliminary Report on Patentability & PCT Written Opinion of the International Searching Authority, PCT/US11/47183, dated Dec. 30, 2011.
PCT International Preliminary Report on Patentability & PCT Written Opinion of the International Searching Authority, PCT/US12/27439, dated Jun. 7, 2012.

(56) References Cited

OTHER PUBLICATIONS

PCT International Preliminary Report on Patentability & PCT Written Opinion of the International Searching Authority, PCT/US12/51247, dated Oct. 23, 2012.
PCT International Preliminary Report on Patentability & PCT Written Opinion of the International Searching Authority, PCT/US13/59600, dated Jan. 29, 2014.
PCT International Preliminary Report on Patentability & PCT Written Opinion of the International Searching Authority, PCT/US13/59619, dated Jan. 29, 2014.
EP Supplementary Search Report for PCT/US11/030103, dated Sep. 23, 2013.
EP Supplementary Search Report for PCT/US11/030104, dated Sep. 17, 2013.
EP Supplementary Search Report for PCT/US11/35521, dated Oct. 23, 2013.
EP Supplementary Search Report for PCT/US11/47183, dated Dec. 17, 2013.
Manon, et al. Journal of Molecular Biology, 365:160-174 (2007).
Cai, Xiong Discovery of 7-(4-(3-Ethynylphenylamino)-7-methoxyquinazolin-6-yloxy)-N-hydroxyheptanamid e (CUDC-101) as a Potent Multi-Acting HDAC, EGFR, and HER2 Inhibitor for the Treatment of Cancer Journal of Medicinal Chemistry (2010), 53(5), 2000-2009 CODEN: JMCMAR; ISSN: 0022-2623; English.

\* cited by examiner

AMINO QUINAZOLINES AS KINASE INHIBITORS

BACKGROUND OF THE INVENTION

Field of the Invention

The present invention relates to quinazolyl amines that inhibit RIP2 kinase and methods of making and using the same. Specifically, the present invention relates to substituted quinazolyl amines as RIP2 kinase inhibitors.

Background of the Invention

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J. Biol. Chem.* 273, 12296-12300; (1998) *Current Biology* 8, 885-889; and (1998) *J. Biol. Chem.* 273, 16968-16975). The CARD domain of RIP2 kinase mediates interaction with other CARD-containing proteins, such as NOD1 and NOD2 42000) *J. Biol. Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J. Biol. Chem.* 284, 19183-19188).

Dysregulation of RIP2-dependent signaling has been linked to autoinflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J. Hum. Genet.* 70, 845-857; (2004) *European Journal of Human Genetics* 12, 206-212; (2008) *Mucosal Immunology* (2008) 1 (Suppl 1), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extra-intestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in autoinflammatory diseases characterized by increased and/or dysregulated RIP2 kinase activity.

SUMMARY OF THE INVENTION

The invention is directed to quinazolyl amine compounds according to Formula (I):

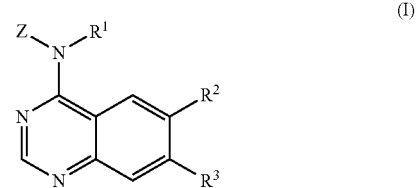

wherein:

$R^1$ is H, —$SO_2(C_1\text{-}C_4)$alkyl, —$CO(C_1\text{-}C_4)$alkyl, or $(C_1\text{-}C_4)$alkyl;

$R^2$ is —$SR^a$, —$SOR^a$, —$SO_2R^a$, —$SO_2NH_2$, or —$SO_2NR^bR^c$, wherein $R^a$ is $(C_1\text{-}C_6)$alkyl, halo$(C_1\text{-}C_6)$alkyl, $(C_3\text{-}C_7)$cycloalkyl, 4-7 membered heterocycloalkyl, aryl, or heteroaryl, wherein:

said $(C_1\text{-}C_6)$alkyl is optionally substituted by one or two groups each independently selected from the group consisting of cyano, hydroxyl, $(C_1\text{-}C_6)$alkoxy, $(C_1\text{-}C_6)$alkoxy$(C_2\text{-}C_6)$alkoxy, —$CO_2H$, —$CO_2(C_1\text{-}C_4)$alkyl, —$SO_2(C_1\text{-}C_4)$alkyl, $(C_3\text{-}C_7)$cycloalkyl, phenyl, 5-6 membered heteroaryl, 9-10 membered heteroaryl, 4-7 membered heterocycloalkyl and (phenyl)($C_1\text{-}C_4$ alkyl)amino-, wherein said $(C_3\text{-}C_7)$cycloalkyl, phenyl, (phenyl)($C_1\text{-}C_4$ alkyl)amino-, 5-6 membered heteroaryl, 9-10 membered heteroaryl or 4-7 membered heterocycloalkyl is optionally substituted by 1-3 groups each independently selected from the group consisting of halogen, —$CF_3$, hydroxyl, amino, (($C_1\text{-}C_4$)alkyl)amino-, (($C_1\text{-}C_4$)alkyl)(($C_1\text{-}C_4$)alkyl)amino-, ($C_1\text{-}C_4$)alkyl, phenyl($C_1\text{-}C_4$)alkyl-, hydroxy($C_1\text{-}C_4$)alkyl and ($C_1\text{-}C_4$)alkoxy, said $(C_3\text{-}C_7)$cycloalkyl or 4-7 membered heterocycloalkyl is optionally substituted by 1-3 groups each independently selected from the group consisting of halogen, —$CF_3$, hydroxyl, amino, (($C_1\text{-}C_4$)alkyl)amino-, (($C_1\text{-}C_4$)alkyl)(($C_1\text{-}C_4$)alkyl)amino-, ($C_1\text{-}C_4$)alkyl, phenyl($C_1\text{-}C_4$)alkyl-, hydroxy($C_1\text{-}C_4$)alkyl-, oxo and ($C_1\text{-}C_4$)alkoxy, and said aryl or heteroaryl is optionally substituted by 1-3 groups each independently selected from the group consisting of halogen, —$CF_3$, hydroxyl, amino, (($C_1\text{-}C_4$)alkyl)amino-, (($C_1\text{-}C_4$)alkyl)(($C_1\text{-}C_4$)alkyl)amino-, ($C_1\text{-}C_4$)alkyl, phenyl($C_1\text{-}C_4$)alkyl-, hydroxy($C_1\text{-}C_4$)alkyl- and ($C_1\text{-}C_4$)alkoxy;

$R^b$ is $(C_1-C_6)$alkyl or 4-7 membered heterocycloalkyl, wherein:
  said $(C_1-C_6)$alkyl is optionally substituted by one or two groups each independently selected from the group consisting of hydroxyl, $(C_1-C_6)$alkoxy, $(C_1-C_6)$alkoxy$(C_2-C_6)$ alkoxy, —$CO_2H$, —$CO_2(C_1-C_4)$alkyl, $(C_1-C_4$ alkyl)amino-, $(C_1-C_4$ alkyl)$(C_1-C_4$ alkyl)amino-, 5-6 membered heteroaryl, and 4-7 membered heterocycloalkyl, wherein said 5-6 membered heteroaryl or 4-7 membered heterocycloalkyl is optionally substituted by 1-3 groups each independently selected from the group consisting of halogen, $(C_1-C_4)$alkyl, hydroxy$(C_1-C_4)$alkyl and $(C_1-C_4)$alkoxy,
  said 4-7 membered heterocycloalkyl is optionally substituted by 1-3 groups each independently selected from the group consisting of hydroxyl, amino, $(C_1-C_4)$alkyl, $(C_1-C_4)$alkoxycarbonyl-, hydroxy$(C_1-C_4)$alkyl-, oxo and $(C_1-C_4)$alkoxy, and
  $R^c$ is H, $(C_1-C_4)$alkoxy or $(C_1-C_6)$alkyl;
or $R^b$ and $R^c$ taken together with the nitrogen atom to which they are attached form a 3-7 membered heterocycloalkyl group, optionally containing one or two additional ring heteroatoms each independently selected from nitrogen and oxygen, wherein said 3-7 membered heterocycloalkyl is optionally substituted by 1-3 groups each independently selected from the group consisting of $(C_1-C_4)$alkyl, hydroxy, —$CO_2H$ and —$CO(C_1-C_4)$alkyl;

$R^3$ is H, halogen, hydroxy, $(C_1-C_4)$alkyl-, $(C_2-C_4)$alkenyl-, halo$(C_1-C_4)$alkyl-, hydroxy$(C_2-C_4)$alkenyl-, $(C_1-C_4)$alkoxy-, $(C_2-C_4)$alkenyloxy-, halo$(C_1-C_4)$alkoxy-, $(C_1-C_4)$alkoxy$(C_1-C_6)$alkyl-, halo$(C_1-C_4)$alkoxy$(C_1-C_6)$alkyl-, $(C_1-C_4)$alkoxy$(C_2-C_6)$alkoxy-, halo$(C_1-C_4)$alkoxy$(C_2-C_6)$alkoxy-, hydroxy$(C_1-C_6)$alkyl-, hydroxy$(C_2-C_6)$alkoxy-, hydroxy$(C_3-C_4)$alkenyl-, cyano$(C_1-C_4)$alkyl-, cyano$(C_2-C_6)$alkoxy-, $(C_1-C_4)$alkyl-thio-$(C_2-C_4)$alkoxy, $(C_1-C_4)$alkyl-sulfonyl-$(C_2-C_4)$alkoxy-, carboxy-$(C_1-C_6)$alkoxy-, carboxy-$(C_2-C_4)$alkenyl-oxy-, $(C_1-C_4)$alkoxycarbonyl$(C_1-C_6)$alkoxy-, $(C_1-C_4)$alkoxycarbonyl$(C_2-C_4)$alkenyl-oxy-, carboxy$(C_2-C_4)$alkenyl-, $(C_1-C_4)$alkoxycarbonyl$(C_2-C_4)$alkenyl-, aminocarbonyl$(C_1-C_6)$alkoxy-, aminocarbonyl$(C_2-C_4)$alkenyl-oxy-, $(C_3-C_6)$cycloalkyl$(C_1-C_4)$alkoxy-, $(C_3-C_6)$cycloalkoxy-, 4-6 membered-heterocycloalkyl$(C_1-C_4)$alkoxy-, or 4-6 membered-heterocycloalkyl-oxy- (that is, 4-6 membered-heterocycloalkoxy-),
  wherein the halo$(C_1-C_4)$alkyl-, halo$(C_1-C_4)$alkoxy-, halo$(C_1-C_4)$alkoxy$(C_1-C_6)$alkyl-, or halo$(C_1-C_4)$alkoxy$(C_2-C_6)$ alkoxy-groups contain 2 or 3 halo atoms,
  wherein the $(C_3-C_6)$cycloalkyl moiety of the $(C_3-C_6)$ cycloalkyl$(C_1-C_4)$alkoxy- or $(C_3-C_6)$cycloalkoxy- is optionally substituted by a group selected from the group consisting of cyano, halo, hydroxyl, $(C_1-C_6)$alkoxy and $(C_1-C_4)$ alkoxy$(C_2-C_6)$alkoxy, and
  wherein the 4-6 membered heterocycloalkyl moiety of the 4-6 membered heterocycloalkyl$(C_1-C_4)$alkoxy-, or 4-6 membered-heterocycloalkyl-oxy- is optionally substituted by a group selected from the group consisting of cyano, halo, hydroxyl, $(C_1-C_6)$alkoxy and $(C_1-C_4)$alkoxy$(C_2-C_6)$alkoxy;

Z is phenyl or aryl$(C_1-C_4)$alkyl-, wherein in the phenyl group or the aryl moiety of the aryl$(C_1-C_4)$alkyl- group is substituted by $R^4$, $R^5$, $R^6$ and $R^7$, wherein:
  $R^4$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, wherein the phenyl moiety of said phenoxy or phenyl$(C_1-C_4)$alkoxy- is optionally substituted by 1-3 substituents each independently selected from the group consisting of halogen, —$CF_3$, $(C_1-C_4)$alkyl and $(C_1-C_4)$alkoxy; and
  each of $R^5$, $R^6$ and $R^7$ is independently selected from the group consisting of H, hydroxyl, halogen, —$CF_3$, hydroxy $(C_1-C_4)$alkyl, $(C_1-C_4)$alkyl and $(C_1-C_4)$alkoxy; or Z is phenyl or pyridyl, substituted by $R^8$, $R^9$ and $R^{10}$, wherein:
  $R^8$ and $R^9$ are located on adjacent atoms and taken together with the atoms to which they are attached form a 5-membered ring containing 1, 2 or 3 heteroatoms each independently selected from N, O and S, which 5-membered ring is substituted by $R^{11}$;
    wherein one of $R^{10}$ or $R^{11}$ is H, halogen, cyano, $(C_1-C_4)$ alkyl, halo$(C_1-C_4)$alkyl, $(C_1-C_4)$alkoxy, phenoxy, phenyl $(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy; and
    the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy; or Z is pyrazolyl, having the formula:

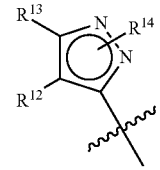

wherein:
  $R^{12}$ is H, methyl or hydroxymethyl;
  $R^{13}$ is methyl, trifluoromethyl or hydroxymethyl;
  $R^{14}$ is H, OH, or $(C_1-C_3)$alkyl; or
  $R^{12}$ and $R^{13}$, taken together with the atoms to which they are attached, form a 6-membered ring substituted by $R^{15}$ and $R^{16}$, wherein the 6-membered ring optionally contains 1 nitrogen atom;
  wherein $R^{15}$ and $R^{16}$ are each independently selected from the group consisting of H, halogen, cyano, $(C_1-C_4)$alkyl, halo$(C_1-C_4)$alkyl, $(C_1-C_4)$alkoxy, phenoxy, phenyl$(C_1-C_4)$ alkoxy, hydroxyl, hydroxy$(C_1-C_4)$alkyl-, and aminocarbonyl, wherein the phenyl moiety of said phenoxy or phenyl $(C_1-C_4)$alkoxy is optionally substituted by 1-3 substituents each independently selected from the group consisting of halogen, —$CF_3$, $(C_1-C_4)$alkyl and $(C_1-C_4)$alkoxy;

or a salt, particularly a pharmaceutically acceptable salt, thereof.

In selected embodiments of this invention, the compounds of Formula (I) do not include:
ethyl 5-{[4-[(3-chloro-4-fluorophenyl)amino]-7-(methoxy)-6-quinazolinyl]thio}pentanoate,
ethyl 4-{[4-[(3-chloro-4-fluorophenyl)amino]-7-(methoxy)-6-quinazolinyl]thio}butanoate,
ethyl 7-{[4-[(3-chloro-4-fluorophenyl)amino]-7-(methoxy)-6-quinazolinyl]thio}heptanoate,
N-(3-chloro-4-fluorophenyl)-7-methoxy-6-[(trifluoromethyl)sulfonyl]-4-quinazolinamine,
ethyl 7-{[4-[(3-chloro-4-fluorophenyl)amino]-7-(methoxy)-6-quinazolinyl]sulfonyl}heptanoate,
N-[(3,4-difluorophenyl)methyl]-6-[(methyl)sulfonyl]-4-quinazolinamine,
3-methoxy-5-[[6-[(methylthio)]-4-quinazolinyl]amino]-phenol,
3-methoxy-5-[[6-[(methylsulfinyl)]-4-quinazolinyl]amino]-phenol, N-[(3,4-dichlorophenyl)methyl]-6-(methylthio)-4-quinazolinamine,
N-[(3-fluoro-4-methoxyphenyl)methyl]-6-(methylthio)-4-quinazolinamine,
6-(methylthio)-N-[4-(phenylmethoxy)phenyl]-4-quinazolinamine,
6-(methylsulfonyl)-N-[4-(phenylmethoxy)phenyl]-4-quinazolinamine,
6-(methylsulfinyl)-N-[4-(phenylmethoxy)phenyl]-4-quinazolinamine,
6-(methylthio)-N-(4-(phenoxyphenyl)-4-quinazolinamine,
N-(3-(methylphenyl)-6-(methylthio)-4-quinazolinamine,
or a salt thereof.

The compounds according to Formula (I), or salts, particularly pharmaceutically acceptable salts, thereof, are inhibitors of RIP2 kinase.

Accordingly, the present invention is also directed to a method of inhibiting RIP2 kinase which method comprises contacting a cell with a compound according to Formula (I), or a salt, particularly a pharmaceutically acceptable salt, thereof.

The invention is further directed to a method of treating a RIP2 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Examples of RIP2 kinase-mediated diseases or disorders include uveitis, Crohn's disease, ulcerative colitis, early-onset and extra-intestinal inflammatory bowel disease and granulomateous disorders, such as sarcoidosis, Blau syndrome, early-onset sarcoidosis and Wegner's Granulomatosis.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP2 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

Figure 1:
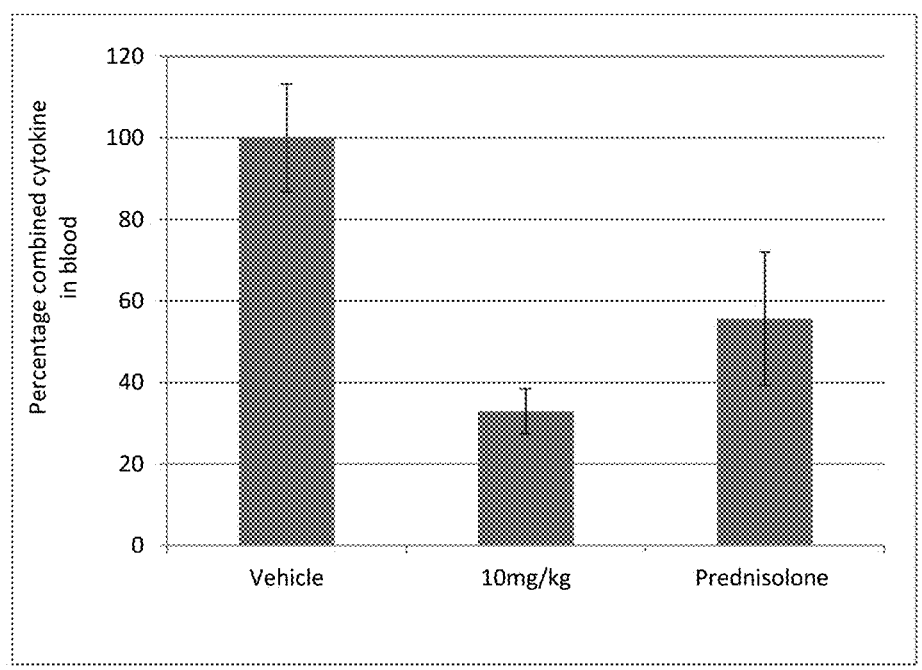
FIG. 1 shows the combined cytokine response in rat whole blood samples obtained after pre-dosing rats with the compound of Example 4 or prednisolone, followed by dosing with L18-MDP.
Figure 2:
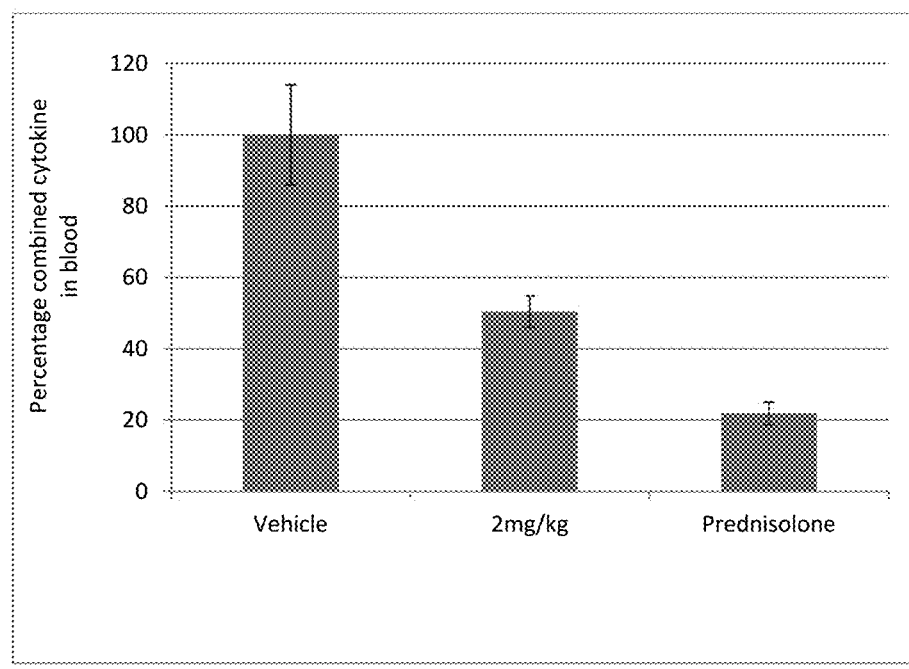
FIG. 2 shows the combined cytokine response in rat whole blood samples obtained after pre-dosing rats with the compound of Example 6 or prednisolone, followed by dosing with L18-MDP.
Figure 3:
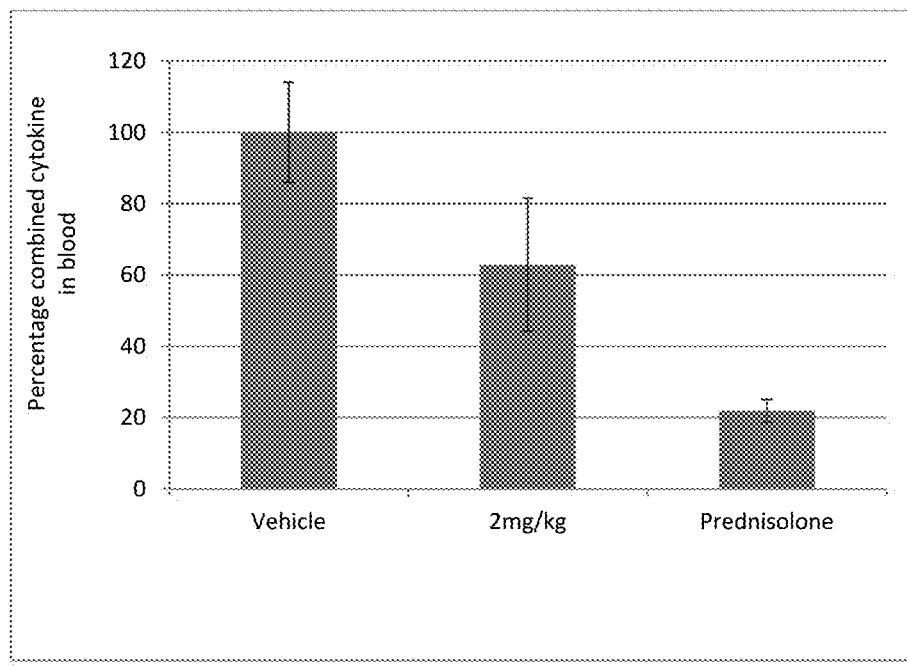
FIG. 3 shows the combined cytokine response in rat whole blood samples obtained after pre-dosing rats with the compound of Example 16 or prednisolone, followed by dosing with L18-MDP.
Figure 4:
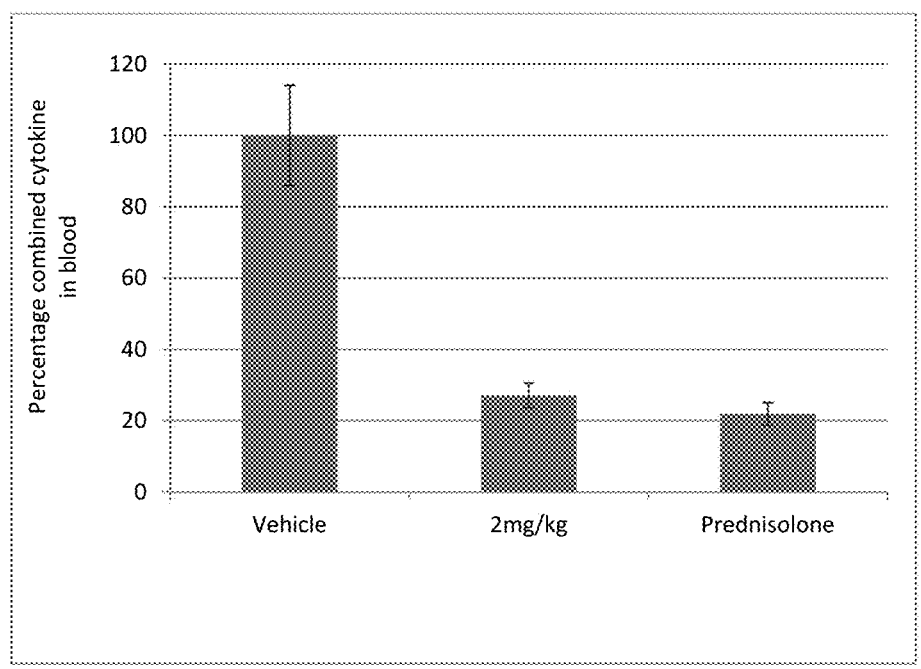
FIG. 4 shows the combined cytokine response in rat whole blood samples obtained after pre-dosing rats with the compound of Example 21 or prednisolone, followed by dosing with L18-MDP.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will also be appreciated by those skilled in the art that when Z is pyrazolyl, the compounds of this invention may exist as pyrazole isomers represented by Formula (I-A) and Formula (I-B):

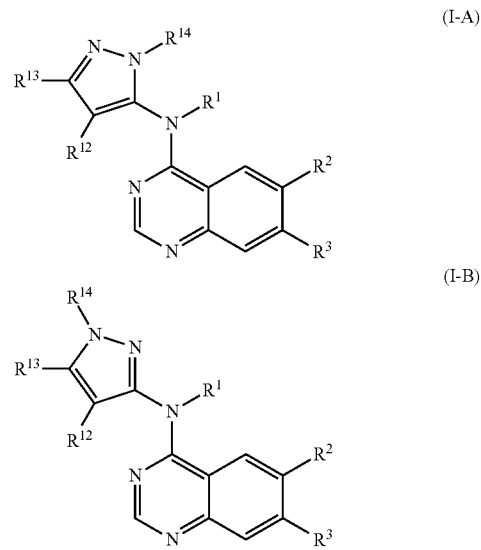

When $R^{14}$ is H, the compounds of this invention may exist as tautomers. However, when $R^{14}$ is $(C_1-C_3)$alkyl, the compounds of this invention, may exist as either one of the regioisomers represented by Formula (I-A) or Formula (I-B), or as a mixture thereof.

In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

As used herein, the term "alkyl" represents a saturated, straight or branched hydrocarbon moiety. Exemplary alkyls include, but are not limited to methyl (Me), ethyl (Et), n-propyl, isopropyl, n-butyl, s-butyl, isobutyl, t-butyl and pentyl. The term "$C_1-C_4$ alkyl" refers to an alkyl group or moiety containing from 1 to 4 carbon atoms.

When the term "alkyl" is used in combination with other substituent groups, such as "haloalkyl" or "hydroxyalkyl" or "arylalkyl", the term "alkyl" is intended to encompass a divalent straight or branched-chain hydrocarbon radical. For example, "arylalkyl" is intended to mean the radical alkylaryl, wherein the alkyl moiety thereof is a divalent straight or branched-chain carbon radical and the aryl moiety thereof is as defined herein, and is represented by the bonding arrangement present in a benzyl group (—CH$_2$-phenyl); "halo($C_1-C_4$)alkyl" or "($C_1-C_4$)haloalkyl" is intended to mean a radical having one or more halogen atoms, which may be the same or different, at one or more carbon atoms of an alkyl moiety containing from 1 to 4 carbon atoms, which a is straight or branched-chain carbon radical, and is represented by a trifluoromethyl group (—CF$_3$).

As used herein, the term "cycloalkyl" refers to a non-aromatic, saturated, cyclic hydrocarbon ring. The term "($C_3$-$C_7$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, and cycloheptyl.

"Alkoxy" refers to a group containing an alkyl radical attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, isobutoxy, and t-butoxy.

"Aryl" represents a group or moiety comprising an aromatic, monocyclic or bicyclic hydrocarbon radical containing from 6 to 10 carbon ring atoms, which may be fused one or more cycloalkyl rings. Generally, in the compounds of this invention, aryl is phenyl.

A heterocyclic group or moiety is a cyclic group or moiety having as ring members atoms of at least two different elements (carbon and one or more of nitrogen, oxygen and/or sulfur), which cyclic group or moiety may be saturated or partially unsaturated (non-aromatic; e.g., a heterocycloalkyl group or moiety) or fully unsaturated (aromatic; e.g., a heteroaryl group or moiety).

"Heterocycloalkyl" represents a group or moiety comprising a non-aromatic, monocyclic or bicyclic radical, which is saturated or partially unsaturated, containing 3 to 10 ring atoms, unless otherwise specified, which includes 1 to 4 heteroatoms selected from nitrogen, oxygen and sulfur. Illustrative examples of heterocycloalkyls include, but are not limited to, azetidinyl, oxetanyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl and 1,5,9-triazacyclododecyl.

In some of the compounds of this invention, heterocycloalkyl groups include 4-membered heterocycloalkyl groups containing one heteroatom, such as oxetanyl, thietanyl and azetidinyl.

In other compounds of this invention, heterocycloalkyl groups include 5-membered heterocycloalkyl groups containing one heteroatom selected from nitrogen, oxygen and sulfur and optionally containing one or two an additional nitrogen atoms, or optionally containing one additional oxygen or sulfur atom, such as pyrrolidyl (or pyrrolidinyl), tetrahydrofuryl (or tetrahydrofuranyl), tetrahydrothienyl, dihydrofuryl, oxazolinyl, thiazolinyl, imidazolinyl, pyrazolinyl, 1,3-dioxolanyl, and 1,3-oxathiolan-2-on-yl.

In other compounds of this invention, heterocycloalkyl groups are 6-membered heterocycloalkyl groups containing one heteroatom selected from nitrogen, oxygen and sulfur and optionally containing one or two an additional nitrogen atoms or one additional oxygen or sulfur atom, such as piperidyl (or piperidinyl), piperazinyl, morpholinyl, thiomorpholinyl, 1,1dioxoido-thiomorpholin-4-yl, tetrahydropyranyl, dihydropyranyl, tetrahydro-2H-1,4-thiazinyl, 1,4-dioxanyl, 1,3-oxathianyl, and 1,3-dithianyl.

"Heteroaryl" refers to a group or moiety comprising an aromatic monocyclic or bicyclic radical, containing 5 to 10 ring atoms, including 1 to 4 heteroatoms selected from nitrogen, oxygen and sulfur. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur. Illustrative examples of heteroaryls include, but are not limited to, thienyl, pyrrolyl, imidazolyl, pyrazolyl, furyl (or furanyl), isothiazolyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, and isothiazolyl.

In some embodiments, the heteroaryl groups present in the compounds of this invention are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl (furanyl), isothiazolyl, isoxazolyl, oxazolyl, oxadiazolyl, thiazolyl, triazolyl and tetrazolyl or pyridyl, pyrazinyl, pyrimidinyl, pyridazinyl and triazinyl.

In other embodiments, the heteroaryl groups present in the compounds of this invention are 9-membered or 10-membered monocyclic heteroaryl groups. Selected 9-10 membered heteroaryl groups contain one nitrogen, oxygen or sulfur ring heteroatom, and optionally contain 1, 2, 3 or 4 additional nitrogen ring atoms.

In some of the compounds of this invention, heteroaryl groups include a 9-membered heteroaryl group, which includes benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl (2-oxo-1,3-benzoxathiolyl), purinyl and imidazopyridinyl.

In some of the compounds of this invention, heteroaryl groups include a 10-membered heteroaryl group, which includes chromenyl, chromanyl, quinolyl, isoquinolyl, phthalazinyl, naphthridinyl, quinazolinyl, quinoxalinyl, 4H-quinolizinyl, tetrahydroquinolinyl, cinnolinyl, and pteridinyl.

It is to be understood that the terms heterocyclic, heteroaryl, and heterocycloalkyl are intended to encompass stable heterocyclic groups where a ring nitrogen heteroatom is optionally oxidized (e.g., heterocyclic groups containing an N-oxide, such as pyridine-N-oxide) or where a ring sulfur heteroatom is optionally oxidized (e.g., heterocyclic groups containing sulfones or sulfoxide moieties, such as tetrahydrothienyl-1-oxide (a tetrahydrothienyl sulfoxide) or tetrahydrothienyl-1,1-dioxide (a tetrahydrothienyl sulfone)).

"Oxo" represents a double-bonded oxygen moiety; for example, if attached directly to a carbon atom forms a carbonyl moiety (C=O). The terms "halogen" and "halo" represent chloro, fluoro, bromo or iodo substituents. "Hydroxy" or "hydroxyl" is intended to mean the radical —OH.

As used herein, the terms "compound(s) of the invention" or "compound(s) of this invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

In one embodiment of the compounds of Formula (I) of this invention, $R^1$ is H, —SO$_2$(C$_1$-C$_4$)alkyl, —CO(C$_1$-C$_4$)alkyl, or (C$_1$-C$_4$)alkyl;

$R^2$ is —SR$^a$, —SOR$^a$, or —SO$_2$R$^a$, wherein R$^a$ is (C$_1$-C$_6$)alkyl, halo(C$_1$-C$_6$)alkyl, (C$_3$-C$_7$)cycloalkyl, 4-7 membered heterocycloalkyl, aryl, or heteroaryl, wherein:

said (C$_1$-C$_6$)alkyl is optionally substituted by one or two groups each independently selected from cyano, hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, —SO$_2$(C$_1$-C$_4$)alkyl, (C$_3$-C$_7$)cycloalkyl, phenyl, 5-6 membered heteroaryl, 9-10 membered heteroaryl, 4-7 membered heterocycloalkyl and (phenyl)(C$_1$-C$_4$ alkyl)amino-, wherein said (C$_3$-C$_7$)cycloalkyl, phenyl, (phenyl)(C$_1$-C$_4$ alkyl)amino-, 5-6 membered heteroaryl, 9-10 membered heteroaryl or 4-7 membered heterocycloalkyl is optionally substituted by 1-3 groups each independently selected from halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl and (C$_1$-C$_4$)alkoxy, said (C$_3$-C$_7$)cycloalkyl or 4-7 membered heterocycloalkyl is optionally substituted by 1-3 groups each independently selected from halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl-, oxo and (C$_1$-C$_4$)alkoxy, and said aryl or heteroaryl is optionally substituted by 1-3 groups each independently selected from halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl- and (C$_1$-C$_4$)alkoxy;

$R^3$ is H, halogen, hydroxy, (C$_1$-C$_4$)alkyl-, (C$_2$-C$_4$)alkenyl-, halo(C$_1$-C$_4$)alkyl-, (C$_1$-C$_4$)alkoxy-, halo(C$_1$-C$_4$)alkoxy-, (C$_1$-C$_4$)alkoxy(C$_1$-C$_6$)alkyl-, halo(C$_1$-C$_4$)alkoxy(C$_1$-C$_6$)alkyl-, (C$_1$-C$_4$)alkoxy(C$_2$-C$_6$)alkoxy-, halo(C$_1$-C$_4$)alkoxy(C$_2$-C$_6$)alkoxy-, hydroxy(C$_1$-C$_6$)alkyl-, hydroxy(C$_2$-C$_6$)alkoxy-, cyano(C$_1$-C$_4$)alkyl-, cyano(C$_2$-C$_6$)alkoxy-, carboxy-(C$_1$-C$_6$)alkoxy-, (C$_1$-C$_4$)alkoxycarbonyl(C$_1$-C$_6$) alkoxy-, (C$_3$-C$_6$)cycloalkyl(C$_1$-C$_4$)alkoxy-, (C$_3$-C$_6$)cycloalkoxy-, 4-6 membered-heterocycloalkyl(C$_1$-C$_4$)alkoxy-, or 4-6 membered-heterocycloalkoxy-, wherein the halo(C$_1$-C$_4$)alkyl-, halo(C$_1$-C$_4$)alkoxy-, halo (C$_1$-C$_4$)alkoxy(C$_1$-C$_6$)alkyl-, or halo(C$_1$-C$_4$)alkoxy(C$_2$-C$_6$) alkoxy-groups contain 2 or 3 halo atoms; and wherein the (C$_3$-C$_6$)cycloalkyl moiety of the (C$_3$-C$_6$) cycloalkyl(C$_1$-C$_4$)alkoxy- or (C$_3$-C$_6$)cycloalkoxy-, is optionally substituted by a group selected from cyano, halo, hydroxyl, (C$_1$-C$_6$)alkoxy and (C$_1$-C$_4$)alkoxy(C$_2$-C$_6$)alkoxy;

wherein the 4-6 membered-heterocycloalkyl moiety of the 4-6 membered-heterocycloalkyl(C$_1$-C$_4$)alkoxy-, or 4-6 membered-heterocycloalkoxy-, is optionally substituted by a group selected from cyano, halo, hydroxyl, (C$_1$-C$_6$)alkoxy and (C$_1$-C$_4$)alkoxy(C$_2$-C$_6$)alkoxy;

Z is phenyl or aryl(C$_1$-C$_4$)alkyl-, substituted by $R^4$, $R^5$, $R^6$ and $R^7$, wherein:

$R^4$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, wherein the phenyl moiety of said phenoxy or phenyl(C$_1$-C$_4$)alkoxy- is optionally substituted by 1-3 substituents each independently selected from halogen, —CF$_3$, (C$_1$-C$_4$)alkyl and (C$_1$-C$_4$)alkoxy; and each of $R^5$, $R^6$ and $R^7$ is independently selected from H, hydroxyl, halogen, —CF$_3$, hydroxy(C$_1$-C$_4$)alkyl, (C$_1$-C$_4$) alkyl and (C$_1$-C$_4$)alkoxy; or Z is phenyl or pyridyl substituted by $R^8$, $R^9$ and $R^{10}$, wherein:

$R^8$ and $R^9$ are located on adjacent atoms and taken together with the atoms to which they are attached form a 5-membered heterocyclic group containing 1, 2 or 3 heteroatoms each independently selected from N, O and S, which 5-membered heterocyclic group is substituted by $R^{11}$;

wherein one of $R^{10}$ or $R^{11}$ is H, halogen, cyano, (C$_1$-C$_4$) alkyl, halo(C$_1$-C$_4$)alkyl, (C$_1$-C$_4$)alkoxy, phenoxy, phenyl (C$_1$-C$_4$)alkoxy, hydroxyl, hydroxy(C$_1$-C$_4$)alkyl-, or aminocarbonyl, where the phenyl moiety of said phenoxy or phenyl(C$_1$-C$_4$)alkoxy is optionally substituted by 1-3 substituents each independently selected from halogen, —CF$_3$, (C$_1$-C$_4$)alkyl and (C$_1$-C$_4$)alkoxy; and the other of $R^{10}$ or $R^{11}$ is H, hydroxyl, halogen, —CF$_3$, hydroxy(C$_1$-C$_4$)alkyl, (C$_1$-C$_4$)alkyl or (C$_1$-C$_4$)alkoxy; or Z is pyrazolyl, having the formula:

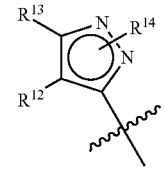

wherein:

$R^{12}$ is H, methyl or hydroxymethyl;

$R^{13}$ is methyl, trifluoromethyl or hydroxymethyl;

$R^{14}$ is H, OH, or (C$_1$-C$_3$)alkyl; or $R^{12}$ and $R^{13}$, taken together with the atoms to which they are attached, form a 6 membered carbocyclic ring or heterocyclic ring substituted by $R^{15}$ and $R^{16}$, wherein the heterocyclic ring contains 1 nitrogen atom;

wherein $R^{15}$ and $R^{16}$ are each independently selected from H, halogen, cyano, (C$_1$-C$_4$)alkyl, halo(C$_1$-C$_4$)alkyl, (C$_1$-C$_4$) alkoxy, phenoxy, phenyl(C$_1$-C$_4$)alkoxy, hydroxyl, hydroxy (C$_1$-C$_4$)alkyl-, and aminocarbonyl, wherein the phenyl moiety of said phenoxy or phenyl(C$_1$-C$_4$)alkoxy is optionally substituted by 1-3 substituents each independently selected from halogen, —CF$_3$, (C$_1$-C$_4$)alkyl and (C$_1$-C$_4$)alkoxy.

In selected embodiments, the compounds of Formula (I) do not include ethyl 5-{[4-[(3-chloro-4-fluorophenyl)amino]-7-(methoxy)-6-quinazolinyl]thio}pentanoate; ethyl 4-{[4-[(3-chloro-4-fluorophenyl)amino]-7-(methoxy)-6-quinazolinyl]thio}butanoate; ethyl 4-{[4-[(3-chloro-4-fluorophenyl)amino]-7-(methoxy)-6-quinazolinyl]thio}heptanoate; 7-(methoxy)-N-[1-(phenylmethyl)-1H-indazol-5-yl]-6-[(trifluoromethyl)sulfonyl]-4-quinazolinamine; or ethyl 4-{[4-[(3-chloro-4-fluorophenyl)amino]-7-(methyloxy)-6-quinazolinyl]sulfonyl}heptanoate.

In another embodiment of this invention, R$^1$ is H. In other embodiments, R$^1$ is (C$_1$-C$_3$)alkyl; specifically, —CH$_3$ or —CH$_2$CH$_3$. Generally, in the compounds of this invention, R$^1$ is H.

In one embodiment, R$^2$ is —SR$^a$ or —SO$_2$R$^a$. In a further embodiment, R$^2$ is —SOR$^a$. In a still further embodiment, R$^2$ is —SO$_2$R$^a$.

In one embodiment of the compounds of this invention, R$^a$ is an optionally substituted (C$_1$-C$_6$)alkyl, (C$_3$-C$_6$)cycloalkyl, 4-6-membered heterocycloalkyl, 5-6-membered heteroaryl or phenyl group;

wherein said (C$_1$-C$_6$)alkyl is optionally substituted by one or two groups each independently selected from the group consisting of hydroxyl, (C$_1$-C$_4$)alkoxy, —CO$_2$(C$_1$-C$_4$)alkyl, —SO$_2$(C$_1$-C$_4$)alkyl, and a (C$_3$-C$_6$)cycloalkyl, phenyl, 4-6-membered heterocycloalkyl, 5-6-membered heteroaryl, or 9-10-membered heteroaryl, where said (C$_3$-C$_6$)cycloalkyl, phenyl, 4-6-membered heterocycloalkyl, 5-6-membered heteroaryl, or 9-10-membered heteroaryl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy; and wherein said (C$_3$-C$_6$)cycloalkyl, 4-6-membered heterocycloalkyl, 5-6-membered heteroaryl or phenyl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy.

Suitably, R$^a$ is an unsubstituted (C$_1$-C$_6$)alkyl or a (C$_1$-C$_6$) alkyl substituted by one or two groups each independently selected from the group consisting of hydroxyl, (C$_1$-C$_4$)alkoxy, —CO$_2$(C$_1$-C$_4$)alkyl, —SO$_2$(C$_1$-C$_4$)alkyl, and a cyclic substituent which is a (C$_3$-C$_6$)cycloalkyl, phenyl, 4-6-membered heterocycloalkyl, 5-6-membered heteroaryl, or 9-10-membered heteroaryl, where the (C$_3$-C$_6$)cycloalkyl, phenyl, 4-6-membered heterocycloalkyl, 5-6-membered heteroaryl, or 9-10-membered heteroaryl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy.

Suitably, R$^a$ is an optionally substituted (C$_3$-C$_6$)cycloalkyl, 4-6-membered heterocycloalkyl, 5-6-membered heteroaryl or phenyl group, wherein the (C$_3$-C$_6$)cycloalkyl, 4-6-membered heterocycloalkyl, 5-6-membered heteroaryl or phenyl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy.

When R$^a$ is a heterocycloalkyl or heteroaryl group, it is to be understood that the heterocycloalkyl or heteroaryl group is bonded to the sulfur atom of the —SR$^a$, —SOR$^a$ or —SO$_2$R$^a$ moiety by a ring carbon atom.

In a still further embodiment, R$^a$ is an optionally substituted (C$_1$-C$_6$)alkyl, (C$_3$-C$_6$)cycloalkyl, or 4-6-membered heterocycloalkyl group, wherein said (C$_1$-C$_6$)alkyl is optionally substituted by a group selected from the group consisting of hydroxyl, (C$_1$-C$_2$) alkoxy, (C$_1$-C$_2$)alkoxy(C$_2$-C$_3$)alkoxy-, —SO$_2$(C$_1$-C$_2$)alkyl, and a group selected from the group consisting of (C$_3$-C$_6$) cycloalkyl (optionally substituted by (C$_1$-C$_4$)alkyl or hydroxy(C$_1$-C$_4$)alkyl), 4-6-membered heterocycloalkyl (optionally substituted by (C$_1$-C$_4$)alkyl or halogen), 5-6-membered heteroaryl (optionally substituted by (C$_1$-C$_4$)alkyl or hydroxy(C$_1$-C$_4$)alkyl), phenyl, and 9-10-membered heteroaryl, and said (C$_3$-C$_6$)cycloalkyl or 4-6-membered heterocycloalkyl is optionally substituted by 1-3 groups each independently selected from the group consisting of halogen, (C$_1$-C$_4$)alkyl, and hydroxy(C$_1$-C$_4$)alkyl-, wherein any of said 5-6 membered heterocycloalkyl groups contains 1 heteroatom selected from N, O and S. Particularly, in this embodiment, when R$^a$ is an optionally substituted (C$_1$-C$_6$)alkyl, said (C$_1$-C$_6$)alkyl is optionally substituted by a group selected from the group consisting of hydroxyl, (C$_1$-C$_2$)alkoxy, and (C$_1$-C$_2$)alkoxy(C$_2$-C$_3$) alkoxy-.

In a still further embodiment, R$^a$ is an optionally substituted (C$_1$-C$_6$)alkyl or 5-6-membered heterocycloalkyl group, wherein:

said (C$_1$-C$_6$)alkyl is optionally substituted by a substituent selected from the group consisting of hydroxyl, (C$_1$-C$_2$) alkoxy, (C$_1$-C$_2$)alkoxy(C$_2$-C$_3$)alkoxy-, amino, (C$_1$-C$_3$ alkyl)amino-, (C$_1$-C$_3$ alkyl)(C$_1$-C$_2$ alkyl)amino-, 5-6-membered heterocycloalkyl (optionally substituted by (C$_1$-C$_4$)alkyl), and C$_3$-C$_6$cycloalkyl (optionally substituted by (C$_1$-C$_4$)alkyl or hydroxy(C$_1$-C$_4$)alkyl), and said 5-6 membered heterocycloalkyl is optionally substituted by 1 or 2 groups each independently selected from the group consisting of halogen, (C$_1$-C$_4$)alkyl, and hydroxy(C$_1$-C$_4$)alkyl-;

wherein any of said 5-6 membered heterocycloalkyl contains 1 heteroatom selected from N, O and S.

In another embodiment, R$^a$ is halo(C$_1$-C$_4$)alkyl containing 1-9 halogen atoms. In specific embodiments, R$^a$ is halo(C$_1$-C$_2$)alkyl, specifically a halo(C$_1$-C$_2$)alkyl containing 1-5 halogen atoms, and more specifically a halo(C$_1$-C$_2$)alkyl containing 3 halogen atoms.

In another embodiment, R$^a$ is (C$_1$-C$_6$)alkyl, optionally substituted by a substituent selected from the group consisting of hydroxyl, (C$_1$-C$_2$)alkoxy, and (C$_1$-C$_2$)alkoxy(C$_2$-C$_3$) alkoxy-. In yet another embodiment, R$^a$ is a 5-6-membered heterocycloalkyl group optionally substituted by 1 or 2 independently selected (C$_1$-C$_4$)alkyl groups.

In a specific embodiment, R$^a$ is an unsubstituted (C$_1$-C$_5$) alkyl. In a further embodiment of the compounds of this invention, R$^a$ is an unsubstituted (C$_1$-C$_4$)alkyl group. In another embodiment, R$^a$ is a (C$_1$-C$_5$)alkyl group substituted by a hydroxyl, (C$_1$-C$_2$)alkoxy, or (C$_1$-C$_2$)alkoxy(C$_2$-C$_3$) alkoxy-group. In another specific embodiment, R$^a$ is a (C$_1$-C$_5$)alkyl substituted by one hydroxyl group. In yet another specific embodiment, R$^a$ is a tetrahydropyranyl group.

In a specific embodiment, R$^a$ is —CH$_3$, —CH(CH$_3$)$_2$, or —C(CH$_3$)$_3$. In another specific embodiment, R$^a$ is —CH$_2$CH$_2$OH or —C(CH$_3$)$_2$CH$_2$CH$_2$OH. In yet another specific embodiment, R$^a$ is tetrahydro-2H-pyran-4-yl.

In one embodiment, R$^b$ is (C$_1$-C$_6$)alkyl or 4-7 membered heterocycloalkyl, wherein:

said (C$_1$-C$_6$)alkyl is optionally substituted by one or two groups each independently selected from the group consisting of hydroxyl, $(C_1-C_6)$alkoxy, $(C_1-C_6)$alkoxy$(C_2-C_6)$alkoxy, —$CO_2H$, —$CO_2(C_1-C_4)$alkyl, $(C_1-C_4$ alkyl)amino-, $(C_1-C_4$ alkyl)$(C_1-C_4$ alkyl)amino-, 5-6 membered heteroaryl, and 4-7 membered heterocycloalkyl, wherein said 5-6 membered heteroaryl or 4-7 membered heterocycloalkyl is optionally substituted by 1-3 groups each independently selected from the group consisting of halogen, $(C_1-C_4)$alkyl, hydroxy$(C_1-C_4)$alkyl and $(C_1-C_4)$alkoxy, said 4-7 membered heterocycloalkyl is optionally substituted by 1-3 groups each independently selected from the group consisting of hydroxyl, amino, $(C_1-C_4)$alkyl, hydroxy$(C_1-C_4)$alkyl-, oxo and $(C_1-C_4)$alkoxy, and $R^c$ is H or $(C_1-C_4)$alkyl;

or $R^b$ and $R^c$ taken together with the nitrogen atom to which they are attached form a 5-7 membered heterocycloalkyl group, optionally containing one additional ring heteroatom selected from nitrogen and oxygen, wherein said 5-7 membered heterocycloalkyl is optionally substituted by 1-3 groups each independently selected from the group consisting of $(C_1-C_4)$alkyl, hydroxy, —$CO_2H$ and —$CO(C_1-C_4)$alkyl.

In another embodiment, $R^b$ is $(C_1-C_6)$alkyl and said $(C_1-C_6)$alkyl is optionally substituted by 1 or 2 substituents each independently selected from the group consisting of hydroxyl, $(C_1-C_4)$alkoxy, $(C_1-C_4)$alkoxy$(C_2-C_4)$alkoxy-, $(C_1-C_4$ alkyl)amino-, $(C_1-C_4$ alkyl)$(C_1-C_4$ alkyl)amino-, —$CO_2(C_1-C_4)$alkyl, and a 4-6-membered heterocycloalkyl or 5-6-membered heteroaryl, where said 4-6-membered heterocycloalkyl or 5-6-membered heteroaryl is optionally substituted by 1-3 groups each independently selected from the group consisting of hydroxyl, amino, $(C_1-C_4)$alkyl, hydroxy$(C_1-C_4)$alkyl- and $(C_1-C_4)$alkoxy.

In a further embodiment, $R^b$ is unsubstituted $(C_1-C_6)$alkyl, particularly, $R^b$ is unsubstituted $(C_1-C_4)$alkyl. In another embodiment, $R^b$ is a $(C_1-C_6)$alkyl substituted by for 2 substituents each independently selected from the group consisting of hydroxyl, $(C_1-C_2)$alkoxy, $(C_1-C_2)$alkoxy$(C_2-C_3)$alkoxy-, $(C_1-C_3$ alkyl)amino-, $(C_1-C_3$ alkyl)$(C_1-C_2$ alkyl)amino-, —$CO_2(C_1-C_2)$alkyl, and a 4-6-membered heterocycloalkyl optionally substituted by $(C_1-C_4)$alkyl, or a 5-6-membered heteroaryl optionally substituted by $(C_1-C_4)$alkyl.

Particularly, $R^b$ is a $(C_1-C_4)$alkyl substituted by hydroxyl, $(C_1-C_2)$alkoxy, $(C_1-C_3$ alkyl)amino-, $(C_1-C_3$ alkyl)$(C_1-C_2$ alkyl)amino-, a 4-6-membered heterocycloalkyl, optionally substituted by $(C_1-C_4)$alkyl, or a 5-6-membered heteroaryl, optionally substituted by $(C_1-C_4)$alkyl.

In one embodiment, $R^b$ is —$CH_3$ or —$CH(CH_3)_2$. In another embodiment, $R^b$ is —$CH_2CH_2OH$, —$CH_2CH_2OCH_3$, —$CH_2C(CH_3)_2OH$, —$CH_2CH(CH_3)OH$, or —$CH_2CH_2N(CH_3)_2$. In a further embodiment, $R^b$ is -oxetan-3-yl, tetrahydro-2H-pyran-4-yl, —$CH_2$-tetrahydro-2H-pyran-4-yl, or —$CH_2CH_2$-1H-tetrazol-5-yl.

In one embodiment of this invention, $R^c$ is H or $(C_1-C_4)$alkyl. In some specific embodiments, $R^c$ is —$CH_3$. In other specific embodiments, $R^c$ is H.

In a further embodiment, $R^b$ and $R^c$ taken together with the nitrogen atom to which they are attached form a 5-7 membered heterocycloalkyl group, optionally containing one additional ring heteroatom selected from nitrogen and oxygen, which 5-7 membered heterocycloalkyl is optionally substituted by 1-3 groups each independently selected from the group consisting of ($(C_1-C_4)$alkyl, hydroxy, —$CO_2H$ and —$CO(C_1-C_4)$alkyl.

In a still further embodiment, $R^b$ and $R^c$ taken together with the nitrogen atom to which they are attached form a 5-6-membered heterocycloalkyl, optionally containing 1 additional heteroatom selected from N and O, and optionally substituted by a hydroxyl, $(C_1-C_4)$alkyl, carboxy or $(C_1-C_4)$alkylcarbonyl-group.

In yet another embodiment, $R^b$ and $R^c$ taken together with the nitrogen atom to which they are attached form a morpholin-4-yl, 4-methylcarbonyl-piperazin-1-yl (that is, 4-acetyl-piperazin-1-yl), pyrrolidin-1-yl, 3-hydroxy-pyrrolidin-1-yl, or 2-(carboxy)-1-pyrrolidin-1-yl group.

In one embodiment of this invention, $R^3$ is H.

In another embodiment of this invention, $R^3$ is halogen, hydroxy, $(C_1-C_3)$alkyl-, $(C_2-C_3)$alkenyl-, halo$(C_1-C_2)$alkyl-, hydroxy$(C_2-C_3)$alkenyl-, $(C_1-C_4)$alkoxy-, $(C_2-C_3)$alkenyl-oxy-, halo$(C_1-C_3)$alkoxy-, $(C_5-C_6)$cycloalkyl$(C_1-C_3)$alkoxy-, 5-6-membered-heterocycloalkyl-oxy-, $(C_1-C_3)$alkoxy$(C_1-C_4)$alkyl-, $(C_1-C_3)$alkoxy$(C_2-C_4)$alkoxy-, $(C_1-C_3)$alkyl-thio-$(C_2-C_4)$alkoxy-, $(C_1-C_3)$alkyl-sulfonyl-$(C_2-C_4)$alkoxy-, carboxy-$(C_1-C_4)$alkoxy-, carboxy-$(C_2-C_4)$alkenyl-oxy-, $(C_1-C_3)$alkoxycarbonyl$(C_1-C_4)$alkoxy-, $(C_1-C_3)$alkoxycarbonyl$(C_2-C_4)$alkenyl-oxy-, aminocarbonyl$(C_1-C_4)$alkoxy-, aminocarbonyl$(C_2-C_4)$alkenyl-oxy-, or hydroxy$(C_2-C_4)$alkoxy-.

In another embodiment of this invention, $R^3$ is halogen, hydroxy, $(C_1-C_3)$alkyl-, $(C_2-C_3)$alkenyl-, halo$(C_1-C_2)$alkyl-, hydroxy$(C_2-C_3)$alkenyl-, $(C_1-C_4)$alkoxy-, $(C_2-C_3)$alkenyl-oxy-, halo$(C_1-C_3)$alkoxy-, $(C_5-C_6)$cycloalkyl$(C_1-C_3)$alkoxy-, 5-6-membered-heterocycloalkyl-oxy-, $(C_1-C_3)$alkoxy$(C_1-C_4)$alkyl-, $(C_1-C_3)$alkoxy$(C_2-C_3)$alkoxy-, $(C_1-C_3)$alkyl-thio-$(C_2-C_3)$alkoxy-, $(C_1-C_3)$alkyl-sulfonyl-$(C_2-C_3)$alkoxy-, carboxy-$(C_1-C_4)$alkoxy-, carboxy-$(C_2-C_4)$alkenyl-oxy-, $(C_1-C_3)$alkoxycarbonyl$(C_1-C_4)$alkoxy-, $(C_1-C_3)$alkoxycarbonyl$(C_2-C_4)$alkenyl-oxy-, aminocarbonyl$(C_1-C_3)$alkoxy-, aminocarbonyl$(C_2-C_3)$alkenyl-oxy-, or hydroxy$(C_2-C_4)$alkoxy-.

In yet another embodiment, $R^3$ is H or $R^3$ is halogen, hydroxy, $(C_1-C_4)$alkyl-, $(C_2-C_4)$alkenyl-, halo$(C_1-C_4)$alkyl-, $(C_1-C_4)$alkoxy-, halo$(C_1-C_4)$alkoxy-, $(C_3-C_6)$cycloalkyl$(C_1-C_4)$alkoxy-, 5-6-membered-heterocycloalkyl-oxy-, $(C_1-C_4)$alkoxy$(C_1-C_6)$alkyl-, $(C_1-C_4)$alkoxy$(C_2-C_6)$alkoxy-, carboxy-$(C_1-C_6)$alkoxy-, $(C_1-C_4)$alkoxycarbonyl$(C_1-C_6)$alkoxy-, hydroxy$(C_1-C_6)$alkyl-, or hydroxy$(C_2-C_6)$alkoxy-.

In a further embodiment, $R^3$ is H, halogen, hydroxy, $(C_1-C_3)$alkyl-, $(C_2-C_3)$alkenyl-, halo$(C_1-C_2)$alkyl-, $(C_1-C_4)$alkoxy-, halo$(C_1-C_3)$alkoxy-, $(C_5-C_6)$cycloalkyl$(C_1-C_3)$alkoxy-, 5-6-membered-heterocycloalkyl-oxy-, $(C_1-C_3)$alkoxy$(C_1-C_4)$alkyl-, $(C_1-C_3)$alkoxy$(C_2-C_4)$alkoxy-, carboxy-$(C_1-C_4)$alkoxy-, $(C_1-C_3)$alkoxycarbonyl$(C_1-C_4)$alkoxy-, or hydroxy$(C_2-C_4)$alkoxy-.

In a specific embodiment, $R^3$ is chloro, —$CH_2CH_3$, —$CH=CH_2$, —$CH=CHCH_2OH$, —$OCH=CH_2$, —$OCH=CH$—$CO_2H$, —$OCH=CH$—$CO_2CH_3$, —$OCH=CH$—$CONH_2$, —OH, —$OCH_3$, —$OCF_2H$, —$OCH(CH_3)_2$, —$OCH_2CH_3$, —$OCH_2CF_3$, —$OCH_2CH_2CH_3$, —$OCH_2CH_2Cl$, —$OCH_2CH_2Br$, —$OCH_2CH_2SCH_3$, —$OCH_2CH_2SO_2CH_3$, —$OCH_2CH_2SO_2CH(CH_3)_2$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OCH(CH_3)CO_2CH_3$, —$OCH_2CH(CH_3)OH$, —$OC(CH_3)_2CO_2CH_2CH_3$, —$OCH_2CO_2H$, —$OCH_2CONH_2$, —$OCH_2$-cyclohexyl, or —O-tetrahydro-2H-pyran-4-yl.

In a more specific embodiment, $R^3$ is H, chloro, —$CH_2CH_3$, —$CH=CH_2$, —OH, —$OCH_3$, —$OCF_2H$, —$OCH(CH_3)_2$, —$OCH_2CH_3$, —$OCH_2CF_3$, —$OCH_2CH_2Cl$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OC(CH_3)_2CO_2CH_2CH_3$, cyclohexylmethyloxy-, or tetrahydro-2H-pyran-4-yloxy-.

In another embodiment, Z is phenyl substituted by $R^4$, $R^5$, $R^6$ and $R^7$ wherein:

$R^4$ is H, halogen, cyano, $(C_1-C_4)$alkyl, halo$(C_1-C_4)$alkyl, $(C_1-C_4)$alkoxy, hydroxyl, or hydroxy$(C_1-C_4)$alkyl-; and each of $R^5$, $R^6$ and $R^7$ is independently selected from the group consisting of H, hydroxyl, halogen, hydroxy$(C_1-C_4)$alkyl, $(C_1-C_4)$alkyl, halo$(C_1-C_4)$alkyl and $(C_1-C_4)$alkoxy.

Specifically, Z is phenyl, substituted by 1, 2 or 3 (more specifically, 1 or 2) substituents each independently selected from the group consisting of hydroxyl, halogen, hydroxy$(C_1-C_4)$alkyl, $(C_1-C_4)$alkyl and $(C_1-C_4)$alkoxy. In specific embodiments, Z is 2-methyl-5-hydroxy-phenyl, 2-fluoro-4-chloro-phenyl, 3-methoxy-4-chloro-phenyl, or 3-hydroxy-4-chloro-phenyl. In selected embodiments, Z is 2-methyl-5-hydroxy-phenyl.

In a further embodiment of the compounds of Formula (I) of this invention, Z is phenyl or pyridyl substituted by $R^8$, $R^9$ and $R^{10}$, wherein:

$R^8$ and $R^9$ are located on adjacent atoms (carbon atoms) and taken together with the atoms to which they are attached form a 5-membered ring containing 1, 2 or 3 heteroatoms each independently selected from N, O and S, which 5-membered ring is substituted by $R^{11}$;

wherein one of $R^{10}$ or $R^{11}$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy; and the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy;

or Z is pyrazolyl, having the formula:

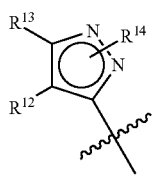

wherein:

$R^{12}$ is H, methyl or hydroxymethyl;

$R^{13}$ is methyl, trifluoromethyl or hydroxymethyl;

$R^{14}$ is H, OH, or $(C_1-C_3)$alkyl;

or $R^{12}$ and $R^{13}$, taken together with the atoms to which they are attached, form a 6-membered ring substituted by $R^{15}$ and $R^{16}$, wherein the 6-membered ring contains 1 nitrogen atom;

wherein $R^{15}$ and $R^{16}$ are each independently selected from the group consisting of H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, and aminocarbonyl, wherein the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy.

It will be understood by one skilled in the art that the 5-membered ring formed from $R^8$ and $R^9$ and the atoms to which they are attached may be non-aromatic (partially unsaturated) or aromatic (fully unsaturated). It will be further understood by one skilled in the art that the 6-membered ring formed from $R^{12}$ and $R^{13}$ and the atoms to which they are attached may be non-aromatic (partially unsaturated) or aromatic (fully unsaturated).

In another embodiment of the compounds of this invention, Z is not phenyl or aryl$(C_1-C_4)$alkyl-, wherein in the phenyl group or the aryl moiety of the aryl$(C_1-C_4)$alkyl- group is substituted by $R^4$, $R^5$, $R^6$ and $R^7$, wherein $R^4$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, wherein the phenyl moiety of said phenoxy or phenyl$(C_1-C_4)$alkoxy- is optionally substituted by 1-3 substituents each independently selected from the group consisting of halogen, —$CF_3$, $(C_1-C_4)$alkyl and $(C_1-C_4)$alkoxy; and each of $R^5$, $R^6$ and $R^7$ is independently selected from the group consisting of H, hydroxyl, halogen, —$CF_3$, hydroxy$(C_1-C_4)$alkyl, $(C_1-C_4)$alkyl and $(C_1-C_4)$alkoxy.

In yet another embodiment, Z is phenyl substituted by $R^8$, $R^9$ and $R^{10}$, wherein $R^8$ and $R^9$ are located on adjacent atoms and taken together with the atoms to which they are attached form a 5-membered ring containing 1, 2 or 3 heteroatoms each independently selected from N, O and S, which 5-membered ring is substituted by $R^{11}$; wherein $R^{10}$ and $R^{11}$ are each H or one of $R^{10}$ or $R^{11}$ is H, halogen, cyano, $(C_1-C_4)$alkyl, —$CF_3$, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy, and the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy. In this embodiment, Z is a 9-membered bicyclic heteroaryl group bonded to the amino ($NR^1$) moiety of Formula (I) via a substitutable carbon ring atom of the 6-membered, phenyl moiety of the 9-membered bicyclic heteroaryl group.

Specifically, Z is benzothiazolyl, optionally substituted by 1-3 substituents independently selected from the group consisting of halogen, $(C_1-C_4)$alkyl, halo$(C_1-C_4)$alkyl and $(C_1-C_4)$alkoxy. Accordingly, in one embodiment, Z is unsubstituted benzothiazolyl. In another embodiment, Z is benzothiazolyl substituted by 1-3 substituents independently selected from the group consisting of halogen, $(C_1-C_4)$alkyl, halo$(C_1-C_4)$alkyl and $(C_1-C_4)$alkoxy. More specifically, Z is benzo[d]thiazol-5-yl optionally substituted by chloro, fluoro, —$CF_3$, methyl, or methoxy. In a specific embodiment, Z is benzo[d]thiazol-5-yl.

In yet another embodiment, Z is pyridyl substituted by $R^8$, $R^9$ and $R^{10}$, wherein $R^8$ and $R^9$ are located on adjacent atoms (carbon atoms) and taken together with the atoms to which they are attached form a 5-membered ring containing 1, 2 or 3 heteroatoms each independently selected from N, O and S, which 5-membered ring is substituted by $R^{11}$; wherein one of $R^{10}$ or $R^{11}$ is H, halogen, cyano, $(C_1-C_4)$alkyl, —$CF_3$, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy and the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy. In this embodiment, Z is a 9-membered bicyclic heteroaryl group bonded to the amino ($NR^1$) moiety of Formula (I) via a substitutable carbon ring atom of the 6-membered, pyridyl moiety of the 9-membered bicyclic heteroaryl group.

In one embodiment, Z is pyrazolyl and $R^{12}$ is H or hydroxymethyl, $R^{13}$ is methyl or trifluoromethyl, and $R^{14}$ is H or methyl; or $R^{12}$ is H or methyl, $R^{13}$ is hydroxymethyl, and $R^{14}$ is H or methyl. In another embodiment, Z is pyrazolyl, $R^{12}$ is H or methyl, $R^{13}$ is methyl or trifluoromethyl, and $R^{14}$ is OH. In still another embodiment, Z is pyrazolyl, $R^{12}$ is H or methyl, $R^{13}$ is methyl or trifluoromethyl, and $R^{14}$ is H or methyl. In a further embodiment, Z is pyrazolyl, $R^{12}$ and $R^{13}$ are both methyl, and $R^{14}$ is H. In specific embodiments, Z is 5-(trifluoromethyl)-1H-pyrazol-3-yl, 1,3,4-trimethyl-1H-pyrazol-5-yl, or 4,5-dimethyl-1H-pyrazol-3-yl.

In a still further embodiment, Z is pyrazolyl, substituted by $R^{12}$ and $R^{13}$ wherein:

$R^{12}$ and $R^{13}$ are located on adjacent carbon atoms and taken together with the atoms to which they are attached form a 6 membered carbocyclic ring or heterocyclic ring substituted by $R^{15}$ and $R^{16}$;

wherein $R^{15}$ is H, halogen, cyano, $(C_1$-$C_4)$alkyl, —$CF_3$, $(C_1$-$C_4)$alkoxy, phenoxy, phenyl$(C_1$-$C_4)$alkoxy, hydroxyl, hydroxy$(C_1$-$C_4)$alkyl-, or aminocarbonyl, wherein the phenyl moiety of said phenoxy or phenyl$(C_1$-$C_4)$alkoxy is optionally substituted by 1-3 substituents each independently selected from the group consisting of halogen, —$CF_3$, $(C_1$-$C_4)$alkyl and $(C_1$-$C_4)$alkoxy; and $R^{16}$ is H, hydroxyl, halogen, —$CF_3$, hydroxy$(C_1$-$C_4)$alkyl, $(C_1$-$C_4)$alkyl or $(C_1$-$C_4)$alkoxy.

In another embodiment, the invention is directed to a compound according to Formula (I), wherein Z is a 9-membered bi-cyclic heteroaryl group, optionally substituted on either ring by halogen, cyano, $(C_1$-$C_4)$alkyl, halo$(C_1$-$C_4)$alkyl, $(C_1$-$C_4)$alkoxy, hydroxyl, hydroxy$(C_1$-$C_4)$alkyl- or aminocarbonyl, wherein the 9-membered bi-cyclic heteroaryl group is an optionally substituted indazolyl or pyrazolo[3,4-b]pyridinyl, bonded to the amino ($NR^1$) moiety via a substitutable carbon ring atom of the 5-membered pyrazolyl ring moiety of the indazolyl or pyrazolo[3,4-b]pyridinyl group, or a salt, particularly a pharmaceutically acceptable salt, thereof.

In a further embodiment, Z is an optionally substituted indazolyl or pyrazolo[3,4-b]pyridinyl, wherein the indazolyl or pyrazolo[3,4-b]pyridinyl is optionally substituted by hydroxyl, chloro, fluoro, —$CF_3$, cyano, hydroxymethyl-, methyl, methoxy or aminocarbonyl. In specific embodiments, Z is 5-fluoro-1H-indazol-3-yl, 1H-indazol-6-yl or 3-methyl-1H-indazol-6-yl. In selected embodiments, Z is 5-fluoro-1H-indazol-3-yl.

In another embodiment, the invention is directed to a compound according to Formula (II):

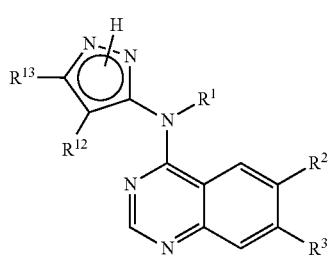

(II)

or a salt, particularly a pharmaceutically acceptable salt thereof, wherein IV, $R^1$, $R^2$, $R^3$, $R^{12}$ and $R^{13}$ are as defined herein.

In another embodiment, the invention is directed to method of inhibiting RIP2 kinase comprising contacting a cell with a compound according to Formula (III):

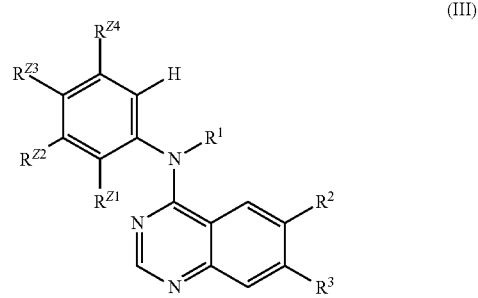

(III)

or a salt, particularly a pharmaceutically acceptable salt thereof, wherein $R^1$, $R^2$ and $R^3$ are as defined herein, and $R^{Z1}$ is H, halogen, —$CF_3$, $(C_1$-$C_4)$alkyl or $(C_1$-$C_4)$alkoxy; particularly, $R^{Z1}$ is H or methyl;

$R^{Z2}$ is H, halogen, —$CF_3$, $(C_1$-$C_4)$alkyl or $(C_1$-$C_4)$alkoxy;

$R^{Z3}$ is H, halogen, cyano, $(C_1$-$C_4)$alkyl, halo$(C_1$-$C_4)$alkyl, $(C_1$-$C_4)$alkoxy, phenoxy, phenyl$(C_1$-$C_4)$alkoxy, hydroxyl, hydroxy$(C_1$-$C_4)$alkyl-, or aminocarbonyl, wherein the phenyl moiety of said phenoxy or phenyl$(C_1$-$C_4)$alkoxy- is optionally substituted by 1-3 substituents each independently selected from the group consisting of halogen, —$CF_3$, $(C_1$-$C_4)$alkyl and $(C_1$-$C_4)$alkoxy; and $R^{Z4}$ is hydroxyl, hydroxy$(C_1$-$C_4)$alkyl or $(C_1$-$C_4)$alkoxy;

or a salt, particularly a pharmaceutically acceptable salt, thereof.

In one embodiment, the invention is directed to a compound of Formula (I), wherein:

$R^1$ is H or $(C_1$-$C_4)$alkyl;

$R^2$ is —$SR^a$ or —$SO_2R^a$, and $R^a$ is an optionally substituted $(C_1$-$C_6)$alkyl, $(C_3$-$C_6)$cycloalkyl, or 4-6-membered heterocycloalkyl group, wherein said $(C_1$-$C_6)$alkyl is optionally substituted by a groups selected from the group consisting of hydroxyl, $(C_1$-$C_2)$ alkoxy, $(C_1$-$C_2)$alkoxy$(C_2$-$C_3)$alkoxy-, —$SO_2(C_1$-$C_2)$alkyl, and a group selected from the group consisting of $(C_3$-$C_6)$ cycloalkyl (optionally substituted by $(C_1$-$C_4)$alkyl or hydroxy$(C_1$-$C_4)$alkyl), 4-6-membered heterocycloalkyl (optionally substituted by $(C_1$-$C_4)$alkyl or halogen), 5-6-membered heteroaryl (optionally substituted by $(C_1$-$C_4)$alkyl or hydroxy$(C_1$-$C_4)$alkyl), phenyl, and 9-10-membered heteroaryl, and said $(C_3$-$C_6)$cycloalkyl or 4-6-membered heterocycloalkyl is optionally substituted by 1-3 groups each independently selected from the group consisting of halogen, $(C_1$-$C_4)$alkyl, and hydroxy$(C_1$-$C_4)$alkyl-, wherein any of said 5-6 membered heterocycloalkyl groups contains 1 heteroatom selected from N, O and S;

$R^3$ is H, halogen, hydroxy, $(C_1$-$C_4)$alkyl-, $(C_2$-$C_4)$alkenyl-, halo$(C_1$-$C_4)$alkyl-, $(C_1$-$C_4)$alkoxy-, halo$(C_1$-$C_4)$alkoxy-, $(C_3$-$C_6)$cycloalkyl$(C_1$-$C_4)$alkoxy-, 5-6-membered-heterocycloalkyl-oxy-, $(C_1$-$C_4)$alkoxy$(C_1$-$C_6)$alkyl-, $(C_1$-$C_4)$alkoxy$(C_2$-$C_6)$alkoxy-, carboxy-$(C_1$-$C_6)$alkoxy-, $(C_1$-$C_4)$alkoxycarbonyl$(C_1$-$C_6)$alkoxy-, hydroxy$(C_1$-$C_6)$alkyl-, or hydroxy$(C_2$-$C_6)$alkoxy-;

Z is phenyl, substituted by 1, 2 or 3 substituents each independently selected from the group consisting of hydroxyl, halogen, hydroxy($C_1$-$C_4$)alkyl, ($C_1$-$C_4$)alkyl and ($C_1$-$C_4$)alkoxy, or Z is phenyl substituted by $R^8$, $R^9$ and $R^{10}$, wherein:

$R^8$ and $R^9$ are located on adjacent atoms and taken together with the atoms to which they are attached form a 5-membered ring containing 1, 2 or 3 heteroatoms each independently selected from N, O and S, which 5-membered ring is substituted by $R^{11}$;

wherein $R^{10}$ and $R^{11}$ are each H or one of $R^{10}$ or $R^{11}$ is H, halogen, cyano, ($C_1$-$C_4$)alkyl, —$CF_3$, ($C_1$-$C_4$)alkoxy, phenoxy, phenyl($C_1$-$C_4$)alkoxy, hydroxyl, hydroxy($C_1$-$C_4$)alkyl-, or aminocarbonyl, where the phenyl moiety of said phenoxy or phenyl($C_1$-$C_4$)alkoxy is optionally substituted by 1-3 substituents each independently selected from the group consisting of halogen, —$CF_3$, ($C_1$-$C_4$)alkyl and ($C_1$-$C_4$)alkoxy, and the other of $R^{10}$ or $R^{11}$ is H, hydroxyl, halogen, —$CF_3$, hydroxy($C_1$-$C_4$)alkyl, ($C_1$-$C_4$)alkyl or ($C_1$-$C_4$)alkoxy, or Z is pyrazolyl, wherein $R^{12}$ is H or methyl, $R^{13}$ is methyl or trifluoromethyl, and $R^{14}$ is H or methyl, or Z is pyrazolyl, substituted by $R^{12}$ and $R^{13}$ wherein:

$R^{12}$ and $R^{13}$ are located on adjacent carbon atoms and taken together with the atoms to which they are attached form a 6-membered carbocyclic ring or heterocyclic ring substituted by $R^{15}$ and $R^{16}$;

wherein $R^{15}$ is H, halogen, cyano, ($C_1$-$C_4$)alkyl, —$CF_3$, ($C_1$-$C_4$)alkoxy, phenoxy, phenyl($C_1$-$C_4$)alkoxy, hydroxyl, hydroxy($C_1$-$C_4$)alkyl-, or aminocarbonyl, wherein the phenyl moiety of said phenoxy or phenyl($C_1$-$C_4$)alkoxy is optionally substituted by 1-3 substituents each independently selected from the group consisting of halogen, —$CF_3$, ($C_1$-$C_4$)alkyl and ($C_1$-$C_4$)alkoxy; and $R^{16}$ is H, hydroxyl, halogen, —$CF_3$, hydroxy($C_1$-$C_4$)alkyl, ($C_1$-$C_4$)alkyl or ($C_1$-$C_4$)alkoxy;

or a salt, particularly a pharmaceutically acceptable salt, thereof. Particularly, in this embodiment, $R^2$ is —$SO_2R^a$ and/or $R^3$ is halogen, hydroxy, ($C_1$-$C_4$)alkyl-, ($C_2$-$C_4$)alkenyl-, halo($C_1$-$C_4$)alkyl-, ($C_1$-$C_4$)alkoxy-, halo($C_1$-$C_4$)alkoxy-, ($C_3$-$C_6$)cycloalkyl($C_1$-$C_4$)alkoxy-, 5-6-membered-heterocycloalkyl-oxy-, ($C_1$-$C_4$)alkoxy($C_1$-$C_6$)alkyl-, ($C_1$-$C_4$)alkoxy($C_2$-$C_6$)alkoxy-, carboxy-($C_1$-$C_6$)alkoxy-, ($C_1$-$C_4$)alkoxycarbonyl($C_1$-$C_6$)alkoxy-, hydroxy($C_1$-$C_6$)alkyl-, or hydroxy($C_2$-$C_6$)alkoxy- and/or Z is other than phenyl, substituted by 1, 2 or 3 substituents each independently selected from the group consisting of hydroxyl, halogen, hydroxy($C_1$-$C_4$)alkyl, ($C_1$-$C_4$)alkyl and ($C_1$-$C_4$)alkoxy.

In another embodiment, the invention is directed to a compound of Formula (I), wherein:

$R^1$ is H;

$R^2$ is —$SR^a$, —$SOR^a$ or —$SO_2R^a$, wherein $R^a$ is a ($C_1$-$C_6$)alkyl group, optionally substituted by a substituent selected from the group consisting of hydroxyl, ($C_1$-$C_2$)alkoxy, and ($C_1$-$C_2$)alkoxy($C_2$-$C_3$)alkoxy-, or $R^a$ is a 5-6-membered heterocycloalkyl group optionally substituted by 1 or 2 independently selected ($C_1$-$C_4$)alkyl groups;

$R^3$ is halogen, hydroxy, ($C_1$-$C_3$)alkyl-, ($C_2$-$C_3$)alkenyl-, halo($C_1$-$C_2$)alkyl-, hydroxy($C_2$-$C_3$)alkenyl-, ($C_1$-$C_4$)alkoxy-, ($C_2$-$C_3$)alkenyl-oxy-, halo($C_1$-$C_3$)alkoxy-, ($C_5$-$C_6$)cycloalkyl($C_1$-$C_3$)alkoxy-, 5-6-membered-heterocycloalkyl-oxy-, ($C_1$-$C_3$)alkoxy($C_1$-$C_4$)alkyl-, ($C_1$-$C_3$)alkoxy($C_2$-$C_3$)alkoxy-, ($C_1$-$C_3$)alkyl-thio-($C_2$-$C_3$)alkoxy-, ($C_1$-$C_3$)alkyl-sulfonyl-($C_2$-$C_3$)alkoxy-, carboxy-($C_1$-$C_4$)alkoxy-, carboxy-($C_2$-$C_4$)alkenyl-oxy-, ($C_1$-$C_3$)alkoxycarbonyl($C_1$-$C_4$)alkoxy-, ($C_1$-$C_3$)alkoxycarbonyl($C_2$-$C_4$)alkenyl-oxy-, aminocarbonyl($C_1$-$C_3$)alkoxy-, aminocarbonyl($C_2$-$C_3$)alkenyl-oxy-, or hydroxy($C_2$-$C_4$)alkoxy-;

Z is phenyl, substituted by 1 or 2 substituents each independently selected from the group consisting of hydroxyl, halogen, hydroxy($C_1$-$C_4$)alkyl, ($C_1$-$C_4$)alkyl and ($C_1$-$C_4$)alkoxy, or Z is benzothiazolyl, optionally substituted by 1-3 substituents independently selected from the group consisting of halogen, ($C_1$-$C_4$)alkyl, halo($C_1$-$C_4$)alkyl and ($C_1$-$C_4$)alkoxy, or Z is pyrazolyl, wherein $R^{12}$ is H or methyl, $R^{13}$ is methyl or trifluoromethyl, and $R^{14}$ is H or methyl, or Z is a 9-membered bi-cyclic heteroaryl group, optionally substituted on either ring by halogen, cyano, ($C_1$-$C_4$)alkyl, halo($C_1$-$C_4$)alkyl, ($C_1$-$C_4$)alkoxy, hydroxyl, hydroxy($C_1$-$C_4$)alkyl- or aminocarbonyl, wherein the 9-membered bi-cyclic heteroaryl group is an optionally substituted indazolyl or pyrazolo[3,4-b]pyridinyl, bonded to the amino (NW) moiety via a substitutable carbon ring atom of the 5-membered pyrazolyl ring moiety of the indazolyl or pyrazolo[3,4-b]pyridinyl group, or a salt, particularly a pharmaceutically acceptable salt, thereof.

In another embodiment, the invention is directed to a compound of Formula (I), wherein:

$R^1$ is H;

$R^2$ is —$SR^a$, —$SOR^a$ or —$SO_2R^a$, wherein $R^a$ is a ($C_1$-$C_6$)alkyl group, optionally substituted by a substituent selected from the group consisting of hydroxyl, ($C_1$-$C_2$)alkoxy, and ($C_1$-$C_2$)alkoxy($C_2$-$C_3$)alkoxy-;

$R^3$ is halogen, hydroxy, ($C_1$-$C_3$)alkyl-, ($C_2$-$C_3$)alkenyl-, halo($C_1$-$C_2$)alkyl-, hydroxy($C_2$-$C_3$)alkenyl-, ($C_1$-$C_4$)alkoxy-, ($C_2$-$C_3$)alkenyl-oxy-, halo($C_1$-$C_3$)alkoxy-, ($C_5$-$C_6$)cycloalkyl($C_1$-$C_3$)alkoxy-, 5-6-membered-heterocycloalkyl-oxy-, ($C_1$-$C_3$)alkoxy($C_1$-$C_4$)alkyl-, ($C_1$-$C_3$)alkoxy($C_2$-$C_3$)alkoxy-, ($C_1$-$C_3$)alkyl-thio-($C_2$-$C_3$)alkoxy-, ($C_1$-$C_3$)alkyl-sulfonyl-($C_2$-$C_3$)alkoxy-, carboxy-($C_1$-$C_4$)alkoxy-, carboxy-($C_2$-$C_4$)alkenyl-oxy-, ($C_1$-$C_3$)alkoxycarbonyl($C_1$-$C_4$)alkoxy-, ($C_1$-$C_3$)alkoxycarbonyl($C_2$-$C_4$)alkenyl-oxy-, aminocarbonyl($C_1$-$C_3$)alkoxy-, aminocarbonyl($C_2$-$C_3$)alkenyl-oxy-, or hydroxy($C_2$-$C_4$)alkoxy-;

Z is benzothiazolyl, optionally substituted by 1-3 substituents independently selected from the group consisting of halogen, ($C_1$-$C_4$)alkyl, halo($C_1$-$C_4$)alkyl and ($C_1$-$C_4$)alkoxy, or Z is pyrazolyl, wherein $R^{12}$ is H or methyl, $R^{13}$ is methyl or trifluoromethyl, and $R^{14}$ is H or methyl, or Z is a 9-membered bi-cyclic heteroaryl group, optionally substituted on either ring by halogen, cyano, ($C_1$-$C_4$)alkyl, halo($C_1$-$C_4$)alkyl, ($C_1$-$C_4$)alkoxy, hydroxyl, hydroxy($C_1$-$C_4$)alkyl- or aminocarbonyl, wherein the 9-membered bi-cyclic heteroaryl group is an optionally substituted indazolyl or pyrazolo[3,4-b]pyridinyl, bonded to the amino (NR$^1$) moiety via a substitutable carbon ring atom of the 5-membered pyrazolyl ring moiety of the indazolyl or pyrazolo[3,4-b]pyridinyl group;

or a salt, particularly a pharmaceutically acceptable salt, thereof.

In another embodiment, the invention is directed to a compound of Formula (I), wherein:

$R^1$ is H or —$CH_2CH_3$; particularly, $R^1$ is H;

$R^2$ is —$SR^a$ or —$SO_2R^a$, wherein:

$R^a$ is a ($C_1$-$C_6$)alkyl group, optionally substituted by a substituent selected from the group consisting of hydroxyl, ($C_1$-$C_2$)alkoxy, and ($C_1$-$C_2$)alkoxy($C_2$-$C_3$)alkoxy-, or $R^a$ is a 5-6-membered heterocycloalkyl group optionally substituted by 1 or 2 independently selected ($C_1$-$C_4$)alkyl groups;

$R^3$ is H, halogen, hydroxy, $(C_1-C_3)$alkyl-, $(C_2-C_3)$alkenyl-, halo$(C_1-C_2)$alkyl-, $(C_1-C_4)$alkoxy-, halo$(C_1-C_3)$alkoxy-, $(C_5-C_6)$cycloalkyl$(C_1-C_3)$alkoxy-, 5-6-membered heterocycloalkyl-oxy-, $(C_1-C_3)$alkoxy$(C_1-C_4)$alkyl-, $(C_1-C_3)$alkoxy$(C_2-C_4)$alkoxy-, carboxy-$(C_1-C_4)$alkoxy-, $(C_1-C_3)$alkoxycarbonyl$(C_1-C_4)$alkoxy-, or hydroxy$(C_2-C_4)$alkoxy-;

Z is phenyl, substituted by 1 or 2 substituents each independently selected from the group consisting of hydroxyl, halogen, hydroxy$(C_1-C_4)$alkyl, $(C_1-C_4)$alkyl and $(C_1-C_4)$alkoxy, or Z is benzothiazolyl, optionally substituted by 1-3 substituents independently selected from the group consisting of halogen, $(C_1-C_4)$alkyl, halo$(C_1-C_4)$alkyl or $(C_1-C_4)$alkoxy, or Z is pyrazolyl, wherein $R^{12}$ is H or methyl, $R^{13}$ is methyl or trifluoromethyl, and $R^{14}$ is H or methyl, or Z is a 9-membered bi-cyclic heteroaryl group, optionally substituted on either ring by halogen, cyano, $(C_1-C_4)$alkyl, halo$(C_1-C_4)$alkyl, $(C_1-C_4)$alkoxy, hydroxyl, hydroxy$(C_1-C_4)$alkyl- or aminocarbonyl, wherein the 9-membered bi-cyclic heteroaryl group is an optionally substituted indazolyl or pyrazolo[3,4-b]pyridinyl, bonded to the amino (NH) moiety via a substitutable carbon ring atom of the 5-membered pyrazolyl ring moiety of the indazolyl or pyrazolo[3,4-b]pyridinyl group, or a salt, particularly a pharmaceutically acceptable salt, thereof.

In another embodiment, the invention is directed to a compound of Formula (I), wherein:

$R^1$ is H;

$R^2$ is —$SO_2R^a$, wherein $R^a$ is an unsubstituted $(C_1-C_5)$ alkyl group or $R^a$ is a $(C_1-C_5)$alkyl group substituted by a hydroxyl, $(C_1-C_2)$alkoxy, or $(C_1-C_2)$alkoxy$(C_2-C_3)$alkoxy- group;

Z is benzothiazolyl, optionally substituted by a halogen, $(C_1-C_4)$alkyl, halo$(C_1-C_4)$alkyl or $(C_1-C_4)$alkoxy, or Z is pyrazolyl, wherein $R^{12}$ is H or methyl, $R^{13}$ is methyl or trifluoromethyl, and $R^{14}$ is H or methyl, or Z is a 9-membered bi-cyclic heteroaryl, optionally substituted on either ring by a halogen, cyano, $(C_1-C_4)$alkyl, halo$(C_1-C_4)$alkyl, $(C_1-C_4)$alkoxy, hydroxyl, hydroxy$(C_1-C_4)$alkyl- or aminocarbonyl group, wherein the 9-membered bi-cyclic heteroaryl is an optionally substituted indazolyl or pyrazolo[3,4-b]pyridinyl, bonded to the amino ($NR^1$/NH) moiety via a substitutable carbon ring atom of the 5-membered pyrazolyl ring moiety of the indazolyl or pyrazolo[3,4-b]pyridinyl group;

or a salt, particularly a pharmaceutically acceptable salt, thereof.

Specifically, the invention is directed to a compound according to Formula (I) wherein:

$R^1$ is H or —$CH_2CH_3$; particularly, $R^1$ is H;

$R^2$ is —$SR^a$ or —$SO_2R^a$, and $R^a$ is —$CH_3$, —$CH(CH_3)_2$, —$C(CH_3)_3$, —$CH_2CH_2OH$, —$C(CH_3)_2CH_2CH_2OH$, or tetrahydro-2H-pyran-4-yl;

$R^3$ is H, chloro, —$CH_2CH_3$, —$CH=CH_2$, —OH, —$OCH_3$, —$OCF_2H$, —$OCH(CH_3)_2$, —$OCH_2CH_3$, —$OCH_2CF_3$, —$OCH_2CH_2Cl$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OC(CH_3)_2CO_2CH_2CH_3$, cyclohexylmethyloxy-, or tetrahydro-2H-pyran-4-yloxy-; and Z is 2-methyl-4-hydroxy-phenyl, benzo[d]thiazol-5-yl or 5-fluoro-1H-indazol-3-yl, or Z is pyrazolyl, wherein $R^{12}$ is H or methyl, $R^{13}$ is methyl or trifluoromethyl, and $R^{14}$ is H or methyl, or a salt, specifically a pharmaceutically acceptable salt, thereof.

In another embodiment, the invention is directed to a compound according to Formula (I) wherein:

$R^1$ is H;

$R^2$ is —$SO_2R^a$, and $R^a$ is —$CH_3$, —$CH(CH_3)_2$, or —$C(CH_3)_3$;

$R^3$ is H, chloro, —$CH_2CH_3$, —$CH=CH_2$, —OH, —$OCH_3$, —$OCF_2H$, —$OCH(CH_3)_2$, —$OCH_2CH_3$, —$OCH_2CF_3$, —$OCH_2CH_2Cl$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OC(CH_3)_2CO_2CH_2CH_3$, cyclohexylmethyloxy-, or tetrahydro-2H-pyran-4-yloxy-; and Z is benzo[d]thiazol-5-yl or 5-fluoro-1H-indazol-3-yl, or Z is pyrazolyl, wherein $R^{12}$ is H or methyl, $R^{13}$ is methyl or trifluoromethyl, and $R^{14}$ is H or methyl;

or a salt, specifically a pharmaceutically acceptable salt, thereof.

More specifically, the invention is directed to a compound according to Formula (I) wherein:

$R^1$ is H;

$R^2$ is —$SR^a$ or —$SO_2R^a$, and $R^a$ is —$CH_3$, —$CH(CH_3)_2$, —$C(CH_3)_3$, —$CH_2CH_2OH$, —$C(CH_3)_2CH_2CH_2OH$, or tetrahydro-2H-pyran-4-yl;

$R^3$ is chloro, —$CH_2CH_3$, —$CH=CH_2$, —$CH=CHCH_2OH$, —$OCH=CH_2$, —$OCH=CH—CO_2H$, —$OCH=CH—CO_2CH_3$, —$OCH=CH—CONH_2$, —OH, —$OCH_3$, —$OCF_2H$, —$OCH(CH_3)_2$, —$OCH_2CH_3$, —$OCH_2CF_3$, —$OCH_2CH_2CH_3$, —$OCH_2CH_2Cl$, —$OCH_2CH_2Br$, —$OCH_2CH_2SCH_3$, —$OCH_2CH_2SO_2CH_3$, —$OCH_2CH_2SO_2CH(CH_3)_2$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OCH(CH_3)CO_2CH_3$, —$OCH_2CH(CH_3)OH$, —$OC(CH_3)_2CO_2CH_2CH_3$, —$OCH_2CO_2H$, —$OCH_2CONH_2$, —$OCH_2$-cyclohexyl, or —O-tetrahydro-2H-pyran-4-yl; and Z is 2-methyl-5-hydroxy-phenyl, 2-fluoro-4-chloro-phenyl, 3-methoxy-4-chloro-phenyl, 3-hydroxy-4-chloro-phenyl, benzo[d]thiazol-5-yl, 5-(trifluoromethyl)-1H-pyrazol-3-yl, 1,3,4-trimethyl-1H-pyrazol-5-yl, 4,5-dimethyl-1H-pyrazol-3-yl, 5-fluoro-1H-indazol-3-yl, 1H-indazol-6-yl or 3-methyl-1H-indazol-6-yl, or a salt, specifically a pharmaceutically acceptable salt, thereof.

The invention is further directed to a compound according to Formula (I) wherein:

$R^1$ is H;

$R^2$ is —$SO_2R^a$, and $R^a$ is —$CH_3$, —$CH(CH_3)_2$, or —$C(CH_3)_3$, or $R^a$ is —$CH_2CH_2OH$ or —$C(CH_3)_2CH_2CH_2OH$;

$R^3$ is chloro, —$CH_2CH_3$, —$CH=CH_2$, —$CH=CHCH_2OH$, —$OCH=CH_2$, —$OCH=CH—CO_2H$, —$OCH=CH—CO_2CH_3$, —$OCH=CH—CONH_2$, —OH, —$OCH_3$, —$OCF_2H$, —$OCH(CH_3)_2$, —$OCH_2CH_3$, —$OCH_2CF_3$, —$OCH_2CH_2CH_3$, —$OCH_2CH_2Cl$, —$OCH_2CH_2Br$, —$OCH_2CH_2SCH_3$, —$OCH_2CH_2SO_2CH_3$, —$OCH_2CH_2SO_2CH(CH_3)_2$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OCH(CH_3)CO_2CH_3$, —$OCH_2CH(CH_3)OH$, —$OC(CH_3)_2CO_2CH_2CH_3$, —$OCH_2CO_2H$, —$OCH_2CONH_2$, —$OCH_2$-cyclohexyl, or —O-tetrahydro-2H-pyran-4-yl; and Z is benzo[d]thiazol-5-yl, 5-(trifluoromethyl)-1H-pyrazol-3-yl, 1,3,4-trimethyl-1H-pyrazol-5-yl, 4,5-dimethyl-1H-pyrazol-3-yl, 5-fluoro-1H-indazol-3-yl, 1H-indazol-6-yl or 3-methyl-1H-indazol-6-yl, or a salt, specifically a pharmaceutically acceptable salt, thereof.

Representative compounds of this invention include the compounds of Examples 1-80, specifically:
4-methyl-3-{[6-(methylthio)-4-quinazolinyl]amino}phenol,
4-methyl-3-{[6-(methylsulfonyl)-4-quinazolinyl] amino}phenol,
N-1,3-benzothiazol-5-yl-6-[(1,1-dimethylethyl)thio]-4-quinazolinamine,
N-1,3-benzothiazol-5-yl-6-[(1,1-dimethylethyl)sulfonyl]-4-quinazolinamine,
6-(tert-butylsulfonyl)-N-(5-fluoro-1H-indazol-3-yl)quinazolin-4-amine,
N-1,3-benzothiazol-5-yl-6-[(1-methylethyl)sulfonyl]-4-quinazolinamine,
2-{[4-(1,3-benzothiazol-5-ylamino)-6-quinazolinyl] sulfonyl}ethanol,
N-1,3-benzothiazol-5-yl-6-(tetrahydro-2H-pyran-4-ylsulfonyl)-4-quinazolinamine,
N-1,3-benzothiazol-5-yl-6-(tetrahydro-2H-pyran-4-ylsulfonyl)-4-quinazolinamine,
2-((4-((4,5-dimethyl-1H-pyrazol-3-yl)amino)-7-methoxyquinazolin-6-yl)sulfonyl)ethanol,
N-(5-fluoro-1H-indazol-3-yl)-6-[(1-methylethyl)sulfonyl]-4-quinazolinamine,
N-(4,5-dimethyl-1H-pyrazol-3-yl)-6-[(1-methylethyl)sulfonyl]-4-quinazolinamine,
6-(tert-butylsulfonyl)-N-(5-(trifluoromethyl)-1H-pyrazol-3-yl)quinazolin-4-amine,
6-(tert-butylsulfonyl)-N-(1,3,4-trimethyl-1H-pyrazol-5-yl) quinazolin-4-amine,
N-(6-(tert-butylthio)-7-methoxyquinazolin-4-yl)benzo[d] thiazol-5-amine,
N-(6-(tert-butylsulfonyl)-7-methoxyquinazolin-4-yl)benzo [d]thiazol-5-amine,
N-(6-(isopropylsulfonyl)-7-methoxyquinazolin-4-yl)benzo [d]thiazol-5-amine,
4-(benzo[d]thiazol-5-ylamino)-6-(tert-butylsulfonyl)quinazolin-7-ol,
N-(6-(tert-butylsulfonyl)-7-ethoxyquinazolin-4-yl)benzo[d] thiazol-5-amine,
N-(6-(tert-butylsulfonyl)-7-ethoxy quinazolin-4-yl)-N-ethylbenzo[d]thiazol-5-amine,
2-((4-(benzo[d]thiazol-5-ylamino)-6-(tert-butylsulfonyl) quinazolin-7-yl)oxy)ethanol,
N-(6-(tert-butylsulfonyl)-7-(difluoromethoxy)quinazolin-4-yl)benzo[d]thiazol-5-amine,
N-(6-(tert-butylsulfonyl)-7-(2,2,2-trifluoroethoxy)quinazolin-4-yl)benzo[d]thiazol-5-amine,
N-(6-(tert-butylsulfonyl)-7-(methoxymethoxy)quinazolin-4-yl)benzo[d]thiazol-5-amine,
N-(6-(tert-butylsulfonyl)-7-(cyclohexylmethoxy)quinazolin-4-yl)benzo[d]thiazol-5-amine,
3-((4-(benzo[d]thiazol-5-ylamino)-6-(tert-butylsulfonyl) quinazolin-7-yl)oxy)propan-1-ol,
N-(6-(tert-butylsulfonyl)-7-((tetrahydro-2H-pyran-4-yl) oxy)quinazolin-4-yl)benzo[d]thiazol-5-amine,
N-(6-(tert-butylsulfonyl)-7-(2-chloroethoxy)quinazolin-4-yl)benzo[d]thiazol-5-amine,
(R)-1-((4-(benzo[d]thiazol-5-ylamino)-6-(tert-butylsulfonyl)quinazolin-7-yl)oxy)propan-2-ol,
N-(6-(tert-butylsulfonyl)-7-propoxyquinazolin-4-yl)benzo [d]thiazol-5-amine,
N-(6-(tert-butylsulfonyl)-7-(2-(methylthio)ethoxy)quinazolin-4-yl)benzo[d]thiazol-5-amine,
N-(7-(2-bromoethoxy)-6-(tert-butylsulfonyl)quinazolin-4-yl)benzo[d]thiazol-5-amine,
4-(benzo[d]thiazol-5-ylamino)-6-(tert-butylthio)quinazolin-7-ol,
N-(6-(tert-butylthio)-7-isopropoxyquinazolin-4-yl)benzo[d] thiazol-5-amine,
N-(6-(tert-butylsulfonyl)-7-isopropoxyquinazolin-4-yl) benzo[d]thiazol-5-amine,
ethyl 2-((4-(benzo[d]thiazol-5-ylamino)-6-(tert-butylsulfonyl)quinazolin-7-yl)oxy)-2-methylpropanoate,
2-((4-(benzo[d]thiazol-5-ylamino)-6-(tert-butylsulfonyl) quinazolin-7-yl)oxy)-2-methylpropan-1-ol,
N-1,3-benzothiazol-5-yl-6-[(1,1-dimethylethyl)sulfonyl]-7-ethenyl-4-quinazolinamine,
N-1,3-benzothiazol-5-yl-6-[(1,1-dimethylethyl)sulfonyl]-7-ethyl-4-quinazolinamine,
N-(6-(tert-butylsulfonyl)-7-chloroquinazolin-4-yl)benzo[d] thiazol-5-amine,
6-(tert-butylsulfonyl)-7-chloro-N-(4,5-dimethyl-1H-pyrazol-3-yl)quinazolin-4-amine,
6-[(1,1-dimethylethyl)sulfonyl]-N-(5-fluoro-1H-pyrazolo [3,4-b]pyridin-3-yl)-7-(methyloxy)-4-quinazolinamine,
6-(tert-butylsulfonyl)-N-(4-chloro-3-methoxyphenyl)-7-methoxyquinazolin-4-amine,
5-((6-(tert-butylsulfonyl)-7-methoxyquinazolin-4-yl) amino)-2-chlorophenol,
6-(tert-butylsulfonyl)-7-methoxy-N-(3-methyl-1H-indazol-6-yl)quinazolin-4-amine,
6-(tert-butylsulfonyl)-N-(4-chloro-2-fluorophenyl)-7-methoxyquinazolin-4-amine,
6-(tert-butylsulfonyl)-N-(1H-indazol-6-yl)-7-methoxyquinazolin-4-amine,
6-(tert-butylsulfonyl)-N-(4,5-dimethyl-1H-pyrazol-3-yl)-7-methoxyquinazolin-4-amine,
(E)-3-(4-(benzo[d]thiazol-5-ylamino)-6-(tert-butylsulfonyl) quinazolin-7-yl)prop-2-en-1-ol,
2-((4-(benzo[d]thiazol-5-ylamino)-7-methoxyquinazolin-6-yl)sulfonyl)ethanol,
(R)-methyl 2-((4-(benzo[d]thiazol-5-ylamino)-6-(tert-butylsulfonyl)quinazolin-7-yl)oxy)propanoate,
(S)-methyl 2-((4-(benzo[d]thiazol-5-ylamino)-6-(tert-butylsulfonyl)quinazolin-7-yl)oxy)propanoate,
methyl 2-((4-(benzo[d]thiazol-5-ylamino)-6-(tert-butylsulfonyl)quinazolin-7-yl)oxy)propanoate,
(R)-2-((4-(benzo[d]thiazol-5-ylamino)-6-(tert-butylsulfonyl)quinazolin-7-yl)oxy)propan-1-ol,
(S)-2-((4-(benzo[d]thiazol-5-ylamino)-6-(tert-butylsulfonyl)quinazolin-7-yl)oxy)propan-1-ol,
2-((4-(benzo[d]thiazol-5-ylamino)-6-(tert-butylsulfonyl) quinazolin-7-yl)oxy)propan-1-ol,
6-(tert-butylsulfonyl)-4-((4-chloro-2-fluorophenyl)amino) quinazolin-7-ol,
N-(6-(tert-butylsulfinyl)-7-methoxyquinazolin-4-yl)benzo [d]thiazol-5-amine,
2-((4-(benzo[d]thiazol-5-ylamino)-6-(tert-butylsulfonyl) quinazolin-7-yl)oxy)acetamide,
2-((4-(benzo[d]thiazol-5-ylamino)-6-(tert-butylsulfonyl) quinazolin-7-yl)oxy)acetic acid,
N-(6-(tert-butylsulfonyl)-7-(2-(methylsulfonyl)ethoxy)quinazolin-4-yl)benzo[d]thiazol-5-amine,
N-(6-(tert-butylsulfonyl)-7-(2-(isopropylsulfonyl)ethoxy) quinazolin-4-yl)benzo[d]thiazol-5-amine,
(E)-methyl 3-((4-(benzo[d]thiazol-5-ylamino)-6-(tert-butylsulfonyl)quinazolin-7-yl)oxy)acrylate,
(E)-3-((4-(benzo[d]thiazol-5-ylamino)-6-(tert-butylsulfonyl)quinazolin-7-yl)oxy)acrylamide,
(E)-3-((4-(benzo[d]thiazol-5-ylamino)-6-(tert-butylsulfonyl)quinazolin-7-yl)oxy)acrylic acid, N-(6-(tert-butylsulfonyl)-7-(vinyloxy)quinazolin-4-yl)
benzo[d]thiazol-5-amine,
4-(benzo[d]thiazol-5-ylamino)-7-methoxy-N,N-dimethylquinazoline-6-sulfonamide,
4-(benzo[d]thiazol-5-ylamino)-N-isopropyl-7-methoxyquinazoline-6-sulfonamide,
N-(7-methoxy-6-(pyrrolidin-1-ylsulfonyl)quinazolin-4-yl)
benzo[d]thiazol-5-amine,
N-(7-methoxy-6-(morpholinosulfonyl)quinazolin-4-yl)
benzo[d]thiazol-5-amine,
4-(benzo[d]thiazol-5-ylamino)-N-(2-hydroxyethyl)-7-methoxyquinazoline-6-sulfonamide,
4-(benzo[d]thiazol-5-ylamino)-7-methoxy-N-(tetrahydro-2H-pyran-4-yl)quinazoline-6-sulfonamide,
4-(benzo[d]thiazol-5-ylamino)-N-(2-hydroxy-2-methylpropyl)-7-methoxyquinazoline-6-sulfonamide,
1-((4-(benzo[d]thiazol-5-ylamino)-7-methoxyquinazolin-6-yl)sulfonyl)pyrrolidin-3-ol,
4-(benzo[d]thiazol-5-ylamino)-N-(2-hydroxypropyl)-7-methoxyquinazoline-6-sulfonamide,
4-(benzo[d]thiazol-5-ylamino)-7-methoxy-N-(2-methoxyethyl)quinazoline-6-sulfonamide,
4-(benzo[d]thiazol-5-ylamino)-7-methoxy-N-(oxetan-3-yl)
quinazoline-6-sulfonamide,
4-(benzo[d]thiazol-5-ylamino)-N-(2-(dimethylamino)
ethyl)-7-methoxyquinazoline-6-sulfonamide,
1-((4-(benzo[d]thiazol-5-ylamino)-7-methoxyquinazolin-6-yl)sulfonyl)pyrrolidine-2-carboxylic acid,
1-(4-((4-(benzo[d]thiazol-5-ylamino)-7-methoxyquinazolin-6-yl)sulfonyl)piperazin-1-yl)ethanone,
N-(2-(1H-tetrazol-5-yl)ethyl)-4-(benzo[d]thiazol-5-ylamino)-7-methoxyquinazoline-6-sulfonamide,
4-(benzo[d]thiazol-5-ylamino)-7-methoxy-N-((tetrahydro-2H-pyran-4-yl)methyl)quinazoline-6-sulfonamide,
or a salt, particularly a pharmaceutically acceptable salt, thereof.

Specifically, this invention is directed to N-1,3-benzothiazol-5-yl-6-[(1,1-dimethylethyl)sulfonyl]-4-quinazolinamine or a salt, particularly a pharmaceutically acceptable salt, thereof.

This invention is also directed to N-1,3-benzothiazol-5-yl-6-[(1-methylethyl)sulfonyl]-4-quinazolinamine, or a salt, particularly a pharmaceutically acceptable salt, thereof.

This invention is further directed to N-(6-(tert-butylsulfonyl)-7-methoxyquinazolin-4-yl)benzo[d]thiazol-5-amine or a salt, particularly a pharmaceutically acceptable salt, thereof.

Specifically, this invention is directed to 2-((4-(benzo[d]thiazol-5-ylamino)-6-(tert-butylsulfonyl)quinazolin-7-yl)oxy)ethanol or a salt, particularly a pharmaceutically acceptable salt, thereof.

Accordingly, a compound of the invention includes a compound of Formula (I), or a salt thereof, particularly a pharmaceutically acceptable salt thereof.

Accordingly, a compound of the invention includes a compound of Formula (I), particularly the specific compounds described herein, or a salt thereof, particularly a pharmaceutically acceptable salt thereof. In one embodiment, the invention is directed to a method of inhibiting RIP2 kinase comprising contacting a cell with a compound of the invention. In another embodiment, the invention is directed to a method of treating a RIP2 kinase-mediated disease or disorder comprising administering a therapeutically effective amount of a compound of the invention to a human in need thereof. The invention is still further directed to the use of a compound of the invention or a pharmaceutical composition comprising a compound of the invention to inhibit RIP2 kinase and/or treat a RIP2 kinase-mediated disease or disorder.

The compounds according to Formula (I) may contain one or more asymmetric center (also referred to as a chiral center) and may, therefore, exist as individual enantiomers, diastereomers, or other stereoisomeric forms, or as mixtures thereof. Chiral centers, such as a chiral carbon, or particularly, a chiral —SO— moiety, may also be present in the compounds of this invention. Where the stereochemistry of a chiral center present in a compound of this invention (e.g., compound name) or in any chemical structure illustrated herein is not specified, the compound, compound name, or structure is intended to encompass all individual stereoisomers and all mixtures thereof. Thus, compounds according to Formula (I) containing one or more chiral center may be present as racemic mixtures, enantiomerically enriched mixtures, or as enantiomerically pure individual stereoisomers. For example, each of (R)—N-(6-(tert-butylsulfinyl)-7-methoxyquinazolin-4-yl)benzo[d]thiazol-5-amine and (S)—N-(6-(tert-butylsulfinyl)-7-methoxyquinazolin-4-yl)benzo[d]thiazol-5-amine are encompassed by the chemical name N-(6-(tert-butylsulfinyl)-7-methoxyquinazolin-4-yl)benzo[d]thiazol-5-amine.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula (I) are preferably pharmaceutically acceptable salts. Suitable pharmaceutically acceptable salts include those described by Berge, Bighley and Monkhouse J. Pharm. Sci (1977) 66, pp 1-19. Salts encompassed within the term "pharmaceutically acceptable salts" refer to non-toxic salts of the compounds of this invention.

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfate, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention into another pharmaceutically acceptable salt of a compound of this invention.

For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates, particularly hydrates. It is to be understood that the term "a salt, particularly a pharmaceutically acceptable salt, thereof, or hydrate thereof" encompasses a salt of a compound of Formula (I), a pharmaceutically acceptable salt of a compound of Formula (I), a hydrate of a compound of Formula (I), a hydrate of a salt of a compound of Formula (I), and a hydrate of a pharmaceutically acceptable salt of a compound of Formula (I).

Because the compounds of Formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Synthetic Methods

The compounds of Formula (I) may be obtained by using synthetic procedures illustrated in the Schemes below or by drawing on the knowledge of a skilled organic chemist. The syntheses provided in these Schemes are applicable for producing compounds of the invention having a variety of different substituent groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula (I), they are illustrative of processes that may be used to make the compounds of the invention.

Intermediates (compounds used in the preparation of the compounds of the invention) may also be present as salts. Thus, in reference to intermediates, the phrase "compound (s) of formula (number)" means a compound having that structural formula or a pharmaceutically acceptable salt thereof.

4-Chloroquinazoline intermediates may be from the appropriately functionalized nitrobenzoic acid via reduction of the nitro group to an aniline followed by condensation with formamide or formimamide and cyclization to the 4-quinazolinone. Conversion to the chloroquinazoline could be accomplished with POCl₃ or SOCl₂ at elevated temperatures.

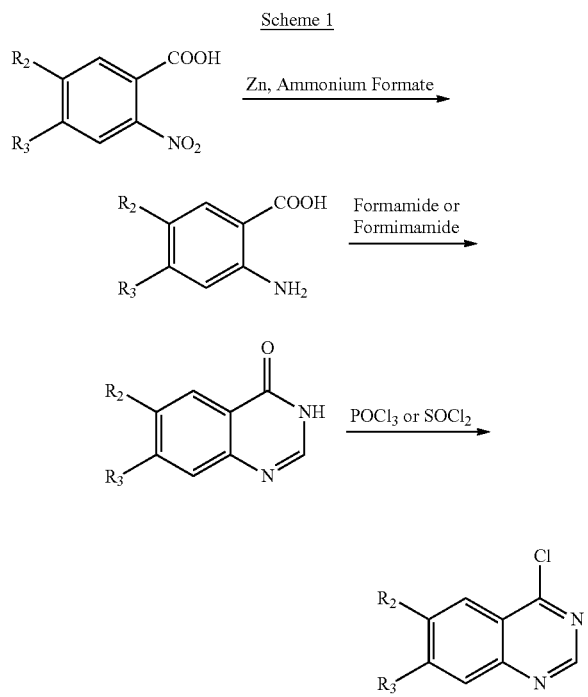

Additional starting anilines may be synthesized via benzoic acids by protecting the acid as an ester followed by halogenation. Reaction with formimamide then provides the quinazolinone which could then be converted to the 4-chloroquinazoline as in Scheme 1.

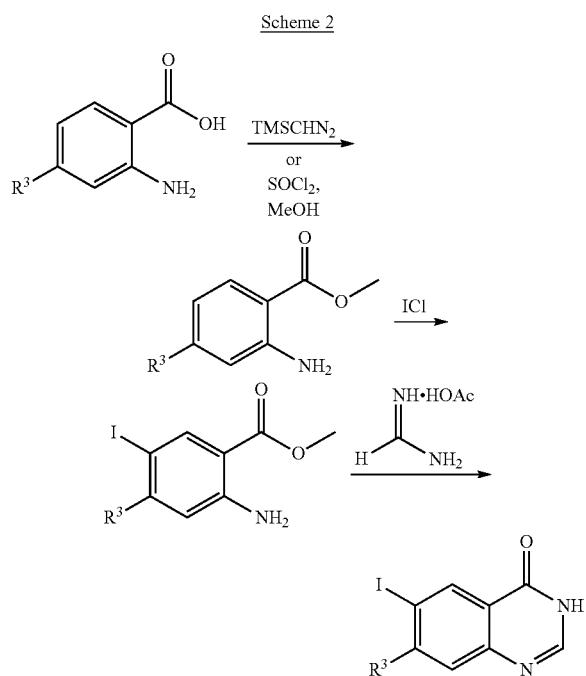

Palladium catalyzed coupling of the iodoquinazolines with thiols may provide 6-alkylthioquinazolines which could be final products, or further subjected to oxidation with Oxone to afford the corresponding sulfone final products. Sulfoxides may also be obtained by this route through carefully monitoring the reaction. Additionally, any sulfides at $R^3$ may be oxidized to sulfones in this manner.

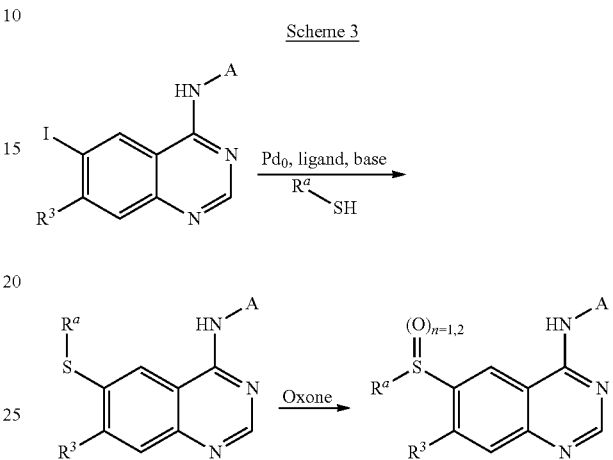

Substitution at C6 could also be installed prior to installation of the "A" moiety. A palladium catalyzed coupling of a thiol with the 6-iodoquinazolinone can provide a sulfide which can subsequently be oxidized to the sulfone. Chlorination with POCl₃ or SOCl₂ may provide the 4-chloroquinazoline.

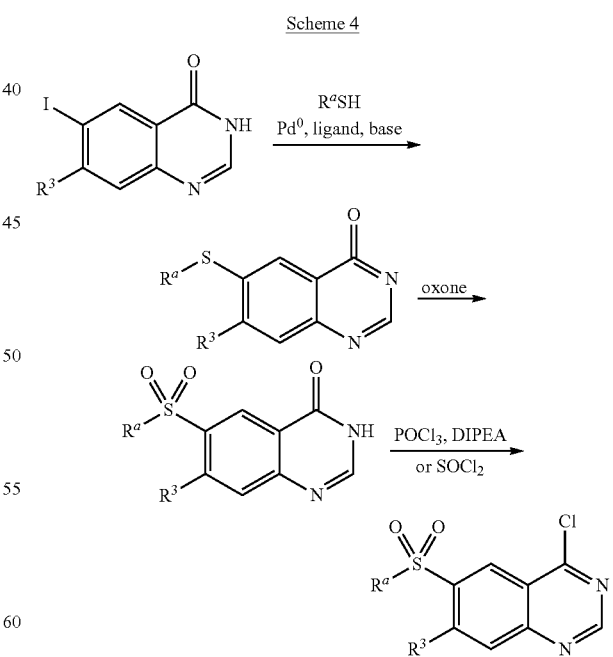

Anilines/amines could be reacted with 4-chloro-quinazolines under basic or acidic conditions to afford 4-aminoquinazolines which could be final compounds or used as intermediates for further synthesis.

Scheme 5

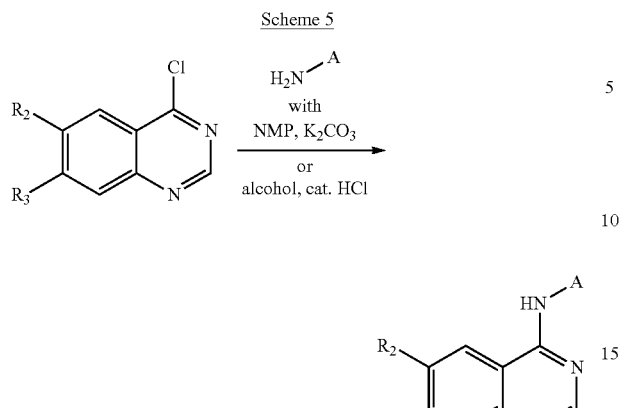

7-Hydroxyquinazolines could be synthesized by dealkylation of the 7-methoxyquinazolines with a sodium alkylthiolate.

Scheme 6

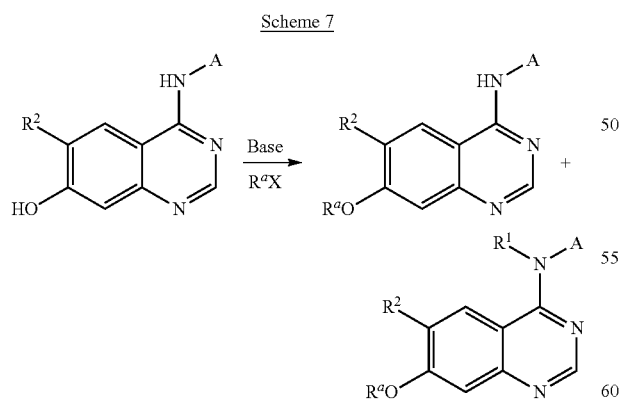

Additional alkoxy substitution at C7 can be installed by alkylation of the 7-hydroxyquinazoline. In some cases, alkylation of the secondary amine may be observed. When Boc-protected haloalkylamines are used, a subsequent step with treatment of HCl is necessary to remove the Boc protecting group.

Scheme 7

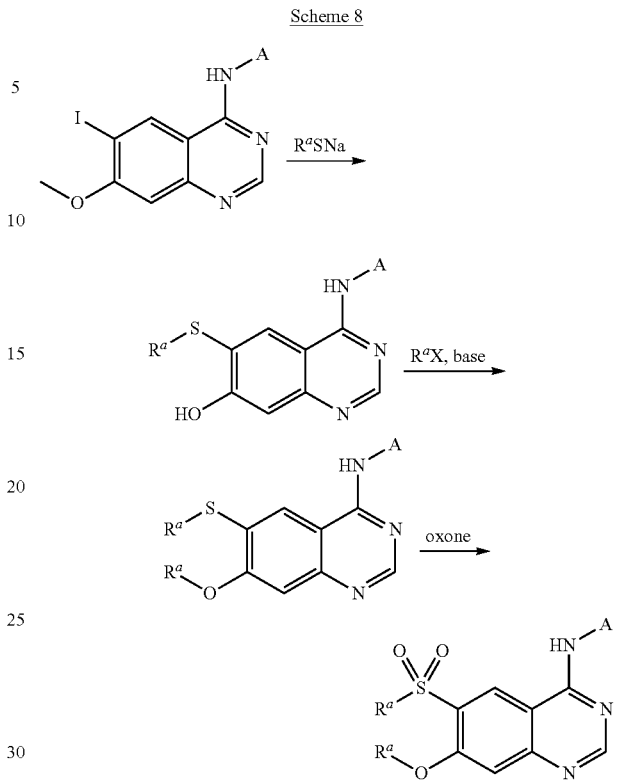

In select cases, the sulfide at C6 could be installed while dealkylating C7 methoxyquinazoline with the appropriate sodium alkylthiolate. Final product may be obtained following alkylation of the resultant C7 hydroxyl and oxidation to the sulfone.

Scheme 8

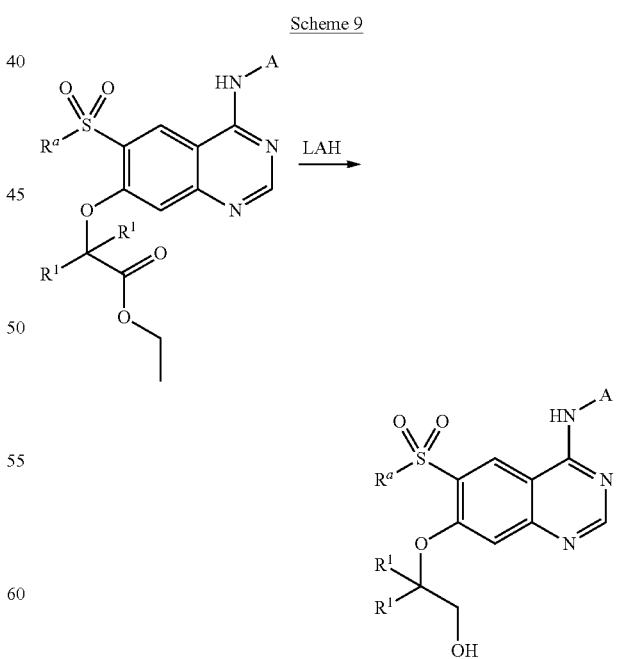

Substituted hydroxyethyl chains at C7 could be accessed through reduction of an ester that was installed as in Scheme 8.

Scheme 9

The 7-ethylquinazoline could synthesized via a Stille coupling with the C7 triflate to provide the ethylenebenezene followed by hydrogenolysis.

Scheme 10

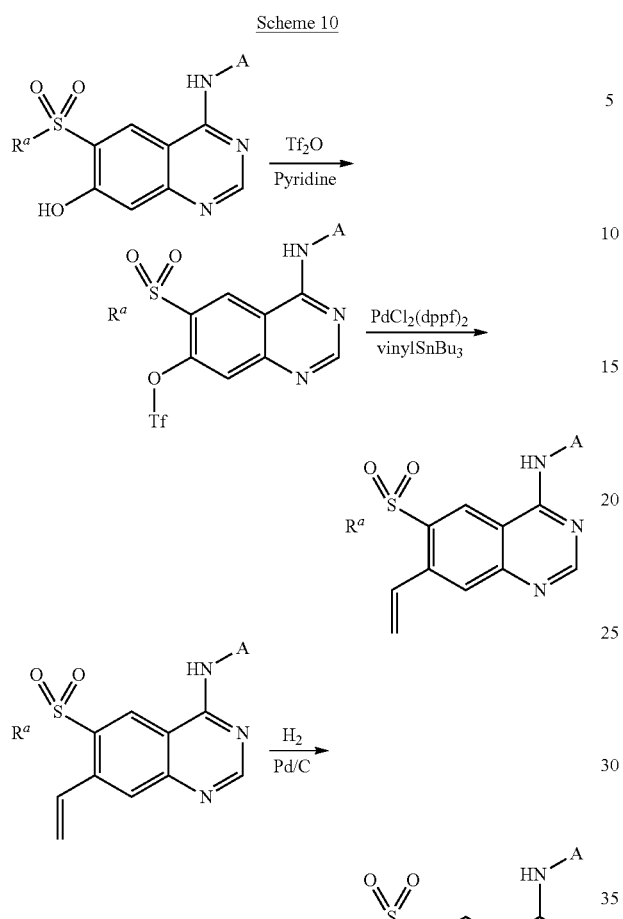

Alternatively, the triflate can undergo a palladium catalyzed reaction to install the allylic alcohol.

Scheme 11

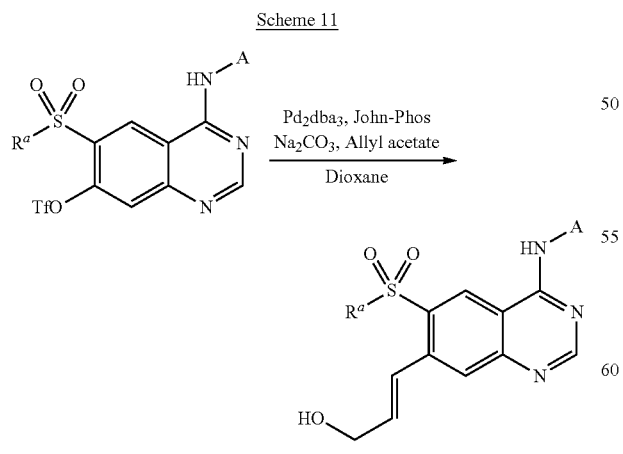

5-Fluoro-1H-pyrazolo[3,4-b]pyridin-3-amine may be synthesized from 2-chloro-5-fluoro-3-pyridinecarboxylic acid. Formation of the acylchloride followed by the addition of ammonia can provide the amide which may be subsequently converted to the nitrile. Treatment with hydrazine may provide the azaindazole.

Scheme 12

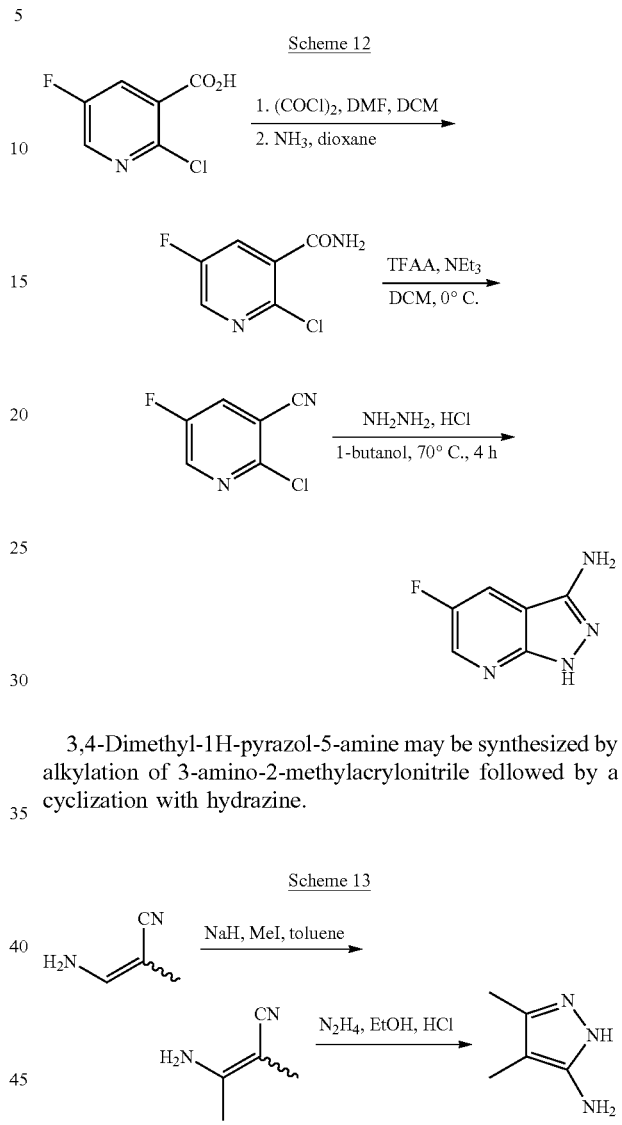

3,4-Dimethyl-1H-pyrazol-5-amine may be synthesized by alkylation of 3-amino-2-methylacrylonitrile followed by a cyclization with hydrazine.

Scheme 13

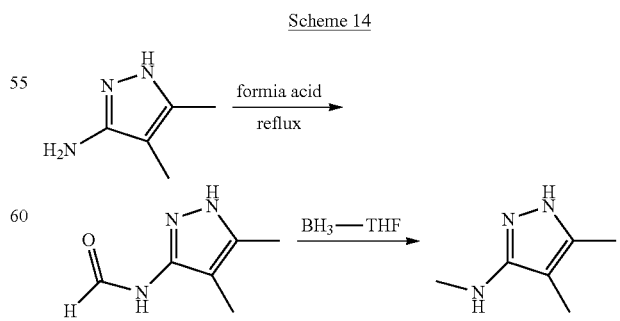

The pyrazolamine can be further methylated by reaction with formic acid followed by reduction with borohydride.

Scheme 14

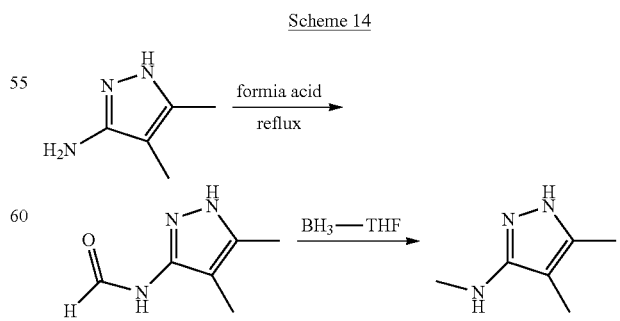

"A" groups may be installed via a C4 sulfide intermediate. Treatment of the 4-chloro-7-methoxyquinazolines with sodium ethanethiolate provides the 4-ethylsulfide-7-hydroxyquinoazolines. These 4-alkythio-quinazoline intermediates may be directly treated with an excess of amine (A-NH$_2$) under acidic microwave conditions to provide final products. Alternatively, the intermediates could be alkylated at R$^3$ to afford the hydroxyethyl ethers before undergoing reaction with amine (A-NH$_2$).

Scheme 15

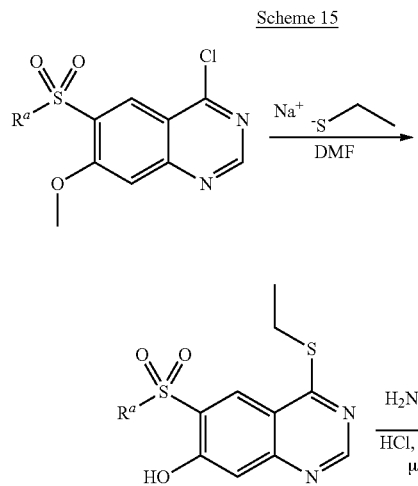

Hydrolysis of esters to carboxylic acids (on R$^3$ side chains) may be accomplished with LiOH (X=any alkyl chain).

Scheme 16

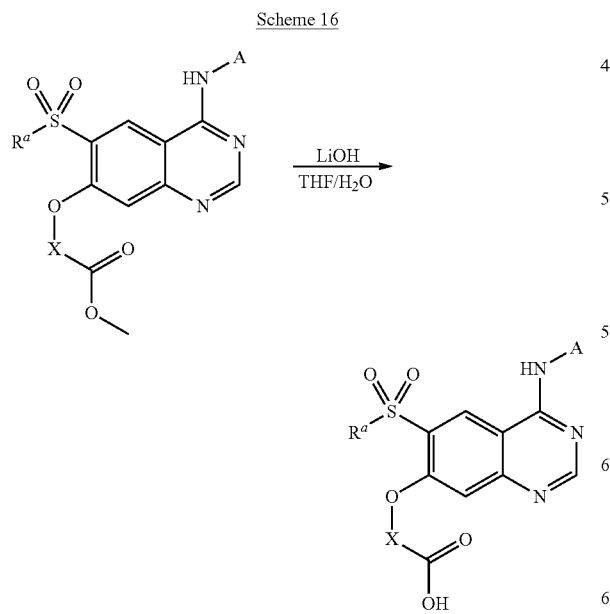

Direct reaction of a R$^3$ phenol with acrylate provides an unsaturated ester.

Scheme 17

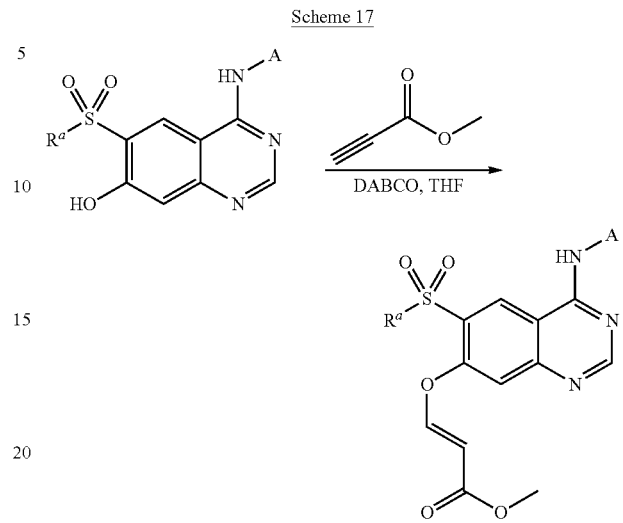

Elimination of an alkyl bromide under thermal conditions provides a vinyl ether.

Scheme 18

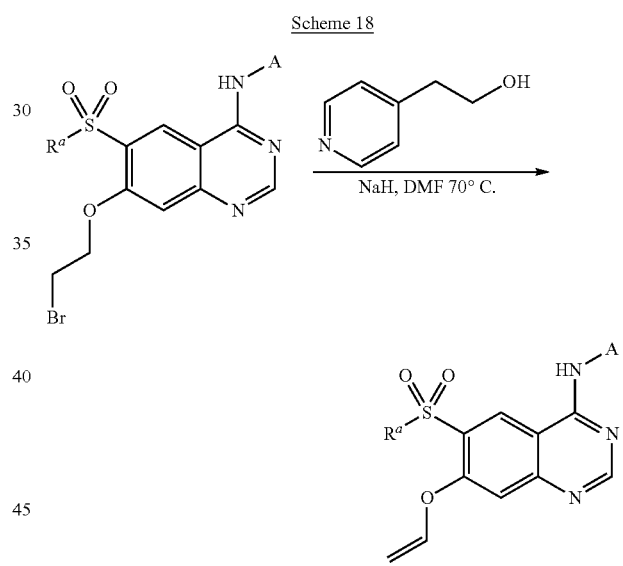

Sulfonamides may be obtained through the sulfonyl chloride. Formation of the benzylthioether via a palladium catalyzed reaction at the 6-iodoquinazoline followed by treatment with NCS under acidic conditions provided the sulfonyl chloride. Treatment with an amine or ammonia affords the sulfonamide.

Scheme 19

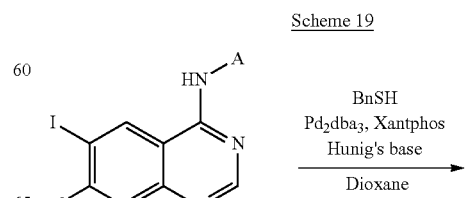

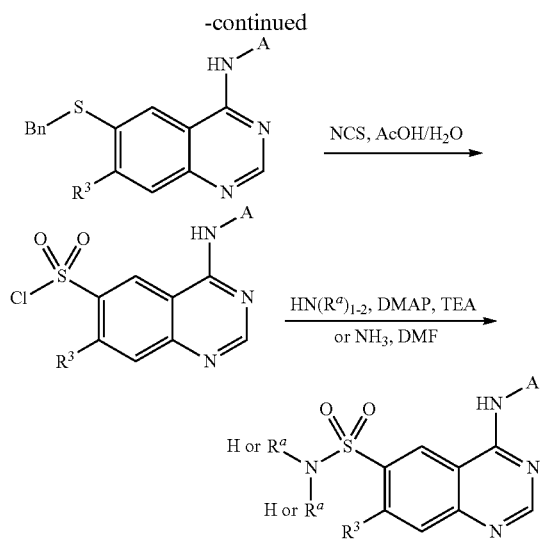

The compounds of this invention may be particularly useful for treatment of RIP2 kinase-mediated diseases or disorders, particularly, uveitis, interleukin-1 converting enzyme (ICE, also known as Caspase-1) associated fever syndrome, dermatitis, acute lung injury, type 2 diabetes mellitus, arthritis (specifically rheumatoid arthritis), inflammatory bowel disorders (such as ulcerative colitis and Crohn's disease), early-onset and extra-intestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

The compounds of this invention may be particularly useful in the treatment of uveitis, ICE fever, Blau Syndrome, early-onset sarcoidosis, ulcerative colitis, Crohn's disease, Wegener's granulamatosis and sarcoidosis.

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

For example, the compounds of this invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include corticosteroids, particularly low-dose corticosteroids (such as Deltasone® (prednisone)) and anti-inflammatory biologics (such as Acterma® (anti-IL6R mAb) and Rituximab® (anti-CD20 mAb)). Examples of suitable anti-TNF agents include anti-TNF biologics (such as Enbrel® (etanecerpt)), Humira® (adalimumab), Remicade® (infliximab) and Simponi® (golimumab)).

This invention also provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein; more specifically, for use in the treatment of a disease mediated by inhibition of RIP2 kinase.

The invention also provides for the use of a compound of Formula (I), or a salt thereof, particularly a pharmaceutically acceptable salt thereof, in the manufacture of a medicament for use in the treatment of a RIP2 kinase-mediated disease or disorder, for example the diseases and disorders recited herein.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate or inhibit the activity of RIP2 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a mediated disease or disorder. Specific diseases and disorders that may be particularly susceptible to treatment using a compound of this invention are described herein.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

For use in therapy, the compounds of the invention will be normally, but not necessarily, formulated into a pharmaceutical composition prior to administration to a patient. Accordingly, the invention also is directed to pharmaceutical compositions comprising a compound of the invention and a pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). For example, deuterated pyrazole alkyl groups or deuterated alkyl-thioquinazolines or alkyl-sulfonylquinazolines may be prepared by conventional techniques (see for example: according to the method of Preparation 7 using iodomethane-d$_3$, available from Aldrich Chemical Co., Milwaukee, Wis., Cat. No. 176036, or the method of Scheme 13 using methane-d$_3$-thiol, Cat. No. 614904, respectively). Employing such compounds will allow for the preparation of compounds of Formula (I) in which various hydrogen atoms are replaced with deuterium atoms. Halogen substitution on the quinazoline core may also be converted the deuterated form via a lithium halogen exchange followed by a quench with MeOH-d$_4$.

Names for the intermediate and final compounds described herein were generated using the software naming program ACD/Name Pro V6.02 available from Advanced Chemistry Development, Inc., 110 Yonge Street, 14$^{th}$ Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com). It will be appreciated by those skilled in the art that each naming program may generate a different name for the same structurally depicted chemical group/moiety, e.g.,

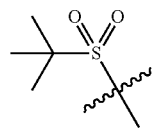 [SMILES: *S(=O)(=O)C(C)(C)C]

may be named as a tert-butylsulfonyl or as a (1,1-dimethylethyl)sulfonyl group/moiety. In addition, it will be appreciated by those skilled in the art that in certain instances this program will name a structurally depicted compound as a tautomer of that compound. It is to be understood that any reference to a named compound or a structurally depicted compound is intended to encompass all tautomers of such compounds and any mixtures of tautomers thereof.

In the following experimental descriptions, the following abbreviations may be used:

| Abbreviation | Meaning |
|---|---|
| AcOH | acetic acid |
| aq | aqueous |
| brine | saturated aqueous sodium chloride |
| CH$_2$Cl$_2$ or DCM | methylene chloride |
| CH$_3$CN or MeCN | acetonitrile |
| CH$_3$NH$_2$ | methylamine |
| d | day |
| DCE | 1,2-dichloroethane |
| DMF | N,N-dimethylformamide |
| DMSO | dimethylsulfoxide |
| EDC | 1-ethyl-3-(3-dimethylaminopropyl) carbodiimide |
| equiv | equivalents |
| Et | ethyl |
| Et$_3$N or TEA | triethylamine |
| Et$_2$O | diethyl ether |
| EtOAc | ethyl acetate |
| h, hr | hour(s) |
| HATU | O-(7-Azabenzotriazol-1yl)-N,N,N',N'-tetramethylyronium hexafluorophosphate |
| HCl | hydrochloric acid |
| ICl | iodine monochloride |
| i-Pr$_2$NEt | N',N'-diisopropylethylamine |
| KOt-Bu | potassium tert-butoxide |
| LCMS | liquid chromatography-mass spectroscopy |
| LiHDMS | lithium hexamethyldisilazide |
| Me | methyl |
| MeOH or CH$_3$OH | methanol |
| MgSO$_4$ | magnesium sulfate |
| min | minute(s) |
| MS | mass spectrum |
| µw | microwave |
| NaBH$_4$ | sodium borohydride |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| N$_2$H$_2$ | hydrazine |
| NH$_4$Cl | ammonium chloride |
| NiCl$_2$•6H$_2$O | nickel (II) chloride hexahydrate |
| NMP | N-methyl-2-pyrrolidone |
| Ph | phenyl |
| POCl$_3$ | phosphoryl chloride |
| rt | room temperature |
| satd. | saturated |
| SPE | solid phase extraction |
| TFA | trifluoroacetic acid |
| THF | tetrahydrofuran |
| t$_R$ | retention time |

Preparation 1

6-(methylthio)-4(1H)-quinazolinone

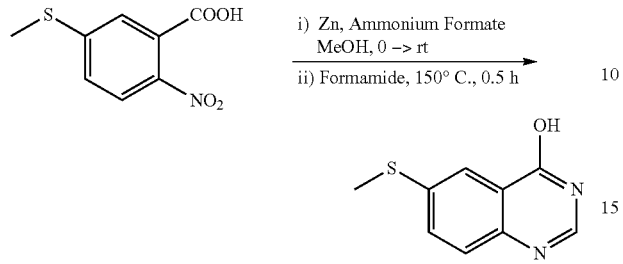

5-(Methylthio)-2-nitrobenzoic acid (1.0 g, 4.7 mmol), zinc (1.8 g, 28 mmol), and MeOH (38 mL) were purged with nitrogen for 10 min and cooled to 0° C. Ammonium formate (2.96 g, 46.9 mmol) was added in several portions and the reaction was left to stir at rt overnight. After 18 h, the milky-white reaction was diluted with acetone and filtered. The solid was collected and placed in a round bottom flask with formamide (9.35 mL, 235 mmol). The reaction was heated to 150° C. for 30 min. After cooling to rt, the mixture was partitioned between satd. NaHCO$_3$ and Et$_2$O. The aqueous layer was extracted with Et$_2$O (5×). The combined organic portions were dried over MgSO$_4$ and concentrated to yield 350 mg of crude product which was dry-loaded onto silica and purified via column chromatography (Biotage SP-1, 100% EtOAc) to afford 120 mg of pure material. The aqueous layer was extracted again with 15% MeOH/EtOAc (3×). The combined organic portions were dried over MgSO$_4$ and concentrated to yield 4 g of formamide and desired product. The crude product was dry-loaded onto silica and purified via column chromatography (Biotage SP-1, 100% EtOAc) which removed the ~35% of the formamide. Chromatography was repeated (2×) to yield pure product (100 mg) which was combined with the earlier 120 mg to provide 6-(methylthio)-4(1H)-quinazolinone (215 mg, 1.12 mmol, 23.9% yield). MS (m/z) 193 (M+H$^+$); $^1$H NMR (400 MHz, DMSO-d$_6$) δ 12.29 (br. s., 1H), 8.05 (s, 1H), 7.85 (d, J=2.3 Hz, 1H), 7.67-7.74 (m, 1H), 7.56-7.63 (m, 1H), 2.57 (s, 3H)

Preparation 2

N-1,3-benzothiazol-5-yl-6-iodo-4-quinazolinamine

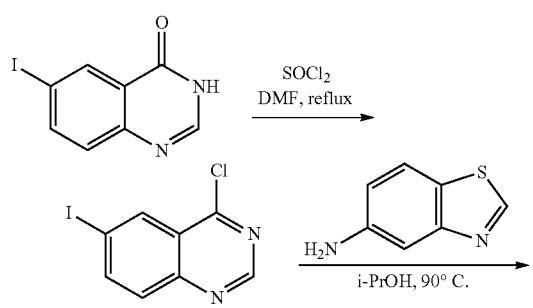

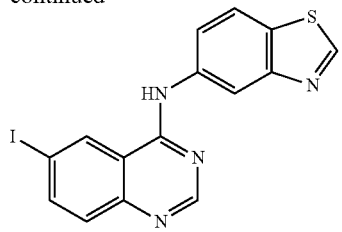

Step 1. 4-chloro-6-iodoquinazoline: 6-iodo-4(1H)-quinazolinone (10 g, 37 mmol) was weighed into a 250 mL flask. Thionyl chloride (100 mL, 1.4 mmol) and DMF (0.5 mL, 6.5 mmol) were added to give a grey suspension. The mixture was heated to reflux. Heating was continued for 6 h and then the mixture was cooled on ice bath for 1 h. A yellow solid precipitated and was collected by filtration to afford 8.6 g (77%) of the title compound.

Step 2. N-1,3-benzothiazol-5-yl-6-iodo-4-quinazolinamine: To a solution of 4-chloro-6-iodoquinazoline (2.60 g, 8.95 mmol) in isopropanol (60 mL) was added 1,3-benzothiazol-5-amine (1.479 g, 9.85 mmol). The mixture was then placed in oil bath preheated to 90° C. The reaction was complete in 30 min., and the solution was allowed to cool to room temperature. A yellow solid precipitated and was filtered and dried to provide 3.6 g (91%) of the title compound.

The following intermediate, N-(5-fluoro-1H-indazol-3-yl)-6-iodo-4-quinazolinamine, was made in the same manner:

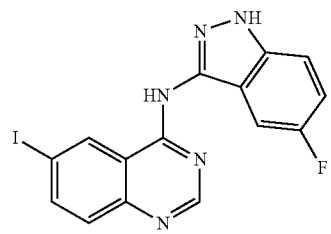 [SMILES: Fc1ccc2[nH]nc(Nc3ncnc4ccc(I)cc34)c2c1]

Preparation 3

4-chloro-6-[(1-methylethyl)sulfonyl]quinazoline

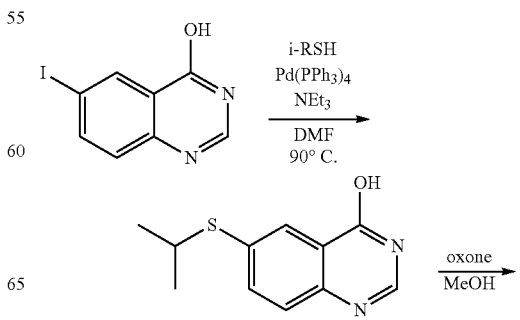

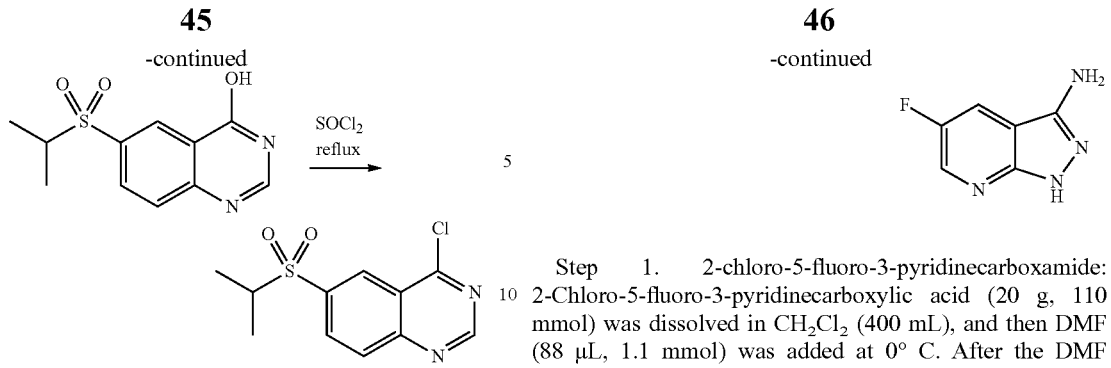

Step 1. 6-[(1-methylethyl)thio]-4(1H)-quinazolinone: To a solution of 6-iodo-4(1H)-quinazolinone (3.0 g, 11.0 mmol), 2-propanethiol (1.1 mL, 12.1 mmol) and Et₃N (4.6 mL, 33.1 mmol) in DMF (40 mL) was added Pd(Ph₃P)₄ (1.27 g, 1.10 mmol) under nitrogen. The solution was stirred at 90° C. for 1 h. The reaction mixture was allowed to cool to rt and DMF was removed in vacuo. The crude material was purified by column chromatography (0 to 5% MeOH/CH₂Cl₂) to provide 6-[(1-methylethyl)thio]-4(1H)-quinazolinone (1.8 g, 7.4 mmol, 67% yield). MS (m/z): 221 (M+H).

Step 2. 6-[(1-methylethyl)sulfonyl]-4(1H)-quinazolinone: 6-[(1-Methylethyl)thio]-4(1H)-quinazolinone (500 mg, 2.27 mmol) was dissolved in MeOH and water. Oxone (2.8 g, 4.5 mmol) was then added and the mixture stirred for 1 h. The reaction mixture was filtered. The solution was concentrated and crude material was purified by column chromatography (starting with 100% EtOAc to a mixture of 20% EtOAc with 80% of 10% NH₄OH in IPA). The collection was triturated with Et₂O to provide 700 mg product with 70% purity. MS (m/z): 253 (M+H).

Step 3. 4-chloro-6-[(1-methylethyl)sulfonyl]quinazoline: 6-[(1-Methylethyl)thio]-4(1H)-quinazolinone (0.20 g, 0.91 mmol), DMF (0.1 mL) and thionyl chloride (5 mL) were place in a sealed tube and heated at 85° C. for 5 h. LCMS showed 85% of starting material was converted to product. The solvent was removed in vacuo to provide the title compound (0.20 g crude material). MS (m/z): 271 (M+H).

Preparation 4

5-fluoro-1H-pyrazolo[3,4-b]pyridin-3-amine

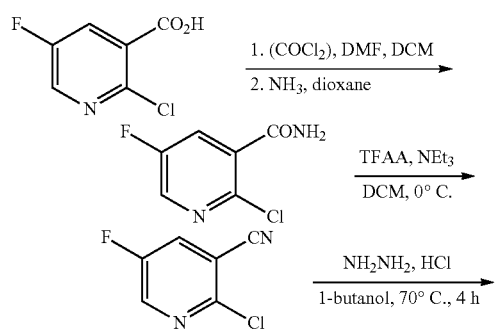

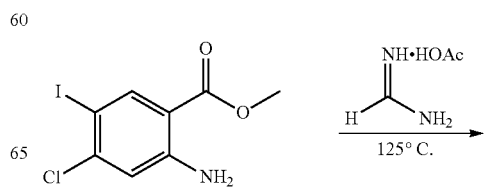

Step 1. 2-chloro-5-fluoro-3-pyridinecarboxamide: 2-Chloro-5-fluoro-3-pyridinecarboxylic acid (20 g, 110 mmol) was dissolved in CH₂Cl₂ (400 mL), and then DMF (88 μL, 1.1 mmol) was added at 0° C. After the DMF addition, oxalyl chloride (26 mL, 300 mmol) was added dropwise at 0° C. The reaction mixture was stirred at rt for 16 h, and concentrated in vacuo. The resulting yellow liquid was dissolved in 1,4-dioxane (400 mL), cooled to 0° C. and NH₃ (gas) (19.4 g, 1140 mmol) was bubbled through the solution for 30 min. The mixture was stirred at rt for 16 h. The resulting white mixture was filtered and the filtrate was concentrated to give the desired product as a white solid (18 g, 89% yield). MS (m/z) 175 (M+H⁺); ¹H NMR (400 MHz, DMSO-d₆) δ ppm 8.53 (d, 1 H), 8.10 (s, 1 H), 8.00 (dd, 1 H), 7.88 (s, 1 H).

Step 2. 2-chloro-5-fluoro-3-pyridinecarbonitrile: 2-Chloro-5-fluoro-3-pyridinecarboxamide (18 g, 102 mmol) was suspended in CH₂Cl₂ (500 mL), and then Et₃N (31 mL, 220 mmol) was added at 0° C. Trifluoroacetic anhydride (TFAA) (16 mL, 110 mmol) was added dropwise to the reaction mixture at 0° C. The white carboxamide starting material disappeared after 20 min at 0° C., indicating the completion of the reaction. The reaction mixture was stirred at 0° C. for 1 h. The reaction mixture was diluted with CH₂Cl₂, and then washed with satd. NaHCO₃(aq). The organic layer was washed with brine, dried over MgSO₄, filtered and the filtrate was concentrated to a brown residue. The residue was purified by column chromatography (8%-20% EtOAc/hexanes; 330 g column). Collected fractions were combined and concentrated to give the desired product as a white solid (15 g, 96% yield). MS (m/z) 157 (M+H⁺). ¹H NMR (400 MHz, DMSO-d₆) δ ppm 8.68 (dd, 1 H), 8.83 (d, 1 H).

Step 3. 5-fluoro-1H-pyrazolo[3,4-b]pyridin-3-amine: 2-Chloro-5-fluoro-3-pyridinecarbonitrile (15.3 g, 98 mmol) was dissolved in 1-butanol (300 mL), and then hydrazine monohydrate (16.82 mL, 293 mmol) was added, followed by hydrochloric acid (4N in 1,4-dioxane) (0.244 mL, 0.977 mmol). The reaction mixture was maintained at 70° C. for 4 h, and the resulting yellow crystalline solid was collected by filtration (12.5 g, 84% yield). MS (m/z) 153 (M+H⁺). ¹H NMR (400 MHz, DMSO-d₆) δ ppm 5.56 (s, 2 H), 7.97 (dd, 1 H), 8.39 (m, 1 H), 12.07 (s, 1 H).

Preparation 5

6-(tert-butylsulfonyl)-4,7-dichloroquinazoline

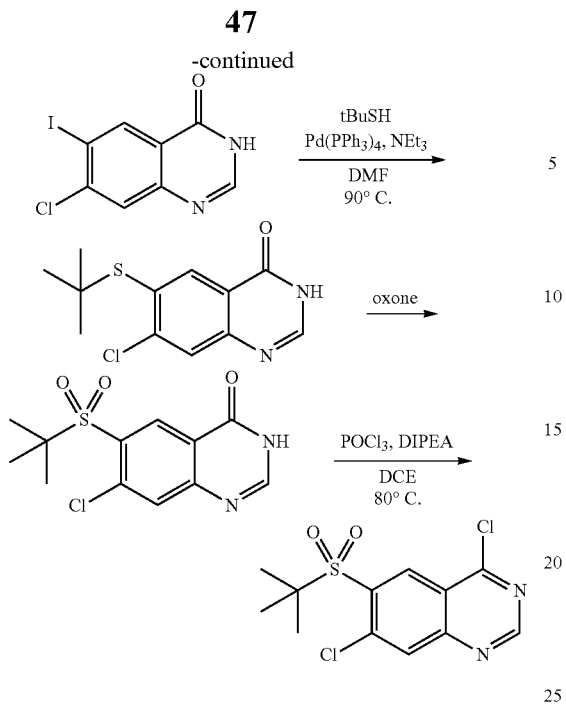

Step 1. 7-chloro-6-iodo-4(1H)-quinazolinone: A solution of methyl 2-amino-4-chloro-5-iodobenzoate (3.4 g, 10.9 mmol) and imidoformamide (3.4 g, 32.7 mmol) in 2-methoxyethanol (15 mL) was stirred at 125° C. for 7 h. The reaction mixture was allowed to cool to rt and the residue suspended in water. The solid was collected by filtration, washed with water and dried under vacuum (50° C.) to give 3.2 g of the title compound (96%). MS: m/z: 307 [M+H]+.

Step 2. 7-chloro-6-[(1,1-dimethylethyl)thio]-4(1H)-quinazolinone: To a solution of 6,7-bis[(1,1-dimethylethyl)thio]-4(1H)-quinazolinone (500 mg, 1.6 mmol), 2-methyl-2-propanethiol (162 mg, 1.8 mmol), Et$_3$N (0.68 mL, 4.9 mmol) in DMF (5 mL) was added Pd(Ph$_3$P)$_4$ (189 mg, 0.16 mmol). The reaction mixture was stirred at 90° C. for 1 h. Solvent was removed in vacuo. The crude material was purified by column chromatography (0 to 5% MeOH/CH$_2$Cl$_2$) to provide 0.37 g of the title compound (84%). MS: m/z: 269 [M+H]+.

Step 3. 7-chloro-6-[(1,1-dimethylethyl)sulfonyl]-4(1H)-quinazolinone: To a solution of 7-chloro-6-[(1,1-dimethylethyl)thio]-4(1H)-quinazolinone (370 mg, 1.4 mmol) in THF (8 mL) and water (2 mL) was added oxone (1.9 g, 3.0 mmol) and stirred overnight. Aq. NaHCO$_3$ was added to neutralize the solution to pH=7. The solution was extracted with EtOAc, dried over Na$_2$SO$_4$, filtered, and evaporated. Crude material was purified by column chromatography (0 to 8% MeOH/CH$_2$Cl$_2$) to give 0.30 g product (yield 64%). MS: m/z: 301 [M+H]+.

Step 4. 4,7-dichloro-6-[(1,1-dimethylethyl)sulfonyl]quinazoline: To a solution of 7-chloro-6-[(1,1-dimethylethyl)sulfonyl]-4(1H)-quinazolinone (180 mg, 0.60 mmol), POCl$_3$ (0.22 mL, 2.39 mmol) in 1,2-dichloroethane (5 mL) was added DIPEA (0.52 mL, 3.0 mmol). The reaction mixture was heated at 80° C. for 4 h and then cooled to rt. The solvent was removed under high vacuum. The residue was treated with satd. aq. NaHCO$_3$ and extracted with CH$_2$Cl$_2$. The organic extract was dried over Na$_2$SO$_4$. The organic extract was filtered and concentrated for use in the next step (166 mg of title compound). MS: m/z: 319 [M+H]+.

Preparation 6

6-(tert-butylsulfonyl)-4-chloro-7-methoxyquinazoline

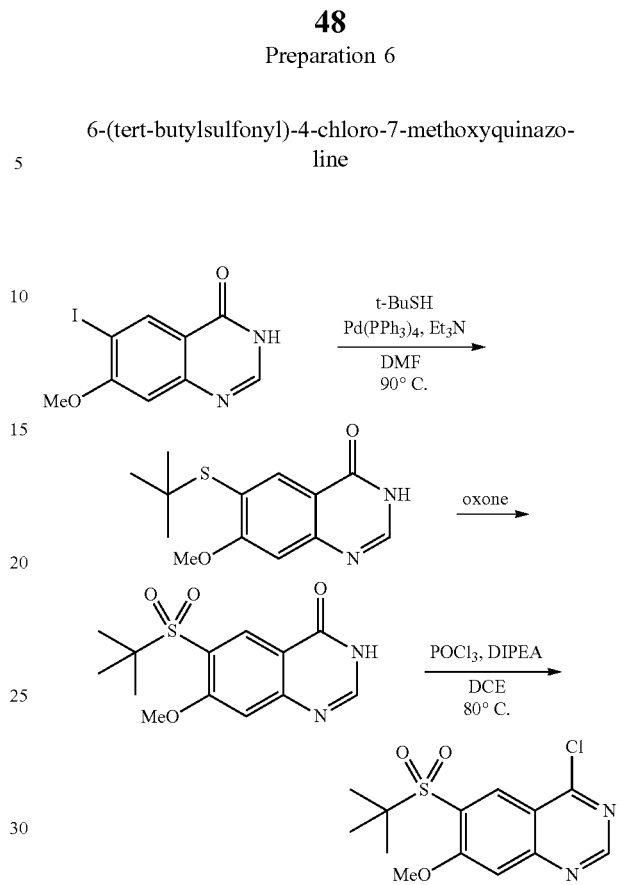

Step 1. 6-[(1,1-dimethylethyl)thio]-7-(methyloxy)-4(1H)-quinazolinone: To a solution of 6-iodo-7-(methyloxy)-4(1H)-quinazolinone (1.0 g, 3.3 mmol), 2-methyl-2-propanethiol (0.36 g, 4.0 mmol), Et$_3$N (1.4 mL, 9.9 mmol) in DMF (5 mL) was added Pd(Ph$_3$P)$_4$ (0.38 g, 0.33 mmol). The reaction mixture was stirred at 90° C. for 1 h. Solvent was removed in vacuo. The crude material was purified by column chromatography (0 to 5% MeOH/CH$_2$Cl$_2$) to provide 0.90 g of the title compound (93%). MS:m/z: 265 [M+H]+.

Step 2. 6-[(1,1-dimethylethyl)sulfonyl]-7-(methyloxy)-4(1H)-quinazolinone: 6-[(1,1-dimethylethyl)thio]-7-(methyloxy)-4(1H)-quinazolinone (900 mg, 3.4 mmol) was dissolved in MeOH (10 mL), THF (10 mL) and water (0.4 mL). Oxone (4.2 g, 6.8 mmol) was added and reaction mixture was stirred at rt overnight. The solution was filtered, and the solid was washed with CH$_2$Cl$_2$ and MeOH. The solvent was evaporated. The crude material was purified by column chromatography (0 to 10% MeOH/CH$_2$Cl$_2$). 1.1 g of the title compound as collected with a purity of 74%. MS:m/z: 297.2 [M+H]+.

Step 3. 4-chloro-6-[(1,1-dimethylethyl)sulfonyl]-7-(methyloxy)quinazoline: 6-[(1,1-Dimethylethyl)sulfonyl]-7-(methyloxy)-4(1H)-quinazolinone (60 mg, 0.20 mmol) and POCl$_3$ (2 mL, 21.5 mmol) and the reaction mixture was heated at 80° C. for 4 h. The solution was allowed to cool to rt. POCl$_3$ was removed under high vacuum. The residue was treated with satd. aqueous NaHCO$_3$ and extracted with CH$_2$Cl$_2$. The organic extract was dried over Na$_2$SO$_4$, filtered, and concentrated. MS:m/z: 315, 317 [M+H]+.

Preparation 7

3,4-Dimethyl-1H-pyrazol-5-amine

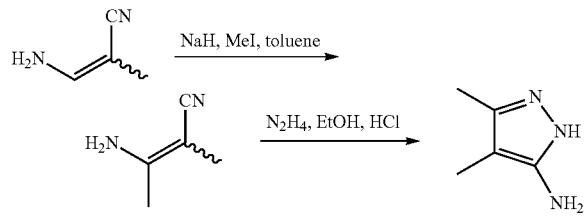

Step 1. 3-amino-2-methyl-2-butenenitrile: To a suspension of NaH (11.7 g, 292 mmol) in toluene (100 mL) at 30° C. was added a solution of (2Z)-3-amino-2-butenenitrile (20 g, 244 mmol) in toluene (400 mL) and the reaction mixture was stirred for 10 min. Iodomethane (15.23 mL, 244 mmol) was added and the reaction was cooled with cold water to maintain a temperature of 40° C. The reaction was then cooled to 30° C. and stirred overnight. An orange solid formed and was collected via filtration washing with toluene. The solid was suspended in water (400 mL) and stirred for 1 h. The solid was then filtered washing with water and air dried for 15 min, then placed under vacuum overnight (6.7 g, 29%). The mother liquor was concentrated under vacuum and the resulting residue dissolved in EtOAc to give a biphasic solution with mineral oil. The layers were separated and the EtOAc was removed under vacuum; the resulting solid was recrystallized from benzene to give the title compound (2.8 g, 12%). $^1$H NMR (400 MHz, DMSO-d$_6$) δ ppm 1.57 (s, 3 H) 1.92 (s, 3 H) 6.12 (br. s., 2 H); MS (m/z) 97 (M+H$^+$).

Step 2. 3,4-dimethyl-1H-pyrazol-5-amine: To a solution of 3-amino-2-methyl-2-butenenitrile (1.0 g, 10.4 mmol) in ethanol (10.4 mL) was added hydrazine (0.60 mL, 10.4 mmol). The resulting mixture was heated to 75° C. for 16 h open to atmosphere. The reaction was concentrated onto silica gel and purified via flash chromatography eluting with 0-10% MeOH in CH$_2$Cl$_2$ to give the title compound as a yellow oil (710 mg, 61%). $^1$H NMR (400 MHz, DMSO-d$_6$) δ ppm 1.72 (s, 3 H) 1.99 (s, 3 H) 3.99-4.50 (m, 2 H) 10.72-11.07 (m, 1 H); MS (m/z) 112 (M+H$^+$).

Preparation 8

N,4,5-trimethyl-1H-pyrazol-3-amine

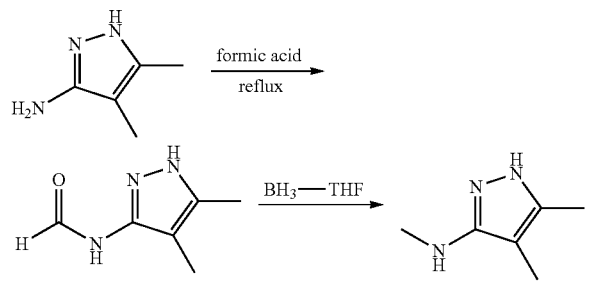

Step 1. (4,5-dimethyl-1H-pyrazol-3-yl)formamide. A mixture of 4,5-dimethyl-1H-pyrazol-3-amine (1.92 g, 17.3 mmol) in formic acid (10 mL) was stirred under nitrogen at reflux for 2 h. The reaction mixture was cooled to rt and concentrated to yield the title compound as a solid. LCMS (m/z): 140 (M+H$^+$).

Step 2. N,4,5-trimethyl-1H-pyrazol-3-amine. A mixture of (4,5-dimethyl-1H-pyrazol-3-yl)formamide (2.47 g, 17.7 mmol) and BH$_3$.THF (53.1 mL of a 1.0 M solution in THF, 53.1 mmol) was stirred under nitrogen at rt for 3 h. The mixture was then cooled to 0° C. and quenched with MeOH (dropwise addition). The crude product was purified via column chromatography using 0-7% MeOH:CH$_2$Cl$_2$ gradient, 80 g column to yield 0.70 g of the title compound as a colorless viscous oil. $^1$H NMR (400 MHz, DMSO-d$_6$) δ 10.27-11.36 (m, 1H), 4.56 (br. s., 1H), 2.64 (s, 3H), 2.00 (s, 3H), 1.71 (s, 3H); LCMS (m/z): 126 (M+H$^+$).

Example 1

4-methyl-3-{[6-(methylthio)-4-quinazolinyl]amino}phenol

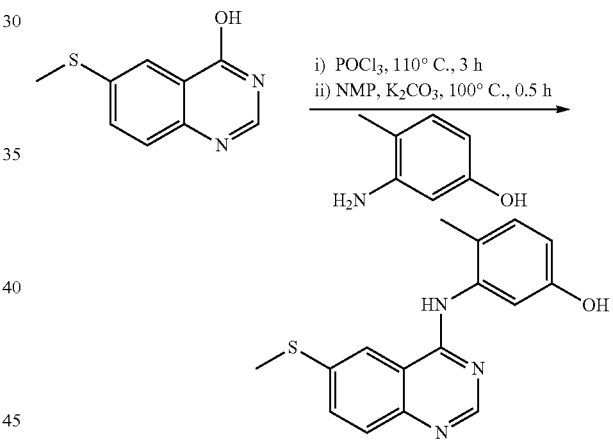

A mixture of 6-(methylthio)-4(1H)-quinazolinone (200 mg, 1.1 mmol) and phosphorus oxychloride (5.0 mL, 53 mmol) was heated at 110° C. for 3 h. Toluene was added and the reaction was concentrated to dryness. To the crude 4-chloro-6-(methylthio)quinazoline (249 mg, 1.18 mmol) in NMP (9.6 mL) were added potassium carbonate (490 mg, 3.5 mmol) and 3-amino-4-methylphenol (145 mg, 1.18 mmol). The reaction was heated at 100° C. for 30 min, cooled to rt, and partitioned between EtOAc and satd. NaHCO$_3$. The aqueous layer was extracted with EtOAc (3×) and the combined organic layers were washed with brine (3×), dried over MgSO$_4$, dry-loaded onto silica and chromatographed (Biotage SP-1, 25%-100% EtOAc/hexane) to yield 4-methyl-3-{[6-(methylthio)-4-quinazolinyl]amino}phenol (140 mg, 0.471 mmol, 39.9% yield). MS (m/z) 298 (M+H$^+$); $^1$H NMR (400 MHz, DMSO-d$_6$) δ 9.60 (s, 1H), 9.30 (s, 1H), 8.35 (s, 1H), 8.19 (d, J=2.0 Hz, 1H), 7.62-7.78 (m, 2H), 7.09 (d, J=8.3 Hz, 1H), 6.73 (d, J=2.3 Hz, 1H), 6.65 (dd, J=8.1, 2.5 Hz, 1H), 2.63 (s, 3H), 2.05 (s, 3H).

Example 2

4-methyl-3-{[6-(methylsulfonyl)-4-quinazolinyl]amino}phenol

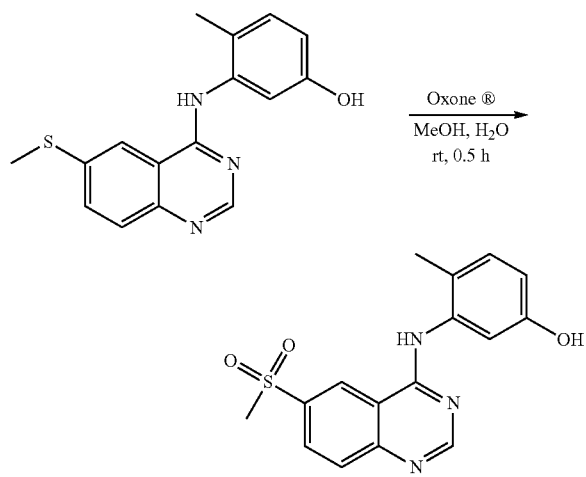

To a suspension of 4-methyl-3-{[6-(methylthio)-4-quinazolinyl]amino}phenol (130 mg, 0.44 mmol) in MeOH (2.5 mL) and water (2.5 mL) was added Oxone® (322 mg, 0.525 mmol). The reaction was stirred at rt for 30 min and concentrated to near dryness under a stream of nitrogen. The residue was partitioned between EtOAc and satd. NaHCO$_3$. The aqueous layer was extracted with EtOAc (2×) and the combined organic extracts were washed with brine (1×), dried over MgSO$_4$ and concentrated to dryness to yield pure 4-methyl-3-{[6-(methylsulfonyl)-4-quinazolinyl]amino}phenol (110 mg, 0.334 mmol, 76% yield). MS (m/z) 330 (M+H$^+$); $^1$H NMR (400 MHz, DMSO-d$_6$) δ 10.18 (s, 1H), 9.33 (s, 1H), 9.15 (d, J=2.0 Hz, 1H), 8.53 (s, 1H), 8.27 (dd, J=8.7, 1.9 Hz, 1H), 7.94 (d, J=8.8 Hz, 1H), 7.10 (d, J=8.3 Hz, 1H), 6.72 (d, J=2.5 Hz, 1H), 6.66 (dd, J=8.2, 2.4 Hz, 1H), 3.34 (s, 3H), 2.06 (s, 3H).

Example 3

N-1,3-benzothiazol-5-yl-6-[(1,1-dimethylethyl)thio]-4-quinazolinamine

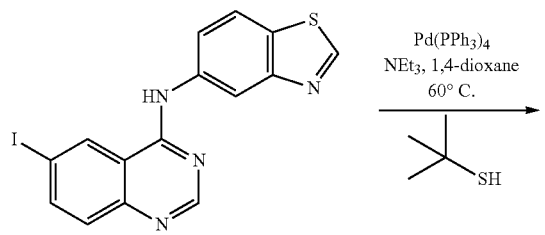

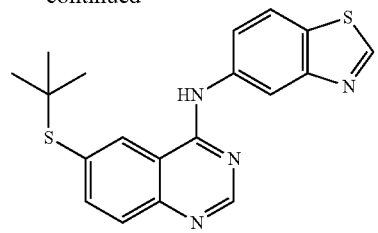

A 20 mL microwave vial was charged with N-1,3-benzothiazol-5-yl-6-iodo-4-quinazolinamine (182 mg, 0.270 mmol), Pd(Ph$_3$P)$_4$ (31.2 mg, 0.027 mmol) and 2-methyl-2-propanethiol (0.032 mL, 0.284 mmol). The flask was then evacuated and backfilled with nitrogen three times. 1,4-Dioxane (10 mL) was then added followed by Et$_3$N (0.25 mL, 1.794 mmol). The yellow suspension was sparged with argon for 5 min, then sealed and heated to 60° C. in a heating block. After 18 hr the reaction was cooled to rt and concentrated directly to afford a dark red oil. The crude material was purified via column chromatography (25 g SNAP column, 0-15% MeOH/CH$_2$Cl$_2$). The combined fractions containing the desired product appeared to be ~80% pure.

Example 4

N-1,3-benzothiazol-5-yl-6-[(1,1-dimethylethyl)sulfonyl]-4-quinazolinamine

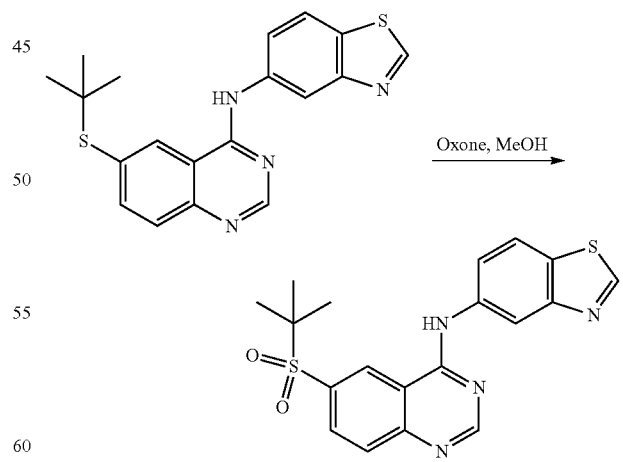

A 20 mL microwave vial was charged with N-1,3-benzothiazol-5-yl-6-iodo-4-quinazolinamine (182 mg, 0.270 mmol), Pd(Ph$_3$P)$_4$ (31.2 mg, 0.027 mmol) and 2-methyl-2-propanethiol (0.032 mL, 0.284 mmol). The flask was then evacuated and backfilled with nitrogen three times. 1,4-

Dioxane (10 mL) was then added followed by Et₃N (0.25 mL, 1.794 mmol). The yellow suspension was sparged with argon for 5 min, then sealed and heated to 60° C. in a heating block. After 18 hr the reaction was cooled to rt and concentrated directly to afford a dark red oil. The crude material was purified via column chromatography (25 g SNAP column, 0-15% MeOH/CH$_2$Cl$_2$). The combined fractions containing the desired product appeared to be ~80% pure.

Alternatively, this reaction can be run in solvents other than 1,4-dioxane, including DMF, and at temperatures other than 60° C. as appropriate for each substrate.

N-1,3-benzothiazol-5-yl-6-[(1,1-dimethylethyl)thio]-4-quinazolinamine (150 mg, 0.327 mmol) was dissolved in MeOH (10 mL) in a 20 mL scintillation vial. To this deep red solution was added oxone (300 mg, 0.488 mmol) and the reaction was stirred at rt. After 1 hr the reaction was treated with 5 mL of (5:1 Na$_2$S$_2$O$_3$/NaHCO$_3$) for 5 min then poured into 50 mL sat. aq. bicarbonate solution. The mixture was diluted with 50 mL H$_2$O and then extracted with CH$_2$Cl$_2$ (50 mL×3) and EtOAc (50 mL). The combined organics were concentrated and the crude material was purified via column chromatography (25 g SNAP column, 0-8% MeOH/CH$_2$Cl$_2$) to afford 37 mg (26%) of the title compound. MS (m/z) 399.1 (M+H$^+$). $^1$H NMR (DMSO-d$_6$) δ: 10.65 (br. s., 1H), 9.44 (s, 1H), 9.26 (s, 1H), 8.75 (s, 1H), 8.64 (s, 1H), 8.10-8.28 (m, 2H), 7.99 (d, J=8.6 Hz, 1H), 7.89-7.96 (m, 1H), 1.33 (s, 9H).

Select compounds were purified by reverse phase HPLC.

The following examples were prepared in the same manner:

| Ex. | Structure/Name | MS (M + H)$^+$ | NMR | Method |
|---|---|---|---|---|
| 5 | 6-(tert-butylsulfonyl)-N-(5-fluoro-1H-indazol-3-yl)quinazolin-4-amine | 401 | $^1$H NMR (400 MHz, DMSO-d$_6$) δ 1.34 (s, 9H), 7.28 (td, J = 9.03, 2.15 Hz, 1H), 7.41 (d, J = 8.84 Hz, 1H), 7.57 (dd, J = 8.97, 4.17 Hz, 1H), 7.91 (d, J = 8.08 Hz, 1H), 8.12 (d, J = 8.34 Hz, 1H), 8.53 (s, 1H), 9.15 (s., 1H), 12.25 (br. S. 1H) | as Ex. 4 |
| 6 | N-1,3-benzothiazol-5-yl-6-[(1-methylethyl)sulfonyl])-4-quinazolinamine | 385.1 | $^1$H NMR (DMSO-d$_6$) δ: 10.64 (br. s., 1H), 9.44 (s, 1H), 9.27 (s, 1H), 8.75 (s, 1H), 8.66 (s, 1H), 8.14-8.29 (m, 2H), 8.00 (d, J = 8.8 Hz, 1H), 7.87-7.96 (m, 1H), 3.49-3.65 (m, 1H), 1.24 (d, J = 6.8 Hz, 6H). | as Ex. 4 |
| 7 | 2-{[4-(1,3-benzothiazol-5-ylamino)-6-quinazolinyl]sulfonyl}ethanol | 387 | $^1$H NMR (DMSO-d$_6$) δ: 9.23 (s, 1H), 8.73 (br. s., 1H), 8.06 (br. s., 1H), 7.85 (d, J = 8.3 Hz, 1H), 7.75-7.83 (m, 1H), 7.61-7.75 (m, 2H), 7.39 (br. s., 2H), 4.27 (t, J = 6.9 Hz, 1H), 4.15 (dd, J = 5.4, 3.4 Hz, 2H), 3.70 (t, 2H). | as Ex. 4 |
| 8 | N-1,3-benzothiazol-5-yl-6-(tetrahydro-2H-pyran-4-ylsulfonyl)-4-quinazolinamine | 427 | $^1$H NMR (DMSO-d$_6$) δ: 10.62 (br. s., 1H), 9.44 (s, 1H), 9.26 (s, 1H), 8.77 (s, 1H), 8.67 (s, 1H), 8.15-8.27 (m, 2H), 7.89-8.07 (m, 2H), 4.94-5.07 (m, 1H), 4.09 (q, J = 5.2 Hz, 1H), 3.94 (dd, J = 11.2, 3.9 Hz, 2H), 3.58-3.74 (m, 1H), 3.18 (d, J = 5.3 Hz, 4H). | as Ex. 4 |

Example 9

N-1,3-benzothiazol-5-yl-6-(tetrahydro-2H-pyran-4-ylsulfonyl)-4-quinazolinamine

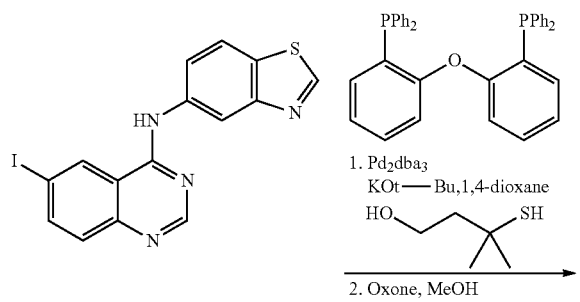

Step 1. 3-{[4-(1,3-benzothiazol-5-ylamino)-6-quinazolinyl]thio}-3-methyl-1-butanol: To a solution of N-1,3-benzothiazol-5-yl-6-iodo-4-quinazolinamine (202 mg, 0.500 mmol), 3-mercapto-3-methyl-1-butanol (60 mg, 0.50 mmol), potassium tert-butoxide (168 mg, 1.50 mmol) and (oxydi-2,1-phenylene)bis(diphenyl phosphine) (27 mg, 0.05 mmol) in dioxane (4 mL) was added Pd$_2$dba$_3$ (46 mg, 0.05 mmol) and the mixture was sparged with N$_2$ for 10 min. The reaction was complete in 2 h. Solvent was removed and the crude material was purified via column chromatography (0 to 5% MeOH/CH$_2$Cl$_2$) to afford 142 mg of the title compound (72%). MS: m/z: 397 [M+H]$^+$ Cesium carbonate may also be used as the base in these coupling reactions. An equivalent of triethamine may also be added when the starting quinazoline is an HCl salt.

Step 2. 3-{[4-(1,3-benzothiazol-5-ylamino)-6-quinazolinyl]sulfonyl}-3-methyl-1-butanol: 3-{[4-(1,3-benzothiazol-5-ylamino)-6-quinazolinyl]thio}-3-methyl-1-butanol (140 mg, 0.35 mmol) and oxone (434 mg, 0.71 mmol) were suspended in MeOH (2 mL) and the mixture was stirred at rt for 5 h. Upon filtration the cake was washed with MeOH and the filtrate was concentrated. The crude material was purified via column chromatography (0 to 8% MeOH/CH$_2$Cl$_2$) to afford 3-{[4-(1,3-benzothiazol-5-ylamino)-6-quinazolinyl]sulfonyl}-3-methyl-1-butanol (67 mg, 0.15 mmol, 42% yield). MS: m/z: 429 [M+H]$^+$; $^1$H NMR (DMSO-d$_6$) δ: 10.66 (s, 1H), 9.44 (s, 1H), 9.25 (d, J=1.5 Hz, 1H), 8.76 (s, 1H), 8.64 (d, J=1.8 Hz, 1H), 8.13-8.30 (m, 2H), 7.89-8.07 (m, 2H), 4.58 (t, J=4.8 Hz, 1H), 3.58 (d, J=5.3 Hz, 2H), 1.86 (t, J=6.9 Hz, 2H), 1.34 (s, 6H).

EtOH and water (1:1) may also be used as the solvent mixture.

The following example was prepared in a similar manner:

| Ex. | Structure/Name | MS (M + H)$^+$ | NMR | Method |
|---|---|---|---|---|
| 10 | 2-((4-((4,5-dimethyl-1H-pyrazol-3-yl)amino)-7-methoxyquinazolin-6-yl)sulfonyl)ethanol | 378 | $^1$H NMR (400 MHz, METHANOL-d4) δ ppm 1.95 (s, 3H), 2.31 (s, 3H), 3.73 (t, J = 5.68 Hz, 2H), 3.93-3.97 (m, 2H), 4.22 (s, 3H), 7.38 (s, 1H), 8.72 (s, 1H), 9.15 (br. s., 1H) | Cs$_2$CO$_3$ as base in step 1; EtOH/H$_2$O as solvent in step 2 |

Example 11

N-(5-fluoro-1H-indazol-3-yl)-6-[(1-methylethyl)sulfonyl]-4-quinazolinamine

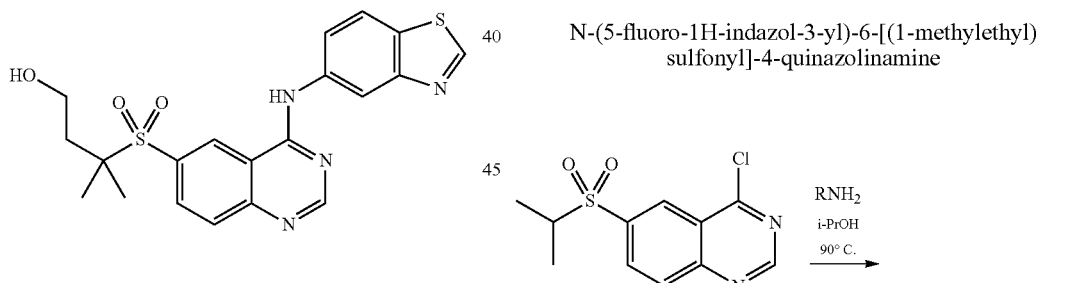

To a solution of 4-chloro-6-[(1-methylethyl)sulfonyl]quinazoline (100 mg, 0.37 mmol) in isopropanol (1 mL) was added 5-fluoro-1H-indazol-3-amine (56 mg, 0.37 mmol). The reaction mixture was stirred at 90° C. for 1 h. The solvent was removed in vacuo and the crude material was purified by HPLC to give 23 mg of the title compound. MS (m/z): 386 (M+H). $^1$H NMR (DMSO-d$_6$) δ: 13.01 (br. s., 1H), 9.19 (br. s., 1H), 8.54 (br. s., 1H), 8.17 (br. s., 1H), 7.95

(br. s., 1H), 7.58 (dd, J=9.1, 4.3 Hz, 1H), 7.44 (br. s., 1H), 7.29 (td, J=9.1, 2.3 Hz, 1H), 3.48-3.65 (m, 1H), 1.25 (d, J=6.8 Hz, 6H).

The following compounds were prepared using procedures analogous to those described above using the appropriate commercial amine. Examples 11 and 12 were neutralized with Et₃N before being concentrated for purification. Some reactions varied in temperature and solvent.

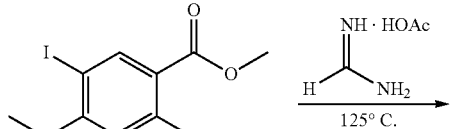

| Ex. | Structure/Name | MS (M + H)⁺ | NMR | Method |
|---|---|---|---|---|
| 12 | N-(4,5-dimethyl-1H-pyrazol-3-yl)-6-[(1-methylethyl)sulfonyl]-4-quinazolinamino | 346 | ¹H NMR (400 MHz, DMSO-d₆): δ = 12.31 (s, 1H), 9.40 (s, 1H), 9.06 (s, 1H), 8.53 (d, J = 5.3 Hz, 1H), 7.90 (m, 1H), 6.60 (d, J = 5.3 Hz, 1H), 2.22 (s, 3H), 1.81 ppm (s, 3H), 1.25 (d, J = 6.8 Hz, 6H). | as Ex. 11 |
| 13 | 6-(tert-butylsulfonyl)-N-(5-(trifluoromethyl)-1H-pyrazol-3-yl)quinazolin-4-amine | 400 | ¹H NMR (400 MHz, DMSO-d₆) δ 13.65 (br. s., 1H), 11.70 (br. s., 1H), 8.42-9.17 (m, 2H), 8.14 (d, J = 8.08 Hz, 1H), 7.89 (br. s., 1H), 6.79 (br. s., 1H), 1.30 (s, 9H) | as Ex. 11 using 1,4-dioxane as solvent |
| 14 | 6-(tert-butylsulfonyl)-N-(1,3,4-trimethyl-1H-pyrazol-5-yl)quinazolin-4-amine | 374 | ¹H NMR (400 MHz, DMSO-d₆) δ 10.38 (br. s., 1H), 9.10 (br. s., 1H), 8.63 (br. s., 1H), 8.17 (d, J = 8.34 Hz, 1H), 7.99 (d, J = 8.34 Hz, 1H), 3.54 (s, 3H), 2.11 (s, 3H), 1.79 (s, 3H), 1.32 (s, 9H) | as Ex. 11 using 1,4-dioxane as solvent at 150° C. |

Example 15

N-(6-(tert-butylthio)-7-methoxyquinazolin-4-yl)benzo[d]thiazol-5-amine

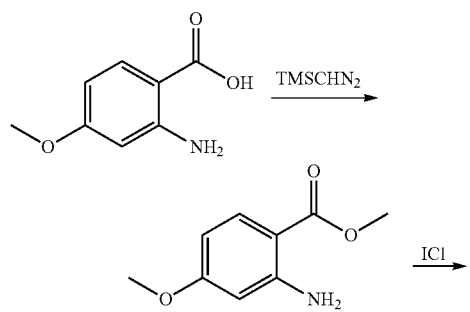

-continued

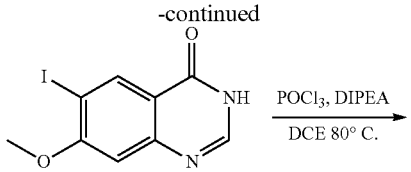

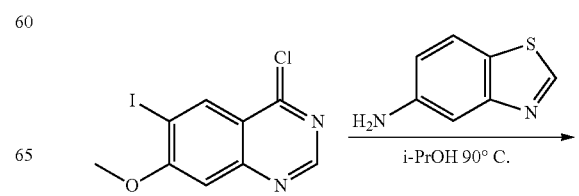

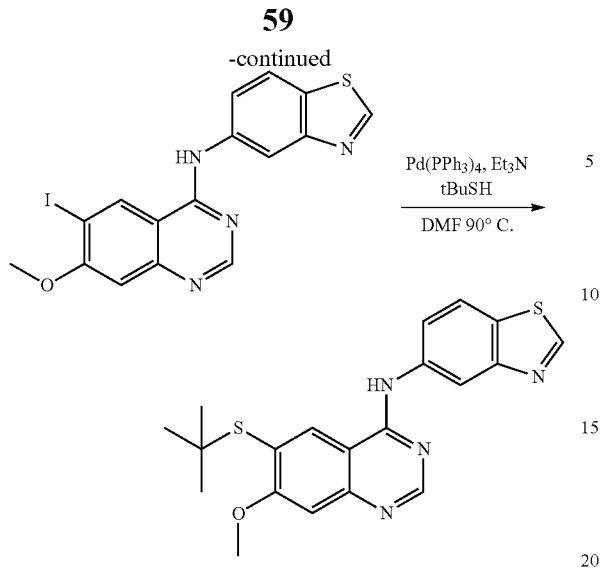

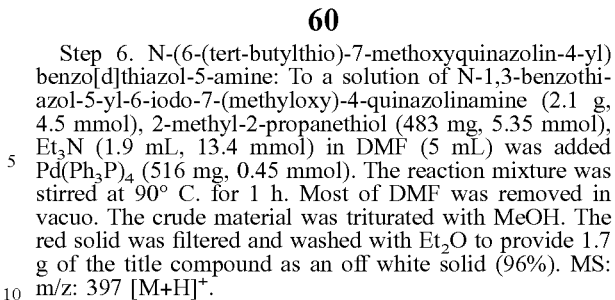

Step 1. Methyl 2-amino-4-methoxybenzoate: To a solution of 2-amino-4-(methyloxy) benzoic acid (5 g, 30 mmol) in MeOH (30 mL) and toluene (60 mL) was added trimethylsilyldiazomethane (30 mL, 60 mmol). The reaction mixture was stirred at 0° C. for 1 h. The reaction mixture was allowed to warm to rt and solvent was removed in vacuo. The crude material was purified by column chromatography (0 to 15% EtOAC/hexanes) to provide 4.2 g of the title compound (74%). MS: m/z: 182 [M+H]$^+$.

Step 2. Methyl 2-amino-5-iodo-4-methoxybenzoate: Methyl 2-amino-4-(methyloxy) benzoate (3.78 g, 20.86 mmol) was dissolved in 25 mL of water, 15 mL of ethanol and 2.2 mL of concentrated HCl. A solution of ICl (1.1 mL, 21.9 mmol) in 3.8 mL concentrated HCl and 14 mL of water at 5° C. was added to the aniline solution. The reaction was stirred overnight and was then filtered to obtain 6.9 g of a light brown solid. MS: m/z: 308 [M+H]$^+$ Step 3. 6-iodo-7-methoxyquinazolin-4(1H)-one: A solution of methyl 2-amino-5-iodo-4-(methyloxy)benzoate (2 g, 6.5 mmol) and imidoformamide (2.0 g, 19.5 mmol) in 2-methoxyethanol (15 mL) was stirred at 125° C. for 6 h. The solvent was removed in vacuo, and the residue was suspended in water and the solid was collected by filtration, washed with water and dried under vacuum (50° C.) to afford 2.1 g of the title compound (96% pure). MS: m/z: 303 [M+H]$^+$.

Step 4. 4-chloro-6-iodo-7-(methyloxy)quinazoline: 6-Iodo-7-(methyloxy)-4(1H)-quinazolinone (2.0 g, 6.6 mmol), POCl$_3$ (3.1 mL, 33.1 mmol) and DIPEA (6.9 mL, 40 mmol) were combined in DCE (50 mL) a round bottom flask. The reaction mixture was heated at 80° C. for 5 h, followed by heating at 70° C. for 10 h. The reaction mixture was allowed to cool to rt. A yellow solid was precipitated out. The solid was filtered. The solution was concentrated and neutralized with satd. NaHCO$_3$, extracted with CH$_2$Cl$_2$ and dried over Na$_2$SO$_4$. The mixture was filtered, and the solvent was removed in vacuo. Solid portions were combined to obtain 2.0 g of the title compound (88%). MS: m/z: 321 [M+H]$^+$.

Step 5. N-1,3-benzothiazol-5-yl-6-iodo-7-(methyloxy)-4-quinazolinamine: To a solution of 4-chloro-6-iodo-7-(methyloxy)quinazoline (2.0 g, 5.4 mmol) in isopropanol (30 mL) was added 1,3-benzothiazol-5-amine (1.2 g, 8.1 mmol). The suspension was heated in oil bath at 90° C. (preheated). The reaction mixture stirred at this temperature for 30 min. A yellow solid precipitated out as the reaction mixture was allowed to cool to rt. The solid was filtered to provide 2.1 g of the title compound (77%, 93% pure). MS: m/z: 471 [M+H]$^+$.

Step 6. N-(6-(tert-butylthio)-7-methoxyquinazolin-4-yl)benzo[d]thiazol-5-amine: To a solution of N-1,3-benzothiazol-5-yl-6-iodo-7-(methyloxy)-4-quinazolinamine (2.1 g, 4.5 mmol), 2-methyl-2-propanethiol (483 mg, 5.35 mmol), Et$_3$N (1.9 mL, 13.4 mmol) in DMF (5 mL) was added Pd(Ph$_3$P)$_4$ (516 mg, 0.45 mmol). The reaction mixture was stirred at 90° C. for 1 h. Most of DMF was removed in vacuo. The crude material was triturated with MeOH. The red solid was filtered and washed with Et$_2$O to provide 1.7 g of the title compound as an off white solid (96%). MS: m/z: 397 [M+H]$^+$.

The following compound, N-(6-(isopropylthio)-7-methoxyquinazolin-4-yl)benzo[d]thiazol-5-amine (used only as an intermediate and not submitted for testing against RIP2 kinase), was made in a similar manner:

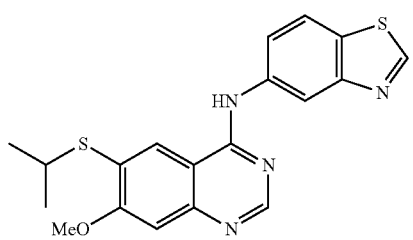 [SMILES: COc1cc2ncnc(Nc3ccc4scnc4c3)c2cc1SC(C)C]

Example 16

N-(6-(tert-butylsulfonyl)-7-methoxyquinazolin-4-yl)benzo[d]thiazol-5-amine

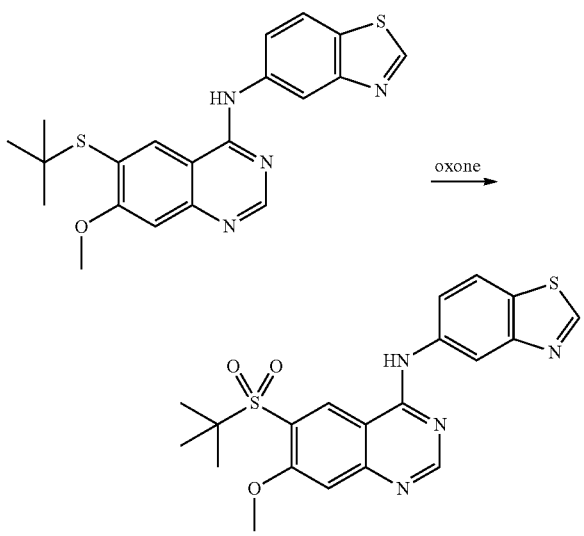

To a solution of N-(6-(tert-butylthio)-7-methoxyquinazolin-4-yl)benzo[d]thiazol-5-amine (1.2 g, 2.5 mmol) in THF (20 mL) and water (2 mL) was added oxone (3.1 g, 5.0 mmol). The reaction mixture was stirred at rt for 8 h. Satd. aq. NaHCO$_3$ was added to the reaction mixture to adjust to pH~7. The mixture was extracted with EtOAc (100 mL×2) and CH$_2$Cl$_2$ (100 mL×2), dried over Na$_2$SO$_4$, and filtered. The solvent was removed in vacuo and crude material was purified by column chromatography (0 to 8% MeOH/CH$_2$Cl$_2$) to provide 530 mg of the title compound (19%). MS: m/z: 429 [M+H]$^+$; $^1$H NMR (400 MHz, DMSO-d$_6$) δ 1.34 (s, 9 H), 4.01 (s, 3 H), 7.40 (s, 1 H), 7.89 (dd, J=8.80, 1.78 Hz, 1 H), 8.17 (d, J=8.80 Hz, 1 H), 8.59 (d, J=1.78 Hz, 1 H), 8.64 (s, 1 H), 9.14 (s, 1 H), 9.42 (s, 1 H), 10.55 (s, 1 H).

The following example was prepared in a similar manner:

| Ex. | Structure/Name | MS (M + H)+ | NMR | Method |
|---|---|---|---|---|
| 17 | N-(6-(isopropylsulfonyl)-7-methoxyquinazolin-4-yl)benzo[d]thiazol-5-amine | 415 | $^1$H NMR (400 MHz, DMSO-$d_6$) δ 1.23 (d, J = 6.82 Hz, 6H), 3.79 (dt, J = 13.71, 6.66 Hz, 1H), 4.08 (s, 3H), 7.43 (s, 1H), 7.89 (d, J = 8.84 Hz, 1H), 8.16 (d, J = 8.84 Hz, 1H), 8.63 (d, J = 13.39 Hz, 2H), 9.14 (s, 1H), 9.42 (s, 1H), 10.56 (br. s., 1H). | as Ex. 16 |

Example 18

4-(benzo[d]thiazol-5-ylamino)-6-(tert-butylsulfonyl)quinazolin-7-ol

Examples 19 and 20

N-(6-(tert-butylsulfonyl)-7-ethoxyquinazolin-4-yl)benzo[d]thiazol-5-amine and N-(6-(tert-butylsulfonyl)-7-ethoxyquinazolin-4-yl)-N-ethylbenzo[d]thiazol-5-amine

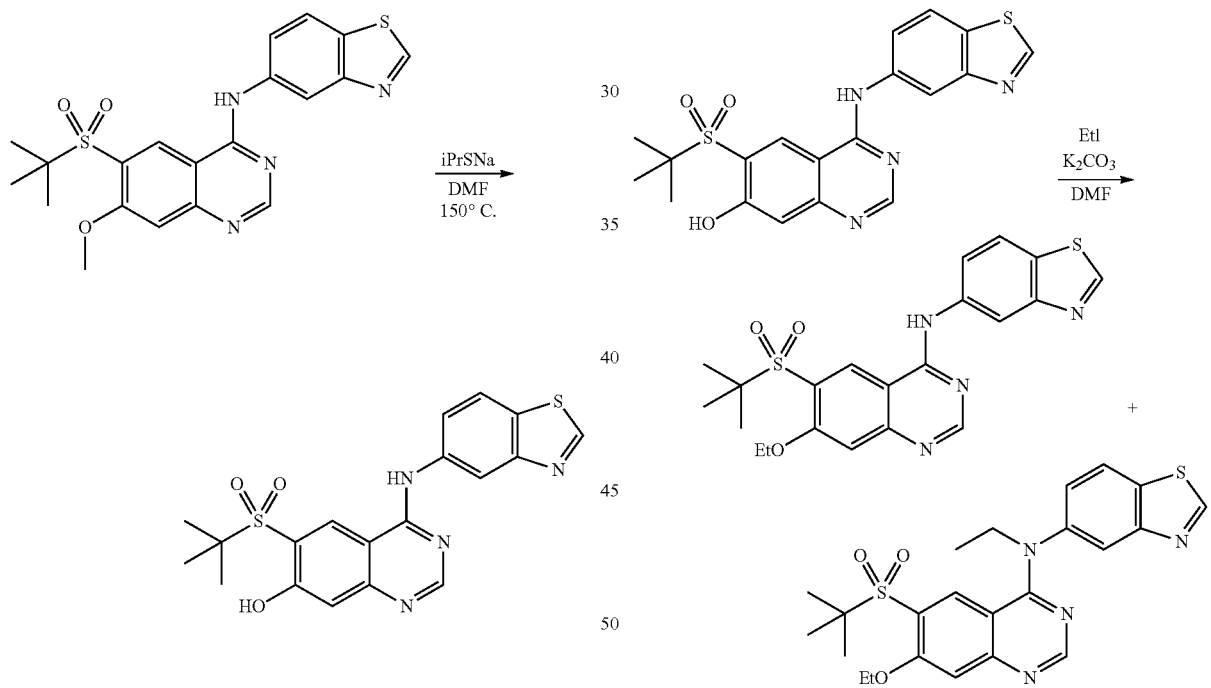

To a solution of N-(6-(tert-butylsulfonyl)-7-methoxyquinazolin-4-yl)benzo[d]thiazol-5-amine (2.0 g, 4.7 mmol) in DMF (30 mL) was added sodium isopropylthiolate (2.7 g, 28.0 mmol), and the solution was stirred at 150° C. for 1 h. Solvent was removed in vacuo. 1 N aq. HCl was added to reaction mixture to neutralize to pH=6. A yellow solid precipitated out, which was filtered and purified by column chromatography (0 to 5% MeOH/CH$_2$Cl$_2$) to provide 1.5 g of the title compound (65%). MS: m/z: 415 [M+H]+; $^1$H NMR (400 MHz, DMSO-$d_6$) δ 1.15-1.46 (s, 9 H), 7.21 (s, 1 H), 7.89 (dd, J=8.72, 1.78 Hz, 1 H), 8.16 (d, J=8.72 Hz, 1 H), 8.55 (s, 1 H), 8.58 (d, J=1.78 Hz, 1 H), 9.07 (s, 1 H), 9.42 (s, 1 H), 10.47 (s, 1 H), 11.45 (br. s., 1 H).

To a solution of 4-(1,3-benzothiazol-5-ylamino)-6-[(1,1-dimethylethyl)sulfonyl]-7-quinazolinol (66 mg, 0.15 mmol) in DMF (1 mL) was added K$_2$CO$_3$ (62 mg, 0.45 mmol). The solution was stirred at rt for 10 min. Iodoethane (35 mg, 0.23 mmol) was then added, and the reaction mixture was stirred at rt for 30 min. Solid precipitate was filtered out, and solution was concentrated for purification. The crude material was purified by HPLC. The two products were not separable. The TFA salts were neutralized by passing the material through a carbonate cartridge. The mixture was repurified by column chromatography (0 to 4% MeOH/CH$_2$Cl$_2$) to isolate 13 mg of N-(6-(tert-butylsulfonyl)-7-ethoxyquinazolin-4-yl)benzo[d]thiazol-5-amine (20%). MS: m/z: 443 [M+H]+; $^1$H NMR (400 MHz, DMSO-$d_6$) δ 1.35 (s, 9 H), 1.42 (t, J=6.96 Hz, 3 H), 4.30 (q, J=6.96 Hz, 2 H), 7.36 (s, 1 H), 7.89 (d, J=8.84 Hz, 1 H), 8.16 (d, J=8.84 Hz, 1 H), 8.58 (s., 1 H), 8.62 (s., 1 H), 9.13 (s, 1 H), 9.42 (s, 1 H), 10.54 (s, 1 H). In addition, 7% of the over alkylation product N-(6-(tert-butylsulfonyl)-7-ethoxyquinazolin-4-yl)-N-ethylbenzo[d]thiazol-5-amine was obtained and isolated. MS:m/z: 471 [M+H]$^+$; $^1$H NMR (400 MHz, DMSO-d$_6$) δ 1.18-1.38 (m, 12 H), 1.41 (t, J=6.95 Hz, 3 H), 4.15 (q, J=7.07 Hz, 2 H), 4.33 (q, J=7.07 Hz, 2 H), 6.99 (s, 1 H), 7.15 (dd, J=8.34, 1.77 Hz, 1 H), 7.67 (d, J=1.52 Hz, 1 H), 7.98 (d, J=8.59 Hz, 1 H), 8.04 (s, 1 H), 8.66 (s, 1 H), 9.30 (s, 1 H).

Example 21

2-((4-(benzo[d]thiazol-5-ylamino)-6-(tert-butylsulfonyl)quinazolin-7-yl)oxy)ethanol

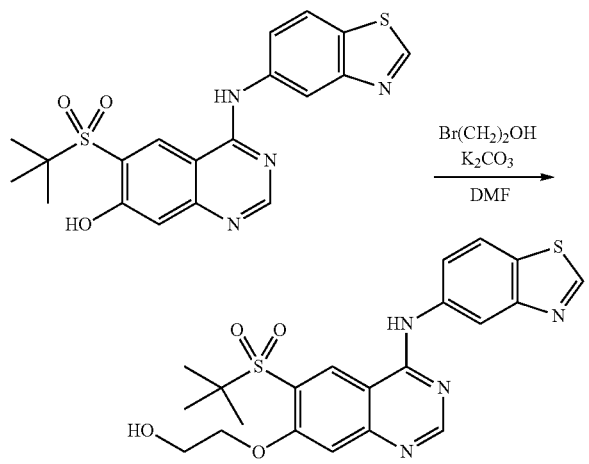

4-(Benzo[d]thiazol-5-ylamino)-6-(tert-butylsulfonyl)quinazolin-7-ol (8.0 g, 19.3 mmol) and K$_2$CO$_3$ (5.9 g, 42.5 mmol) were dissolved in 98 ml DMF and stirred 2 min before adding 2-bromoethanol (5.1 mL, 72.4 mmol). The mixture was heated for 3 h at 70° C., and then cooled to rt and stirred for 18 h. Water (300 mL) was added, and the resulting solid was filtered and washed with water. The wet cake was slurried again in water and filtered to give a tan solid. The solid was dissolved in hot EtOAc/MeOH (150 mL/50 mL) and cooled to rt to give a white solid precipitate which was filtered and dried under vacuum to give the product as a white solid (2.4 g). The resulting filtrate was evaporated to dryness, triturated with EtOAc, filtered, and dried to give a light brown solid (3.1 g). The solids were combined (5.5 g, 62% yield). Several batches of this material were combined to give 15 g of input material. To this solid was added water (150 mL). The mixture was sonicated, and stirred for 15 min at rt. The solid was filtered and dried under vacuum at 70° C. for 3 days to give the title compound as a solid (14.8 g, 98% recovery). MS: m/z: 459 [M+H]$^+$; $^1$H NMR (400 MHz, DMSO-d$_6$) δ 1.36 (s, 9 H), 3.81 (q, J=4.80 Hz, 2 H), 4.28 (t, J=4.80 Hz, 2 H), 4.81 (t, J=4.80 Hz, 1 H), 7.41 (s, 1 H), 7.89 (d, J=8.40 Hz, 1 H), 8.17 (d, J=8.40 Hz, 1 H), 8.58 (s, 1 H), 8.63 (s, 1 H), 9.14 (s, 1 H), 9.42 (s, 1 H), 10.55 (s, 1 H).

The following compounds were prepared using procedures analogous to those described above using the appropriate alkylating agent. Isolation and purification methods vary depending upon the substrate.

| Ex. | Structure/Name | MS (M + H)$^+$ | NMR | Method |
|---|---|---|---|---|
| 22 | N-(6-(tert-butylsulfonyl)-7-(difluoromethoxy)quinazolin-4-yl)benzo[d]thiazol-5-amine | 465 | $^1$H NMR (400 MHz, DMSO-d$_6$) δ 1.37 (s, 9H), 3.17 (s, 1H), 7.59 (s, 1H), 7.88 (s, 1H), 8.17 (s, 1H), 8.56 (s, 1H), 8.70 (s, 1H), 9.27 (s, 1H), 9.43 (s, 1H), 10.76 (s, 1H) | as Ex. 21 |
| 23 | N-(6-(tert-butylsulfonyl)-7-(2,2,2-trifluoromethoxy)quinazolin-4-yl)benzo[d]thiazol-5-amine | 497 | $^1$H NMR (400 MHz, DMSO-d$_6$) δ 1.35 (s, 9H), 5.08 (d, J = 8.59 Hz, 2H), 7.51 (br. s., 1H), 7.87 (br. s., 1H), 8.16 (d, J = 7.83 Hz, 1H), 8.56 (br. s., 2H), 9.17 (br. s., 1H), 9.42 (s, 1H), 10.63 (br. s., 1H) | as Ex. 21 |

| Ex. | Structure/Name | MS (M + H)+ | NMR | Method |
|---|---|---|---|---|
| 24 | N-(6-(tert-butylsulfonyl)-7-(methoxymethoxy)quinazolin-4-yl)benzo[d]thiazol-5-amine | 473 | $^1$H NMR (400 Hz, DMSO-$d_6$) δ 1.35 (s, 9H), 3.35 (s, 3H), 3.67-3.84 (m, 2H), 4.28-4.53 (m, 2H), 7.39 (br, 1H), 7.88 (s, 1H), 8.16 (d, J = 8.59 Hz, 1H), 8.57 (s, 2H), 9.13 (s, 1H), 9.41 (s, 1H), 10.55 (br s, 1H) | as Ex. 21 |
| 25 | N-(6-(tert-butylsulfonyl)-7-(cyclohexylmethoxy)quinazolin-4-yl)benzo[d]thiazol-5-amine | 511 | $^1$H NMR (400 MHz, DMSO-$d_6$) δ 0.98-1.31 (m, 6H), 1.35 (s, 9H), 1.59-2.03 (m, 5H), 4.04 (d, J = 6.32 Hz, 2H), 7.36 (s, 1H), 7.89 (dd, J = 8.72, 1.64 Hz, 1H), 8.16 (d, J = 8.84 Hz, 1H), 8.58 (d, J = 1.52 Hz, 1H), 8.62 (s, 1H), 9.13 (s, 1H), 9.42 (s, 1H), 10.54 (s, 1H) | as Ex. 21 |
| 26 | 3-((4-(benzo[d]thiazol-5-ylamino)-6-(tert-butylsulfonyl)quinazolin-7-yl)oxy)propan-1-ol | 473 | $^1$H NMR (DMSO-$d_6$) δ: 10.54 (s, 1H), 9.42 (s, 1H), 9.14 (s, 1H), 8.56-8.65 (m, 2H), 8.17 (d, J = 8.6 Hz, 1H), 7.88 (s, 1H), 7.37 (s, 1H), 4.57 (t, J = 5.3 Hz, 1H), 4.30 (t, J = 6.1 Hz, 2H), 3.60-3.71 (m, 2H), 1.95 (quin, J = 6.2 Hz, 2H), 1.35 (s, 9H) | as Ex. 21 |
| 27 | N-(6-(tert-butylsulfonyl)-7-((tetrahydro-2H-pyran-4-yl)oxy)quinazolin-4-yl)benzo[d]thiazol-5-amine | 499 | $^1$H NMR (DMSO-$d_6$) δ: 11.16 (s, 1H), 9.45 (s, 1H), 9.23 (s, 1H), 8.74 (s, 1H), 8.52 (s, 1H), 8.22 (d, J = 8.6 Hz, 1H), 7.80-7.87 (m, 1H), 7.48 (s, 1H), 5.03-5.12 (m, 1H), 3.87-3.98 (m, 2H), 3.54-3.64 (m, 2H), 2.04 (br. s., 2H), 1.75 (br. s., 2H), 1.38 (s, 9H) | as Ex. 21 |

| Ex. | Structure/Name | MS (M + H)+ | NMR | Method |
|---|---|---|---|---|
| 28 | N-(6-(tert-butylsulfonyl)-7-(2-chloroethoxy)quinazolin-4-yl)benzo[d]thiazol-5-amine | 477, 479 | $^1$H NMR (DMSO-d$_6$) δ: 11.44 (br. s., 1H), 9.47 (s, 1H), 9.26 (s, 1H), 8.82 (s, 1H), 8.49 (d, J = 1.8 Hz, 1H), 8.25 (d, J = 8.8 Hz, 1H), 7.82 (dd, J = 8.7, 1.9 Hz, 1H), 7.43 (s, 1H), 4.55-4.63 (m, 2H), 4.00-4.09 (m, 2H), 1.38 (s, 9H) | as Ex. 21 |
| 29 | (R)-1-((4-(benzo[d]thiazol-5-ylamino)-6-(tert-butylsulfonyl)quinazolin-7-yl)oxy)propan-2-ol | 473 | $^1$H NMR (400 MHz, DMSO-d6) δ ppm 10.56 (s, 1H), 9.43 (s, 1H), 9.15 (s, 1H), 8.64 (s, 1H), 8.59 (d, J = 2.0 Hz, 1H), 8.17 (d, J = 8.7 Hz, 1H), 7.89 (dd, J = 8.7, 2.0 Hz, 1H), 7.38 (s, 1H), 4.81 (d, J = 4.0 Hz, 1H), 4.0-4.18 (m, 2H), 3.17 (d, J = 5.5 Hz, 1H), 1.36 (s, 9H), 1.26 (d, J = 5.5 Hz, 3H) | as Ex. 21 |
| 30 | N-(6-(tert-butylsulfonyl)-7-propoxyquinazolin-4-yl)benzo[d]thiazol-5-amine | 457 | $^1$H NMR (400 Hz, DMSO-d6) δ ppm 10.51-10.62 (m, 1H), 9.38-9.47 (m, 1H), 9.07-9.20 (m, 1H), 8.62-8.68 (m, 1H), 8.53-8.61 (m, 1H), 8.09-8.23 (m, 1H), 7.86-7.94 (m, 1H), 7.31-7.41 (m, 1H), 4.13-4.24 (m, 2H), 1.75-1.89 (m, 2H), 1.07 (t, J = 7.45 Hz, 3H) | as Ex. 21 |
| 31 | N-(6-(tert-butylsulfonyl)-7-(2-(methylthio)ethoxy)quinazolin-4-yl)benzo[d]thiazol-5-amine | 488 | $^1$H NMR (400 MHz, CHLOROFORM-d) δ ppm 9.07 (s, 1H), 8.76 (s, 1H), 8.58-8.69 (m, 1H), 8.14 (s, 1H), 8.00 (d, J = 8.6 Hz, 1H), 7.77 (dd, J = 8.6, 2.0 Hz, 1H), 7.35 (s, 1H), 7.28 (s, 1H), 4.36 (t, J = 7.2 Hz, 2H), 3.02 (t, J = 7.2 Hz, 2H), 2.24 (s, 3H), 1.45 (s, 9H) | as Ex. 21 |

| Ex. | Structure/Name | MS (M + H)+ | NMR | Method |
|---|---|---|---|---|
| 32 | N-(7-(2-bromoethoxy)-6-(tert-butylsulfonyl)quinazolin-4-yl)benzo[d]thiazol-5-amine | 521 | ¹H NMR (400 MHz, DMSO-d6) δ ppm 10.58 (s, 1H), 9.42 (s, 1H), 9.16 (s, 1H), 8.64 (s, 1H), 8.59 (s, 1H), 8.17 (d, J = 8.7 Hz, 1H), 7.89 (d, J = 8.7 Hz, 1H), 7.43 (s, 1H), 4.64 (t, J = 5.31 Hz, 2H), 3.76-3.90 (m, 2H), 1.36 (m, 9H) | as Ex. 21 |

Example 33

4-(benzo[d]thiazol-5-ylamino)-6-(tert-butylthio)quinazolin-7-ol

Example 34

N-(6-(tert-butylthio)-7-isopropoxyquinazolin-4-yl)benzo[d]thiazol-5-amine

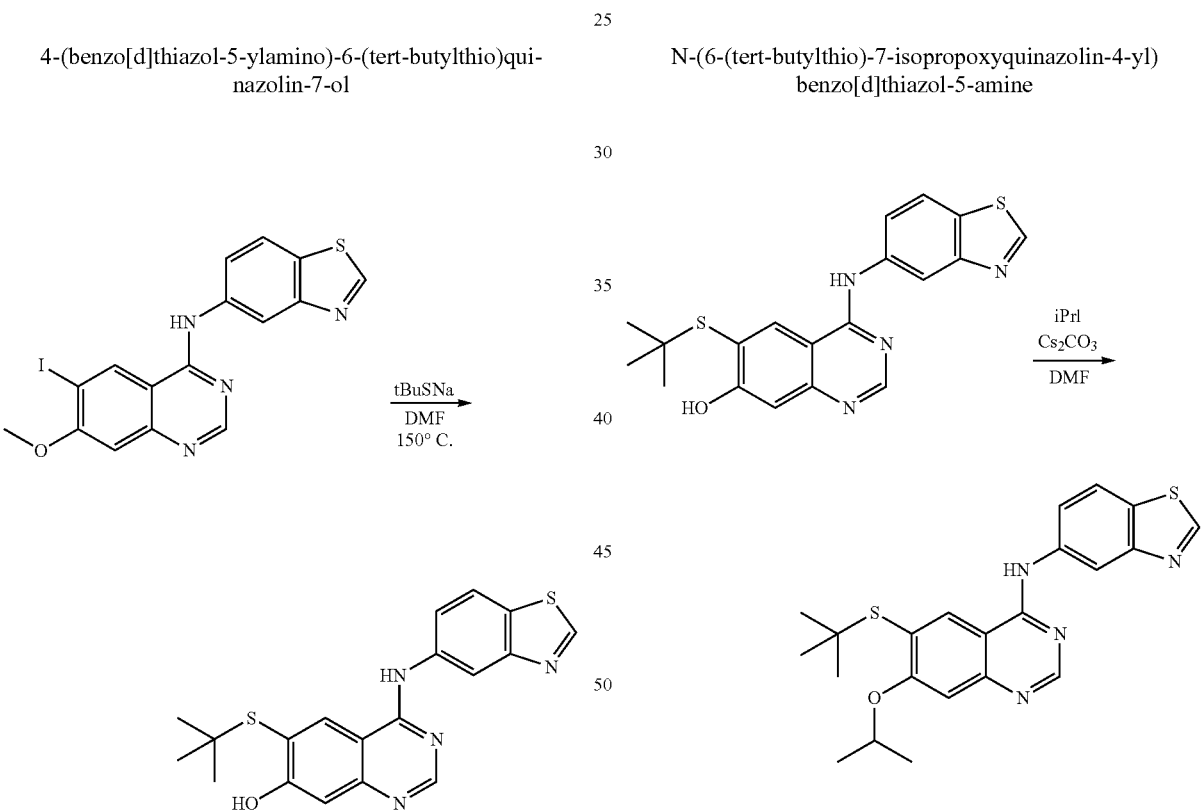

To a solution of N-1,3-benzothiazol-5-yl-6-iodo-7-(methyloxy)-4-quinazolinamine (100 mg, 0.23 mmol) in DMF (2 mL) was added sodium 2-methyl-2-propanethiolate (258 mg, 2.30 mmol). The reaction mixture was stirred at 150° C. for 3 days. The solvent was evaporated under vacuum and crude material was purified by column chromatography to provide 45 mg of the title compound (49%). MS: m/z: 383 [M+H]+.

To a solution of 4-(1,3-benzothiazol-5-ylamino)-6-[(1,1-dimethylethyl)thio]-7-quinazolinol (25 mg, 0.065 mmol) and Cs₂CO₃ (63.9 mg, 0.20 mmol) in DMF (1 mL) was added 2-iodopropane (22 mg, 0.13 mmol). The solution was stirred at rt for 2 h. Solvent was removed in vacuo and the crude material was purified by column chromatography (0 to 10% MeOH/CH₂Cl₂) to provide 14 mg of the title compound (48%). MS: m/z: 425 [M+H]+. ¹H NMR (DMSO-d₆) δ: 10.04 (s, 1H), 9.41 (s, 1H), 8.84 (s, 1H), 8.70 (d, J=1.8 Hz, 1H), 8.58 (s, 1H), 8.14 (d, J=8.6 Hz, 1H), 7.94 (dd, J=8.7, 1.9 Hz, 1H), 7.23 (s, 1H), 4.90 (dt, J=12.1, 6.1 Hz, 1H), 1.38 (d, J=6.1 Hz, 6H), 1.31 (s, 9H).

Example 35

N-(6-(tert-butylsulfonyl)-7-isopropoxyquinazolin-4-yl)benzo[d]thiazol-5-amine

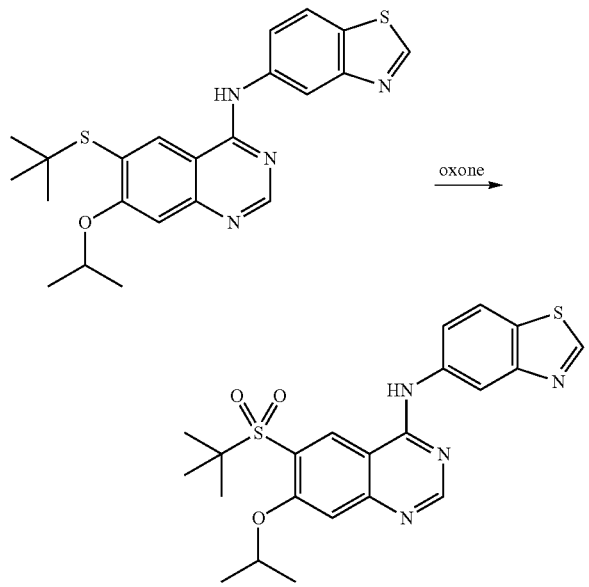

To a solution of N-1,3-benzothiazol-5-yl-6-[(1,1-dimethylethyl)thio]-7-[(1-methylethyl)oxy]-4-quinazolinamine (100 mg, 0.24 mmol) in MeOH (2 mL) and water (0.4 mL) was added oxone (290 mg, 0.47 mmol), and the reaction mixture was stirred at rt for one h. Solid was filtered out. The remaining solution was concentrated and residue was purified by HPLC and basified by carbonate cartridge to give 25 mg of the title compound 22%). MS: m/z: 457 [M+H]$^+$; $^1$H NMR (400 MHz, DMSO-$d_6$) δ 1.31 (s, 9 H), 1.38 (d, J=6.06 Hz, 6 H), 4.90 (dt, J=12.13, 6.06 Hz, 1 H), 7.23 (s, 1 H), 7.94 (dd, J=8.72, 1.89 Hz, 1 H), 8.14 (d, J=8.59 Hz, 1 H), 8.58 (s, 1 H), 8.70 (d, J=1.77 Hz, 1 H), 8.84 (s, 1 H), 9.41 (s, 1 H), 10.04 (s, 1 H)

Example 36

Ethyl 2-((4-(benzo[d]thiazol-5-ylamino)-6-(tert-butylsulfonyl)quinazolin-7-yl)oxy)-2-methylpropanoate

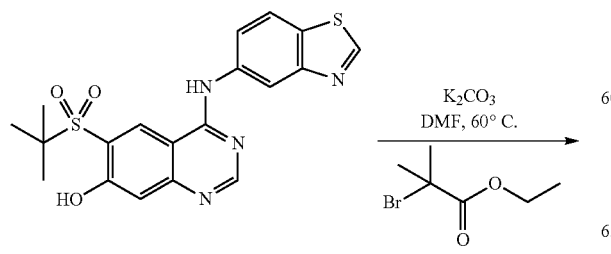

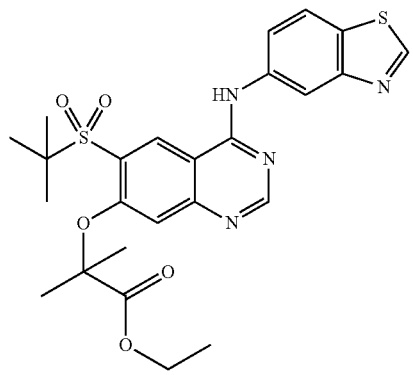

A suspension of 4-(benzo[d]thiazol-5-ylamino)-6-(tert-butylsulfonyl)quinazolin-7-ol (250 mg, 0.60 mmol) and potassium carbonate (250 mg, 1.81 mmol) in DMF (3 mL) was stirred at rt for 2 min before ethyl 2-bromo-2-methylpropanoate (99 μl, 0.66 mmol) was added, then stirred at 60° C. for 1 h. The reaction mixture was partitioned between EtOAc and water, the organic washed with satd. NH$_4$Cl and dried over MgSO$_4$ and concentrated to an oil. The residue was purified via column chromatography (30% to 100% in EtOAc in hexanes; 40 g silica gel cartridge column). The pooled fractions were concentrated in vacuo to give a white solid, ethyl 2-((4-(benzo[d]thiazol-5-ylamino)-6-(tert-butylsulfonyl)quinazolin-7-yl)oxy)-2-methylpropanoate (101 mg, 32% yield). $^1$H NMR (CHLOROFORM-d) δ: 9.06 (s, 1 H), 8.68-8.79 (m, 2 H), 8.51-8.63 (m, 1 H), 7.99 (d, J=8.6 Hz, 1 H), 7.76 (dd, J=8.6, 2.0 Hz, 1 H), 7.28 (s, 1 H), 7.15 (br. s., 1 H), 4.31 (q, J=7.1 Hz, 2 H), 1.79 (s, 6 H), 1.47 (s, 9 H), 1.28 (t, J=7.1 Hz, 3 H). MS (m/z): 529.0 (M+H$^+$).

Example 37

2-((4-(Benzo[d]thiazol-5-ylamino)-6-(tert-butylsulfonyl)quinazolin-7-yl)oxy)-2-methylpropan-1-ol

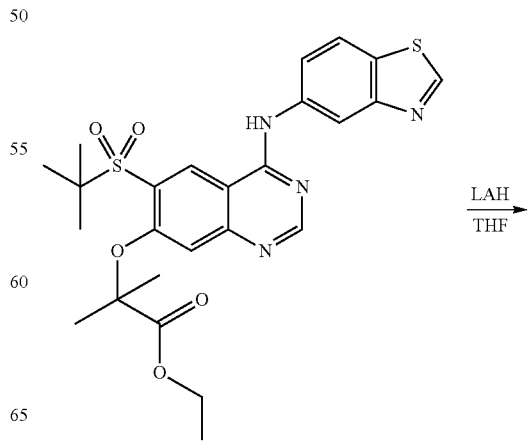

-continued

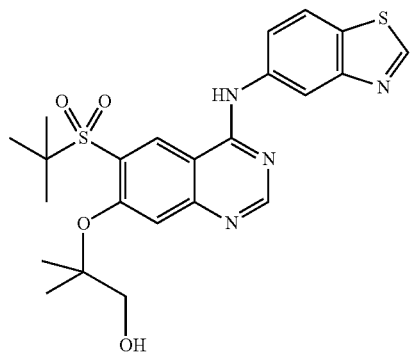

To a solution of ethyl 2-((4-(benzo[d]thiazol-5-ylamino)-6-(tert-butylsulfonyl)quinazolin-7-yl)oxy)-2-methylpropanoate (134 mg, 0.25 mmol) in THF (2.4 mL) at rt was slowly added LAH (127 μl, 0.13 mmol). After stirring for 30 m, the reaction mixture was concentrated to an oil, and preabsorbed on silica. The residue was purified via column chromatography (EtOAc to a 3:5 mixture of a 10% NH$_4$OH in IPA solution:EtOAc; 40 g silica gel cartridge column). The pooled fractions were concentrated in vacuo to give a white solid, 2-((4-(benzo[d]thiazol-5-ylamino)-6-(tert-butylsulfonyl)quinazolin-7-yl)oxy)-2-methylpropan-1-ol (43 mg, 35% yield). $^1$H NMR (CHLOROFORM-d) δ: 9.07 (s, 1 H), 8.67-8.78 (m, 2 H), 8.52-8.63 (m, 1 H), 7.97 (d, J=8.6 Hz, 1 H), 7.77 (dd, J=8.6, 1.8 Hz, 1 H), 7.59 (br. s., 1 H), 7.28 (s, 1 H), 4.04 (m, 1 H), 3.58-3.76 (m, 2 H), 1.64 (s, 6 H), 1.43 (s, 9 H). MS (m/z) 487.1 (M+H$^+$).

Example 38

N-1,3-benzothiazol-5-yl-6-[(1,1-dimethylethyl)sulfonyl]-7-ethenyl-4-quinazolinamine

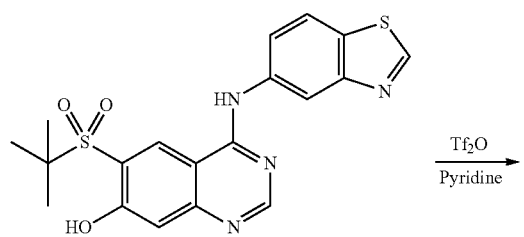

-continued

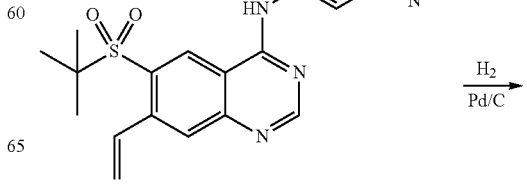

Step 1. 4-(benzo[d]thiazol-5-ylamino)-6-(tert-butylsulfonyl)quinazolin-7-yl trifluoromethanesulfonate: To an ice cooled solution of 4-(benzo[d]thiazol-5-ylamino)-6-(tert-butylsulfonyl)quinazolin-7-ol (346 mg, 0.83 mmol) in pyridine (6 mL) was slowly added triflic anhydride (421 μl, 2.50 mmol). The reaction was warmed to rt over 5 min. The reaction mixture was triturated from CH$_2$Cl$_2$. The solid residue was purified via column chromatography (10% to 100% in EtOAc in hexanes; 40 g silica gel cartridge column). The fractions were pooled and concentrated in vacuo to provide 4-(benzo[d]thiazol-5-ylamino)-6-(tert-butylsulfonyl)quinazolin-7-yl trifluoromethanesulfonate as a yellow solid (72 mg, 18% yield). $^1$H NMR (CHLOROFORM-d) δ: 9.02-9.13 (m, 1H), 8.90 (d, J=5.3 Hz, 1H), 8.77-8.85 (m, 1H), 8.58-8.66 (m, 1H), 8.15-8.25 (br. s., 1H), 8.05 (d, J=8.7 Hz, 1H), 7.95 (t, J=6.6 Hz, 1H), 7.80 (d, J=8.7 Hz, 1H), 1.44 (s, 9H). MS (m/z) 546.9 (M+H$^+$).

Step 2. N-(6-(tert-butylsulfonyl)-7-vinylquinazolin-4-yl)benzo[d]thiazol-5-amine: To a solution of 4-(benzo[d]thiazol-5-ylamino)-6-(tert-butylsulfonyl)quinazolin-7-yl trifluoromethanesulfonate (60.0 mg, 0.091 mmol) and vinyltri-n-butyltin (37.1 μl, 0.126 mmol) in DMF (1.01 mL) was added PdCl$_2$(dppf)-CH$_2$Cl$_2$ adduct (18 mg, 0.02 mmol). The reaction was heated at 150° C. for 20 min in a microwave reactor. The residue was purified via column chromatography (10% to 100% in EtOAc in hexanes; 40 g silica gel cartridge column). The fractions were pooled and concentrated in vacuo to provide N-(6-(tert-butylsulfonyl)-7-vinylquinazolin-4-yl)benzo[d]thiazol-5-amine (40 mg, 86% yield) as an oil. $^1$H NMR (DMSO-d$_6$) δ: 10.64-10.78 (m, 1H), 9.45 (s, 1H), 9.21 (s, 1H), 8.76 (s, 1H), 8.59 (d, J=2.0 Hz, 1H), 8.21 (d, J=8.6 Hz, 1H), 7.90 (dd, J=8.6, 2.0 Hz, 1H), 7.69-7.83 (m, 1H), 7.46-7.68 (m, 1H), 6.05 (d, J=17.2 Hz, 1H), 5.58 (d, J=11.9 Hz, 1H), 1.32 (s, 9H). MS (m/z) 425.0 (M+H$^+$).

Example 39

N-1,3-benzothiazol-5-yl-6-[(1,1-dimethylethyl)sulfonyl]-7-ethyl-4-quinazolinamine

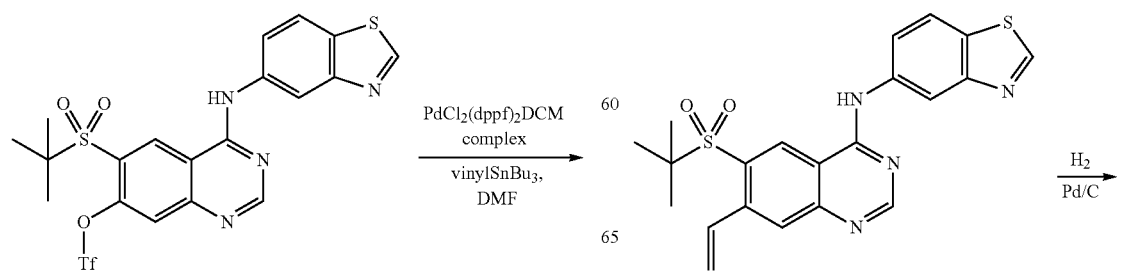

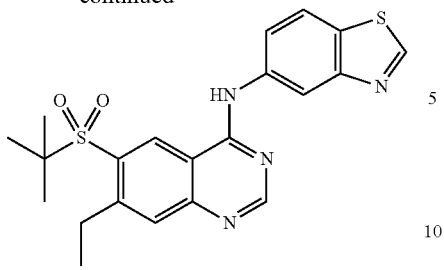

To a solution of N-(6-(tert-butylsulfonyl)-7-vinylquinazolin-4-yl)benzo[d]thiazol-5-amine (40 mg, 0.094 mmol) in EtOH/THF (9.4 mL) was added 10% Pd/C (15 mg). The solution was purged with nitrogen then hydrogenated at atmospheric pressure with a hydrogen balloon for 21 h, when another 20 mg of Pd/C was added. The reaction was hydrogenated another 4 h. Some olefin was still present in the reaction mixture. The mixture was filtered through glass filter paper and the residue was subjected to the original reaction conditions and continued hydrogenation until complete in 18 h. The reaction mixture was filtered through glass filter paper and concentrated in vacuo. The residue was purified via reverse phase chromatography (6% to 75% 0.1% TFA in MeCN in 0.1% TFA in water; Sum 30×150 mm Waters Sunfire column, 15 min gradient). The pure fraction was partitioned between EtOAc and satd. NaHCO₃, the organic layer was washed with brine, then dried over MgSO₄ and concentrated in vacuo to obtain N-(6-(tert-butylsulfonyl)-7-ethylquinazolin-4-yl)benzo[d]thiazol-5-amine (7.5 mg, 19% yield). $^1$H NMR (DMSO-$d_6$) δ: 10.67 (s, 1H), 9.42 (s, 1H), 9.18 (s, 1H), 8.69 (s, 1H), 8.57 (d, J=2.0 Hz, 1H), 8.17 (d, J=8.7 Hz, 1H), 7.91 (dd, J=8.7, 2.0 Hz, 1H), 7.82 (s, 1H), 3.20 (td, J=7.3 Hz, 2H), 1.33 (s, 9H), 1.16 (t, J=7.3 Hz, 3H). MS (m/z) 427.1 (M+H⁺).

Example 40

N-(6-(tert-butylsulfonyl)-7-chloroquinazolin-4-yl)benzo[d]thiazol-5-amine

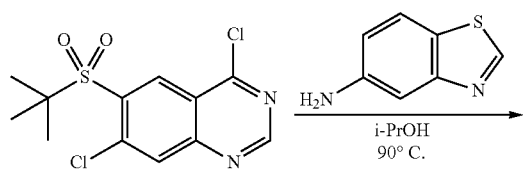

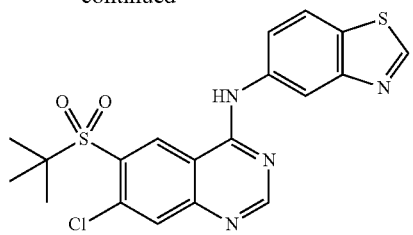

To a solution of 4,7-dichloro-6-[(1,1-dimethylethyl)sulfonyl]quinazoline (60 mg, 0.15 mmol) in N-methyl-2-pyrrolidone (1 mL) was added 1,3-benzothiazol-5-amine (27 mg, 0.18 mmol). The reaction mixture was heated at 90° C. for 20 min. The solution was allowed to cool to rt. The reaction mixture was filtered and the filtrate was purified by HPLC and free based with a carbonate SPE cartridge to provide 21 mg of the title compound (32%). MS: m/z: 433.1 [M+H]⁺. $^1$H NMR (400 MHz, DMSO-$d_6$) δ 1.24 (d, 9 H), 7.87-8.07 (m, 2 H), 8.14-8.31 (m, 2 H), 8.66 (d, J=1.77 Hz, 1 H), 8.77 (s, 1 H), 9.27 (d, J=1.52 Hz, 1 H), 9.44 (s, 1 H), 10.63 (s, 1 H).

The following compound was prepared using procedures analogous to those described above using the appropriate amine.

| Example | Structure/Name | MS (M + H)⁺ | NMR | Method |
|---|---|---|---|---|
| 41 | 6-(tert-butylsulfonyl)-7-chloro-N-(4,5-dimethyl-1H-pyrazol-3-yl)quinazolin-4-amine | 394 | $^1$H NMR (400 MHz, DMSO-$d_6$) δ 1.37 (s, 9H), 2.18 (s, 6H), 7.97 (s, 1H), 8.57 (s, 1H), 9.21 (s, 1H), 10.72 (br. s., 1H), 12.26 (br. s., 1H) | as Ex. 40 |

Example 42

6-[(1,1-dimethylethyl)sulfonyl]-N-(5-fluoro-1H-pyrazolo[3,4-b]pyridin-3-yl)-7-(methyloxy)-4-quinazolinamine

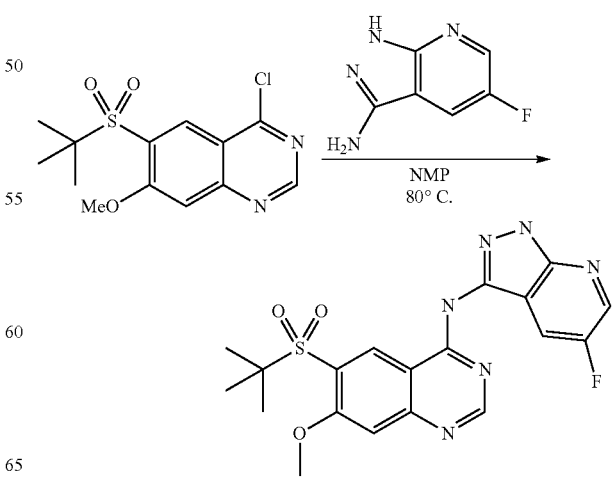

In a flask was combined 4-chloro-6-[(1,1-dimethylethyl)sulfonyl]-7-(methyloxy)quinazoline (100 mg, 0.32 mmol), 5-fluoro-1H-pyrazolo[3,4-b]pyridin-3-amine (58 mg, 0.38 mmol) in NMP (1 mL). The reaction mixture was heated at 80° C. for 1 h. The solution was allowed to cool to rt. The solid was filtered out and remaining solution was concentrated and residue was purified by HPLC to provide 20 mg of the title compound. MS:m/z: 431 [M+H]$^+$; $^1$H NMR (400 MHz, DMSO-d$_6$) δ 1.24-1.36 (s, 9 H), 3.98 (s, 3 H), 7.27 (s., 1 H), 8.02 (s, J=8.72, 2.65 Hz, 1 H), 8.42 (s, 1 H), 8.54 (s, 2 H), 9.04 (s, 1 H).

Alternatively, these reactions can be performed in EtOH with a catalytic amount of HCl.

The following compounds were prepared using procedures analogous to those described.

| Example | Structure/Name | MS (M + H)$^+$ | NMR | Method |
|---|---|---|---|---|
| 43 | 6-(tert-butylsulfonyl)-N-(4-chloro-3-methoxyphenyl)-7-methoxyquinazolin-4-amine | 436 | $^1$H NMR (DMSO-d6) δ: 10.38 (s, 1H), 9.08 (s, 1H), 8.64 (s, 1H), 7.62 (d, J = 2.0 Hz, 1H), 7.46-7.52 (m, 1H), 7.38-7.46 (m, 2H), 4.01 (s, 3H), 3.89 (s, 3H), 1.33 (s, 9H) | HCl/EtOH |
| 44 | 5-((6-(tert-butylsulfonyl)-7-methoxyquinazolin-4-yl)amino)-2-chlorophenyl | 422 | $^1$H NMR (DMSO-d6) δ: 10.30 (br. s., 1H), 9.07 (s, 1H), 8.61 (s, 1H), 7.55 (d, J = 2.0 Hz, 1H), 7.38 (s, 1H), 7.32 (d, J = 8.5 Hz, 1H), 7.22 (dd, J = 8.7, 2.1 Hz, 1H), 4.00 (s, 3H), 3.17 (s, 1H), 1.32 (s, 9H) | HCl/EtOH |
| 45 | 6-(tert-butylsulfonyl)-7-methoxy-N-(3-methyl-1H-indazol-6-yl)quinazolin-4-amine | 426 | $^1$H NMR (DMSO-d6) δ: 9.23 (s, 1H), 8.82 (s, 1H), 7.91 (s, 1H), 7.76 (d, J = 8.5 Hz, 1H), 7.44 (s, 1H), 7.38 (dd, J = 8.8, 1.5 Hz, 1H), 4.05 (s, 3H), 2.51 (s, 3H), 1.34 (s, 9H) | HCl/EtOH |
| 46 | 6-(tert-butylsulfonyl)-N-(4-chloro-2-fluorophenyl)-7-methoxyquinazolin-4-amine | 424 | $^1$H NMR (DMSO-d6) δ: 10.74 (br. s., 1H), 9.05 (s, 1H), 8.58 (br. s., 1H), 7.52-7.65 (m, 2H), 7.34-7.45 (m, 2H), 4.02 (s, 3H), 1.33 (s, 9H) | HCl/EtOH |

| Example | Structure/Name | MS (M + H)+ | NMR | Method |
|---|---|---|---|---|
| 47 | 6-(tert-butylsulfonyl)-N-(1H-indazol-6-yl)-7-methoxyquinazolin-4-amine | 412 | 1H NMR (DMSO-d6) δ: 13.03 (br. s., 1H), 10.51 (br. s., 1H), 9.14 (s, 1H), 8.65 (s, 1H), 8.14 (s, 1H), 8.05 (s, 1H), 7.76 (d, J = 8.6 Hz, 1H), 7.48 (dd, J = 8.6, 1.3 Hz, 1H), 7.39 (s, 1H), 4.01 (s, 3H), 1.33 (s, 9H) | HCl/EtOH |

Example 48

6-(tert-butylsulfonyl)-N-(4,5-dimethyl-1H-pyrazol-3-yl)-7-methoxyquinazolin-4-amine In a flask was combined 6-[(1,1-dimethylethyl)sulfonyl]-7-(methyloxy)-4(1H)-quinazolinone (60 mg, 0.20 mmol) and POCl₃ (2 mL, 21.5 mmol), and the reaction mixture was heated at 80° C. for 4 h. The solution was allowed to cool to rt. POCl₃ was removed under high vacuum. The residue was treated with satd. aq. NaHCO₃ and extracted with CH₂Cl₂. The organic extract was dried over Na₂SO₄. The solvent was removed and crude material was dissolved in NMP (1 mL) followed by addition of 4,5-dimethyl-1H-pyrazol-3-amine (27 mg, 0.24 mmol). The reaction mixture was heated at 80° C. for 1 h. The solution was allowed to cool to rt. The solid was filtered out and the remaining solution was concentrated and residue was purified by HPLC to provide 6.0 mg of the title compound. MS (m/z): 390 (M+H); ¹H NMR (400 MHz, DMSO-d₆) δ 1.30 (s, 9 H), 2.21 (s, 6 H), 4.00 (s, 3 H), 7.91 (s, 1 H), 8.65 (s, 1 H), 9.11 (s, 1 H), 10.19 (br. s., 1 H), 12.32 (br. s., 1 H).

Example 49

(E)-3-(4-(benzo[d]thiazol-5-ylamino)-6-(tert-butyl-sulfonyl)quinazolin-7-yl)prop-2-en-1-ol

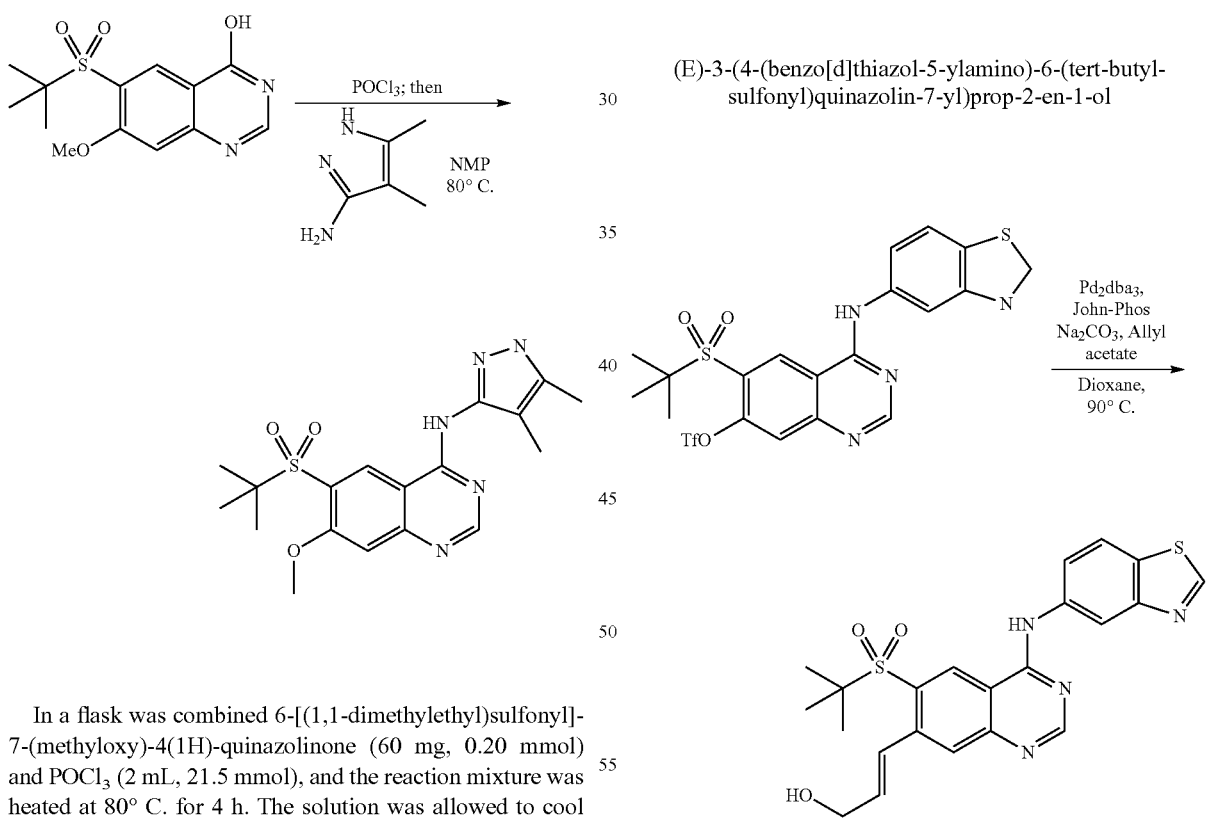

To a vial was added 4-(benzo[d]thiazol-5-ylamino)-6-(tert-butylsulfonyl)quinazolin-7-yl trifluoromethanesulfonate (820 mg, 1.50 mmol), Pd₂dba₃ (137 mg, 0.15 mmol), tri-tert-butylphosphine, tetrafluoroborate (87 mg, 0.30 mmol), and sodium carbonate (318 mg, 3.00 mmol). The vial was evacuated and backfilled with nitrogen three times before 1,4-dioxane (15 mL) and allyl acetate (0.24 mL, 2.25 mmol) were added. The reaction was heated to 90° C. for three days. Upon completion, it was cooled to rt and concentrated. The residue was then passed through a C13 SPE cartridge but no separation was observed. Fractions collected were combined, concentrated, and purified by RP HPLC to afford the desired product (78 mg, 10%). $^1$H NMR (DMSO-d6) d 9.35 (s, 1H), 8.61 (br. s., 1H), 8.10-8.22 (m, 1H), 8.04 (d, J=8.3 Hz, 1H), 7.85-7.96 (m, 1H), 7.35 (br. s., 1H), 6.20 (s, 1H), 5.86-6.07 (m, 1H), 5.28 (s, 1H), 5.25 (d, J=5.0 Hz, 1H), 4.63 (br. s., 1H), 1.32 (s, 9H); MS (m/z) 455.1 (M+H$^+$).

Example 50

2-((4-(benzo[d]thiazol-5-ylamino)-7-methoxyquinazolin-6-yl)sulfonyl)ethanol

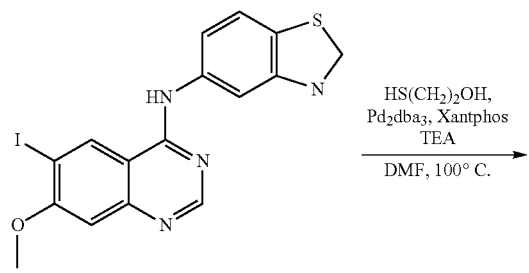

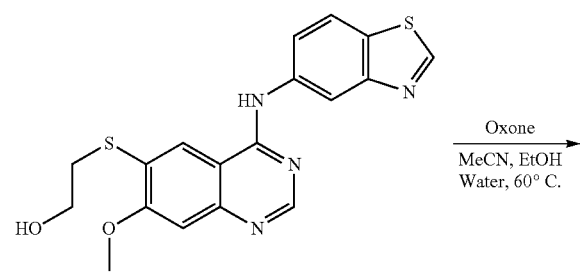

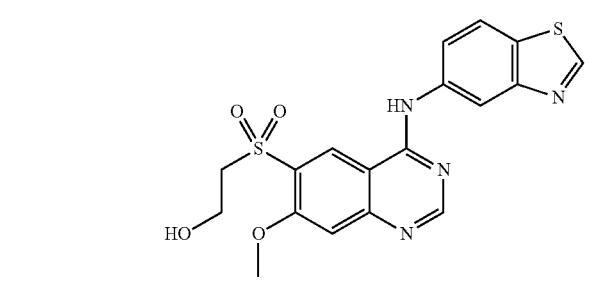

Step 1. 2-((4-(benzo[d]thiazol-5-ylamino)-7-methoxyquinazolin-6-yl)thio)ethanol: To a flask was added N-(6-iodo-7-methoxyquinazolin-4-yl)benzo[d]thiazol-5-amine (1 g, 2.30 mmol), Pd$_2$dba$_3$ (0.21 g, 0.23 mmol), and Xantphos (0.13 g, 0.23 mmol) which was then evacuated and backfilled with nitrogen three times before DMF (15 ml), TEA (0.96 ml, 6.91 mmol), and mercaptoethanol (0.17 ml, 2.42 mmol) were added. The reaction was heated to 100° C. overnight. It was then cooled to rt and partially concentrated. The resulting residue was titurated with MeOH. A minimal amount of solid precipitated which was filtered to give a dark green residue. The filtrate was then diluted with ether (100 mL) but no solid formed. The solution sat for three days at rt. A suspension was observed which was filtered and the cake was washed with ether to give the desired product as a yellow solid (603 mg, 65%). MS (m/z) 385.1 (M+H$^+$).

Step 2. 2-((4-(benzo[d]thiazol-5-ylamino)-7-methoxyquinazolin-6-yl)sulfonyl)ethanol: 2-((4-(benzo[d]thiazol-5-ylamino)-7-methoxyquinazolin-6-yl)thio)ethanol (603 mg, 1.57 mmol) was taken up in acetonitrile (10 mL), ethanol (10 mL), and water (10 mL) before oxone (2.89 g, 4.71 mmol) was added. The reaction was stirred at rt for 6 hours. It was then diluted with sat aq NaHCO$_3$ (100 mL), and extracted using DCM (2×200 mL). The combined organics were dried over sodium sulfate, filtered through celite, and concentrated. The aqueous layer was a suspension so it was filtered to give a second crop of material which was more pure than the material from the concentrated organics. The second crop of material was dissolved in 1 mL of DMSO and purified by RP HPLC (10->50% MeCN in water with 0.1% TFA) on a 5 µM C18 OBD Sunfire 30×100 mm. Desired fractions were combined and concentrated to afford the product as a yellowish solid (33 mg, 17%). 1H NMR (DMSO-d6) δ 11.27 (br. s., 1H), 9.45 (s, 1H), 9.21 (s, 1H), 8.80 (s, 1H), 8.54 (d, J=1.8 Hz, 1H), 8.22 (d, J=8.6 Hz, 1H), 7.84 (dd, J=8.7, 1.9 Hz, 1H), 7.45 (s, 1H), 4.12 (s, 3H), 3.63-3.84 (m, 4H), 2.55 (s, 1H); MS (m/z) 417.1 (M+H$^+$).

Example 51

(R)-methyl 2-((4-(benzo[d]thiazol-5-ylamino)-6-(tert-butylsulfonyl)quinazolin-7-yl)oxy)propanoate and (S)-Methyl 2-((4-(benzo[d]thiazol-5-ylamino)-6-(tert-butylsulfonyl)quinazolin-7-yl)oxy)propanoate

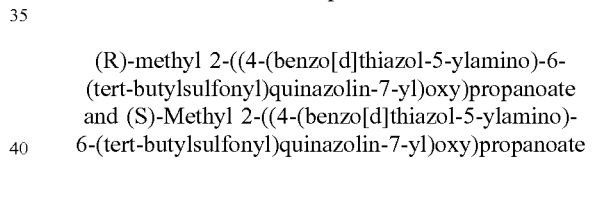

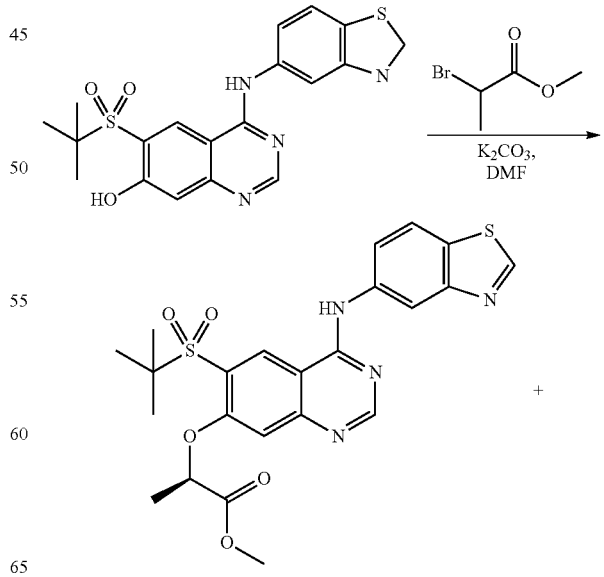

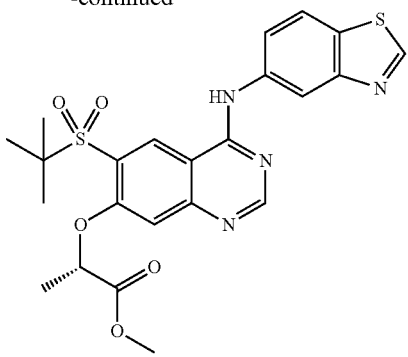

A suspension of 4-(benzo[d]thiazol-5-ylamino)-6-(tert-butylsulfonyl)quinazolin-7-ol (0.50 g, 1.21 mmol) and potassium carbonate (0.50 g, 3.62 mmol) in N,N-Dimethylformamide (DMF) (6.3 ml) was stirred for 2 minutes before methyl 2-bromopropanoate (0.15 ml, 1.57 mmol) was added. The reaction was heated for 1 h at 70° C. The reaction was cooled and water (20 mL) was added. The product was filtered out as a yellow solid and let dry, then triturated with 5 mL MeOH. Methyl 2-((4-(benzo[d]thiazol-5-ylamino)-6-(tert-butylsulfonyl)quinazolin-7-yl)oxy)propanoate (350 mg, 58% yield) was filtered out. The racemic mixture was resolved (Chiralpak AD-H column, 60% EtOH in hexanes with 0.1% DIEA), separating a faster eluting isomer ($R_t$=8.6 min) and a slower eluting isomer ($R_t$=13.5 min).

Each enantiomer was isolated by evaporation of solvent (R and S)-methyl 2-((4-(benzo[d]thiazol-5-ylamino)-6-(tert-butylsulfonyl)quinazolin-7-yl)oxy)propanoate (115 mg each, combined yield: 38%). $^1$H NMR (400 MHz, DMSO-$d_6$) δ ppm 10.58 (s, 1 H), 9.42 (s, 1 H), 9.18 (s, 1 H), 8.62 (s, 1 H), 8.58 (d, J=1.77 Hz, 1 H), 8.17 (d, J=8.59 Hz, 1 H), 7.77-7.97 (m, 1 H), 7.14 (s, 1 H), 5.32-5.50 (m, 1 H), 3.74 (s, 3 H), 1.61 (d, J=6.57 Hz, 3 H), 1.40 (s, 9 H). LC/MS: M+H 501.2

The racemate was made in an analogous method without the resolution.

| Example | Structure/Name | MS (M + H)$^+$ | NMR | Method |
|---|---|---|---|---|
| 52 | 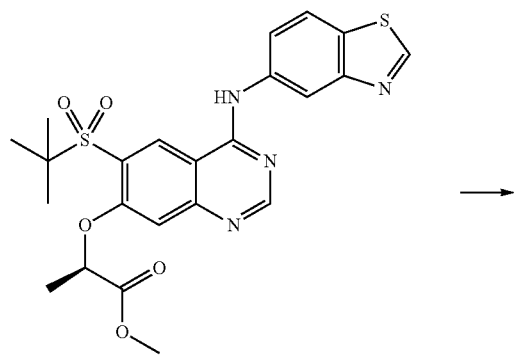<br>methyl 2-((4-(benzo[d]thiazol-5-ylamino)-6-(tert-butylsulfonyl)quinazolin-7-yl)oxy)propanoate | 501 | $^1$H NMR (400 MHz, DMSO-$d_6$) δ ppm 10.58 (s, 1H), 9.42 (s, 1H), 9.18 (s, 1H), 8.62 (s, 1H), 8.58 (d, J = 1.77 Hz, 1H), 8.17 (d, J = 8.59 Hz, 1H), 7.77-7.97 (m, 1H), 7.14 (s, 1H), 5.32-5.50 (m, 1H), 3.74 (s, 3H), 1.61 (d, J = 6.57 Hz, 3H), 1.40 (s, 9H) | As Ex. 51 |

Example 53

(R)-2-((4-(benzo[d]thiazol-5-ylamino)-6-(tert-butylsulfonyl)quinazolin-7-yl)oxy)propan-1-ol (depicted) and (S)-2-((4-(benzo[d]thiazol-5-ylamino)-6-(tert-butylsulfonyl)quinazolin-7-yl)oxy)propan-1-ol

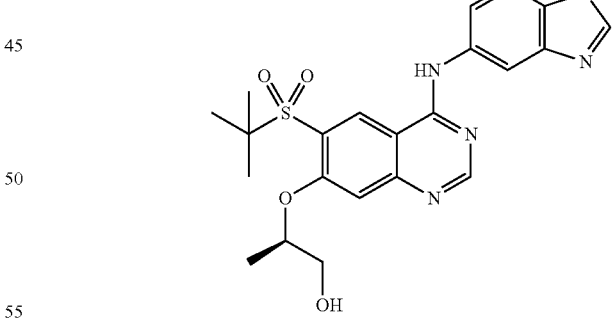

To a solution of (R or S)-methyl 2-((4-(benzo[d]thiazol-5-ylamino)-6-(tert-butylsulfonyl)quinazolin-7-yl)oxy)propanoate (110 mg, 0.22 mmol) in THF (2 mL) was added lithium aluminum hydride (220 μl, 0.22 mmol, 1M in THF; or 110 μl, 0.11 mmol, 1M in THF). The reaction was stirred at 25° C. An orange precipitate was immediately formed and the product was filtered. The solid was dissolved in 1.5 mL DMSO. The solution was filtered and the product was purified via Gilson reverse phase chromatography (8% to 70% 0.1% TFA in MeCN in 0.1% TFA in water or 8% to 60% 0.1% TFA in MeCN in 0.1% TFA in water; Sum 30×150 mm Waters Sunfire column). Pure fractions were collected and partitioned between EtOAc and water/saturated sodium bicarbonate. The organic layer was separated, dried over sodium sulfate, and evaporated in vacuo to give (R or S)-2-((4-(benzo[d]thiazol-5-ylamino)-6-(tert-butylsulfonyl)quinazolin-7-yl)oxy)propan-1-ol as a white solid.

Enantiomer 1 (prepared from the slower eluting isomer of Example 51): $^1$H NMR (400 MHz, CHLOROFORM-d) δ ppm 9.08 (s, 1 H), 8.77 (s, 1 H), 8.64 (m, 2 H), 8.06 (br. s., 1 H), 8.02 (d, J=8.6 Hz, 1 H), 7.78 (dd, J=8.6, 2.0 Hz, 1 H), 7.43 (s, 1 H), 4.73 (d, J=4.0 Hz, 2 H), 3.79 (t, J=4.4 Hz, 3 H), 3.61-3.72 (m, 1 H), 1.49 (s, 9 H). LC/MS: 473.2

Enantiomer 2 (prepared from the faster eluting isomer of Example 51): $^1$H NMR (400 MHz, CHLOROFORM-d) δ ppm 9.08 (s, 1 H), 8.77 (s, 1 H), 8.64 (s, 1 H), 8.48 (s, 1 H), 8.13 (br. s., 1 H), 8.02 (d, J=8.6 Hz, 1 H), 7.78 (dd, J=8.6, 2.0 Hz, 1 H), 7.43 (s, 1 H), 4.73 (d, J=4.0 Hz, 2 H), 3.79 (t, J=4.4 Hz, 3 H), 3.61-3.72 (m, 1 H), 1.49 (s, 9 H). LC/MS: 473.2

The racemate was made in an analogous fashion.

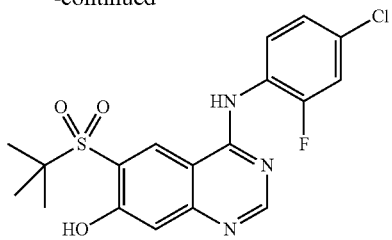

6-(tert-Butylsulfonyl)-4-(ethylthio)quinazolin-7-ol (144 mg, 0.44 mmol) and 4-chloro-2-fluoroaniline (0.49 mL, 4.4 mmol) were combined with one drop of HCl and heated to 150° C. in the microwave for 20 minutes. After cooling to rt, the mixture was diluted with ether and filtered. The solid ppt was taken up in MeOH (5 mL) and treated with MP carbonate resin (400 mg, 3 eq. @ 3.28 mmol/gram loading). The beads were filtered and the mother liquor concentrated and purified on silica gel (0 to 100% EtOAc followed by 0 to 10% MeOH/DCM). Fractions containing product were combined and concentrated to provide 2 mg of the desired product (1.1%). $^1$H NMR (DMSO-d6) δ: 10.37 (s, 1H), 8.96 (s, 1H), 8.43 (s, 1H), 7.49-7.61 (m, 2H), 7.35 (d, J=8.8 Hz, 1H), 7.20 (s, 1H), 1.34 (s, 9H); MS (m/z) 410.2, 412.0 (M+H$^+$).

| Example | Structure/Name | MS (M + H)$^+$ | NMR | Method |
|---|---|---|---|---|
| 54 | 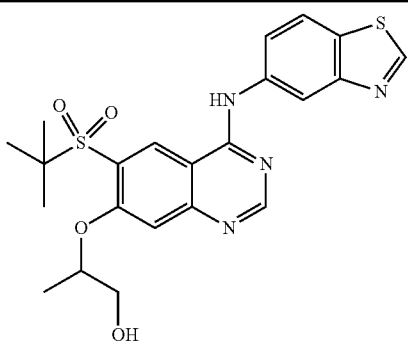<br>2-((4-(benzo[d]thiazol-5-ylamino)-6-(tert-butylsulfonyl)quinazolin-7-yl)oxy)propan-1-ol | 473 | $^1$H NMR (METHANOL-d$_4$) δ: 9.31 (s, 1H), 9.11 (s, 1H), 8.60 (s, 1H), 8.57 (d, J = 1.8 Hz, 1H), 8.12 (d, J = 8.7 Hz, 1H), 7.90 (dd, J = 8.7, 1.8 Hz, 1H), 7.44 (s, 1H), 3.75-3.84 (m, 2H), 2.70 (m, 3H), 2.16-2.22 (m, 1H), 1.48 (s, 9H) | As Ex. 54 |

Example 55

6-(tert-butylsulfonyl)-4-((4-chloro-2-fluorophenyl)amino)quinazolin-7-ol

Example 56

N-(6-(tert-butylsulfinyl)-7-methoxyquinazolin-4-yl)benzo[d]thiazol-5-amine

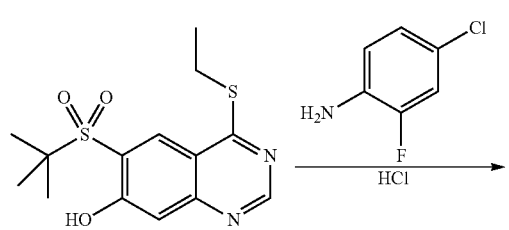

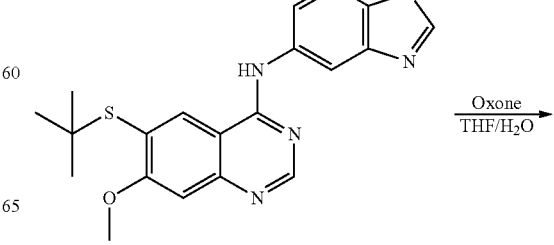

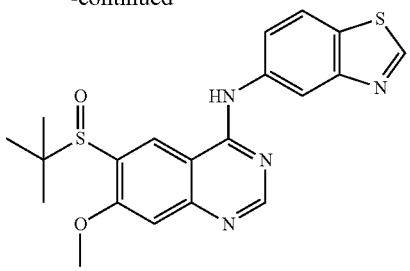

A mixture of N-(6-(tert-butylthio)-7-methoxyquinazolin-4-yl)benzo[d]thiazol-5-amine (106 mg, 0.27 mmol) and oxone (36 mg, 0.06 mmol) was stirred for 15 min in 1:1 THF:water (2.6 mL) The reaction was quenched with saturated sodium bicarbonate. The resulting orange solid was filtered, dissolved in 30 mL of 1:1 DCM:MeOH and preabsorbed onto silica gel. The product was purified by column chromatography (Isco CombiFlash, 75% to 100% EtOAc/Hexanes to 10% NH$_4$OH in MeOH). The pure fractions were concentrated in vacuo and the residue was purified via Gilson reverse phase chromatography (10% to 75% of 0.1% TFA in MeCN in 0.1% TFA in water; Sum 30×150 mm Waters Sunfire column). The pure fractions were partitioned between EtOAc and aqueous saturated sodium bicarbonate. The organic layer was separated, dried over sodium sulfate, and concentrated in vacuo to give N-(6-(tert-butylsulfinyl)-7-methoxyquinazolin-4-yl)benzo[d]thiazol-5-amine as a white solid (40 mg, 36% yield). $^1$H NMR (400 MHz, DMSO-d$_6$) δ ppm 10.46 (s, 1 H) 9.41 (s, 1 H) 8.88 (s, 1 H) 8.62 (d, J=2.0 Hz, 1H) 8.61 (s, 1 H) 8.15 (d, J=8.6 Hz, 1 H) 7.92 (dd, J=8.34, 2.53 Hz, 1 H) 7.33 (s, 1 H) 3.99 (s, 3 H) 1.19 (s, 9 H). MS (m/z) 413.2 (M+H$^+$).

Example 57

2-((4-(Benzo[d]thiazol-5-ylamino)-6-(tert-butylsulfonyl)quinazolin-7-yl)oxy)acetamide

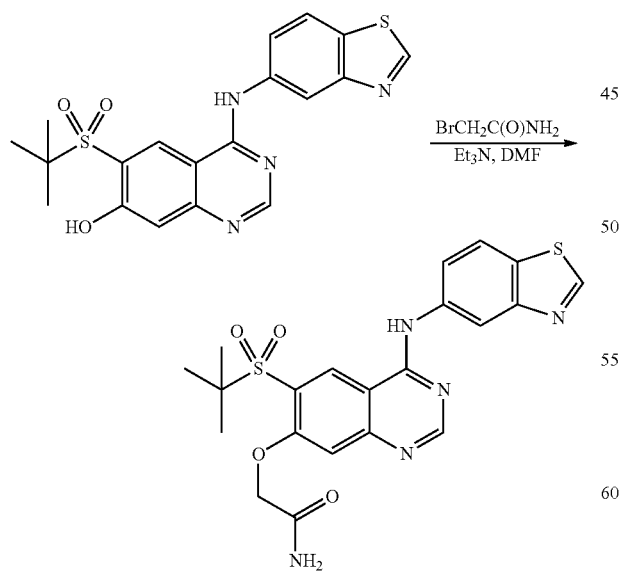

A solution of 4-(benzo[d]thiazol-5-ylamino)-6-(tert-butylsulfonyl)quinazolin-7-ol (50.0 mg, 0.121 mmol) and triethylamine (12 mg, 0.12 mmol) in DMF (0.63 mL)) was stirred 2 minutes before 2-bromoacetamide (17 mg, 0.12 mmol) was added. Little reaction occurred after heating to 70° C. Solid NaH (15 mg, 0.63 mmol) was added and the reaction was heated at 100° C. for 18 h. The reaction mixture was filtered and the filtrate was purified via Gilson reverse phase chromatography (6% to 75% of 0.1% TFA in MeCN in 0.1% TFA in water; Sum 30×150 mm Waters Sunfire column). The pure fractions were combined and evaporated to dryness, to yield 2-((4-(benzo[d]thiazol-5-ylamino)-6-(tert-butylsulfonyl)quinazolin-7-yl)oxy)acetamide (13 mg, 23% yield) as a yellow solid. 1H NMR (400 MHz, METHANOL-d4) δ ppm 9.38 (s, 1 H), 9.27 (s, 1 H), 8.80 (s, 1 H), 8.43 (d, J=1.8 Hz, 1 H), 8.23 (d, J=8.6 Hz, 1 H), 7.81 (dd, J=8.6, 1.77 Hz, 1 H), 7.21 (s, 1 H), 5.26 (s, 2 H), 1.48 (s, 9 H); MS (m/z) 471.9 (M+H$^+$).

Example 58

2-((4-(Benzo[d]thiazol-5-ylamino)-6-(tert-butylsulfonyl)quinazolin-7-yl)oxy)acetic acid

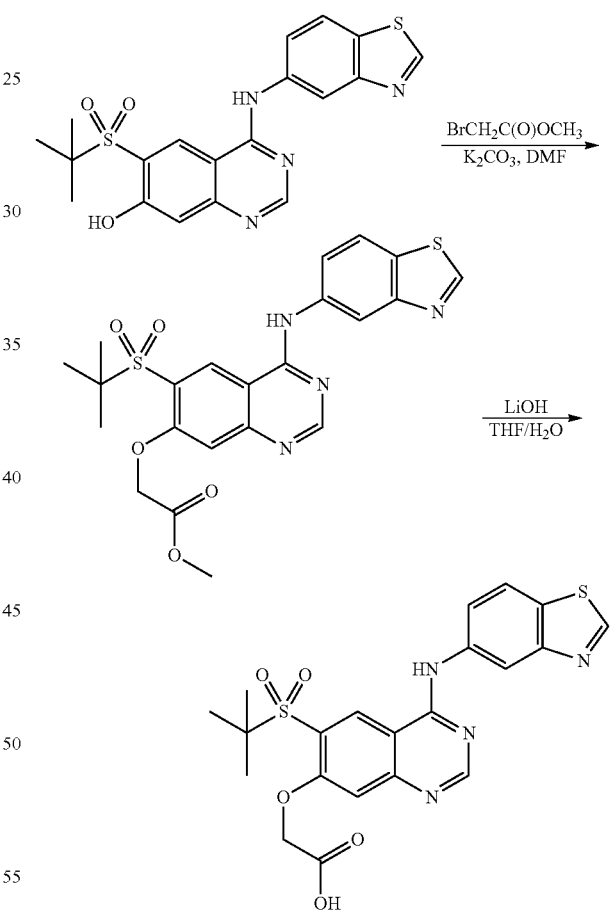

Step 1. Methyl 2-((4-(benzo[d]thiazol-5-ylamino)-6-(tert-butylsulfonyl)quinazolin-7-yl)oxy)acetate: A suspension of 4-(benzo[d]thiazol-5-ylamino)-6-(tert-butylsulfonyl)quinazolin-7-ol (350 mg, 0.84 mmol) and potassium carbonate (350 mg, 2.5 mmol) in DMF (4.4 mL) was stirred 2 minutes before adding methyl 2-bromoacetate (108 μl, 1.14 mmol). The reaction was heated at 25° C. for 6 h. The mixture was added to 15 mL water, and a yellow solid was collected by filtration and triturated with 6 mL MeOH to a thick white precipitate. The solid was filtered out to give methyl 2-((4-

(benzo[d]thiazol-5-ylamino)-6-(tert-butylsulfonyl)quinazolin-7-yl)oxy)acetate (200 mg, 49% yield). $^1$H NMR (400 MHz, DMSO-$d_6$) δ ppm 10.56-10.61 (m, 1 H), 9.43 (s, 1 H), 9.17 (s, 1 H), 8.63 (s, 1 H), 8.57 (d, J=1.8 Hz, 1 H), 8.16 (d, J=8.6 Hz, 1 H), 7.88 (dd, J=8.6, 1.8 Hz, 1 H), 3.75 (s, 2 H), 1.38 (s, 9 H), 1.34 (s, 3 H); MS (m/z) 487.2 (M+H$^+$).

Step 2. 2-((4-(benzo[d]thiazol-5-ylamino)-6-(tert-butylsulfonyl)quinazolin-7-yl)oxy)acetic acid: To a solution of methyl 2-((4-(benzo[d]thiazol-5-ylamino)-6-(tert-butylsulfonyl)quinazolin-7-yl)oxy)acetate (115 mg, 0.24 mmol) in THF (3.5 mL) was added LiOH (11 mg, 0.47 mmol) in water (1.2 mL) at 25° C. After 1 h, the reaction was concentrated to remove the THF. The residue was purified via Gilson reverse phase chromatography (10% to 60% of 0.1% TFA in MeCN in 0.1% TFA in water; Sum 30×150 mm Waters Sunfire column). The pooled fractions were concentrated to dryness in vacuo to provide 2-((4-(benzo[d]thiazol-5-ylamino)-6-(tert-butylsulfonyl)quinazolin-7-yl)oxy)acetic acid (29 mg, 26% yield) as a white solid. $^1$H NMR (400 MHz, DMSO-$d_6$) δ ppm 9.46 (s, 1 H), 9.22-9.27 (m, 1 H), 8.72-8.79 (m, 1 H), 8.47-8.56 (m, 1 H), 8.23 (d, J=8.3 Hz, 1 H), 7.83 (d, J=9.8 Hz, 1 H), 7.26 (s, 1 H), 5.08 (s, 2 H), 1.39 (s, 9 H); MS (m/z) 473.2 (M+H$^+$).

Example 59

N-(6-(tert-butylsulfonyl)-7-(2-(methylsulfonyl)ethoxy)quinazolin-4-yl)benzo[d]thiazol-5-amine

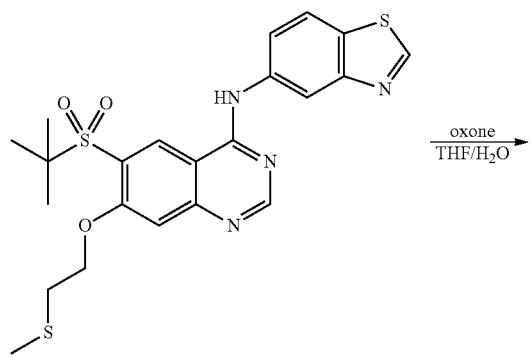

oxone
THF/H$_2$O

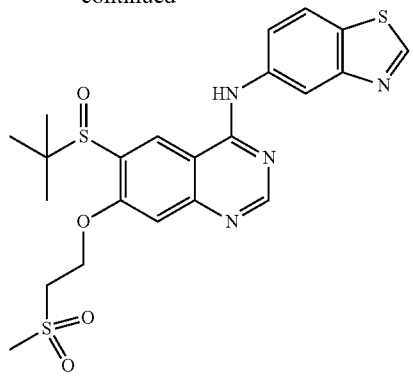

A solution of N-(6-(tert-butylsulfonyl)-7-(2-(methylthio)ethoxy)quinazolin-4-yl)benzo[d]thiazol-5-amine (30 mg, 0.061 mmol) in 1:1 THF: H$_2$O (0.6 mL) was stirred 25 minutes with oxone (113 mg, 0.18 mmol) at 25° C. The reaction mixture was partitioned between EtOAc and aqueous saturated sodium bicarbonate. The organic layer was separated, dried over sodium sulfate and evaporated in vacuo to yield N-(6-(tert-butylsulfonyl)-7-(2-(methylsulfonyl)ethoxy)quinazolin-4-yl)benzo[d]thiazol-5-amine (12.4, 39% yield). $^1$H NMR (400 MHz, DMSO-$d_6$) δ ppm 10.57-10.65 (m, 1 H), 9.38-9.51 (m, 1 H), 9.09-9.24 (m, 1 H), 8.65-8.74 (m, 1 H), 8.54-8.62 (m, 1 H), 8.09-8.22 (m, 1 H), 7.81-7.95 (m, 1 H), 7.46-7.56 (m, 1 H), 4.56-4.71 (m, 2 H), 3.64-3.75 (m, 2 H), 3.21 (s, 3 H), 1.29-1.40 (m, 9 H); MS (m/z) 521.1 (M+H$^+$).

The following compounds were prepared using procedures analogous to those described in examples 21 and 60 using the appropriate thiol.

| Example | Structure/Name | MS (M + H)$^+$ | NMR | Method |
| --- | --- | --- | --- | --- |
| 60 | N-(6-(tert-butylsulfonyl)-7-(2-(isopropylsulfonyl)ethoxy)quinazolin-yl)benzo[d]thiazol-5-amine | 549 | $^1$H NMR (400 MHz, DMSO-d6) δ ppm 10.60 (s, 1H), 9.43 (s, 1H), 9.16 (s, 1H), 8.66 (s, 1H), 8.59 (d, J = 2.0 Hz, 1H), 8.18 (d, J = 8.6 Hz, 1H), 7.86-7.93 (m, 1H), 7.52 (s, 1H), 4.64 (t, J = 5.6 Hz, 2H), 3.63-3.73 (m, 2H), 3.63 (m, 1H), 1.40 (s, 9H), 1.30 (dd, J = 7.1 Hz, 6H) | As ex. 90 |

Example 61

(E)-methyl 3-((4-(benzo[d]thiazol-5-ylamino)-6-(tert-butylsulfonyl)quinazolin-7-yl)oxy)acrylate

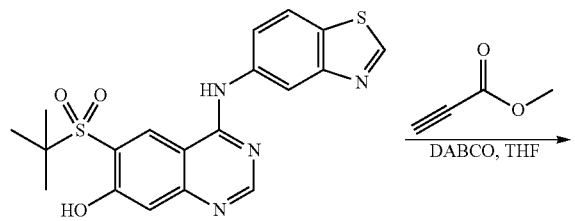

A suspension of 4-(benzo[d]thiazol-5-ylamino)-6-(tert-butylsulfonyl)quinazolin-7-ol (200 mg, 0.48 mmol) and DABCO (5 mg, 0.05 mmol) in THF (4.8 mL) was stirred 2 minutes at 25° C. before adding methyl propiolate (41 mg, 0.48 mmol). After 10 minutes, the reaction mixture was partitioned between EtOAc and aqueous saturated sodium bicarbonate and back extracted with DCM. The combined organics were dried over sodium sulfate and evaporated in vacuo. The residue was purified via column chromatography (Isco CombiFlash 50% to 100% in EtOAc in Hexanes; 40 g silica gel cartridge column). The pure fractions were concentrated in vacuo to give (E)-methyl 3-((4-(benzo[d]thiazol-5-ylamino)-6-(tert-butylsulfonyl) quinazolin-7-yl)oxy)acrylate (115 mg, 48% yield) as a white solid. $^1$H NMR (400 MHz, CHLOROFORM-d) δ ppm 9.09 (s, 1 H), 8.83 (s, 1 H), 8.69 (s, 1 H), 8.64 (d, J=2.0 Hz, 1 H), 8.04 (d, J=8.6 Hz, 1 H), 7.87 (d, J=12.1 Hz, 1 H), 7.78 (dd, J=8.7, 2.2 Hz, 1 H), 7.62 (s, 1 H), 5.91 (d, J=12.1 Hz, 1 H), 5.32 (s, 1 H), 1.68 (s, 3 H), 1.47 (s, 9 H); MS (m/z) 499.1 (M+H$^+$).

The following compounds were prepared using procedures analogous to those described above using the appropriate alkyne.

| Example | Structure/Name | MS (M + H)$^+$ | NMR | Method |
|---|---|---|---|---|
| 62 | 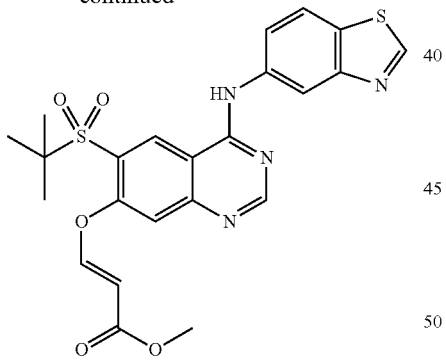<br>(E)-3-((4-(benzo[d]thiazol-5-ylamino)-6-(tert-butylsulfonyl)quinazolin-7-yl)oxy)acrylamide | 484 | $^1$H NMR (400 MHz, DMSO-d6) δ ppm 10.71 (s, 1H), 9.44 (s, 1H), 9.24 (s, 1H), 8.70 (s, 1H), 8.58 (d, J = 1.8 Hz, 1H), 8.19 (d, J = 8.8 Hz, 1H), 7.74-7.95 (m, 1H), 7.61 (s, 1H), 7.01-7.15 (m, 1H), 5.91 (d, J = 11.87 Hz, 1H), 1.24-1.44 (m, 9H) | as Ex. 92 |

-continued

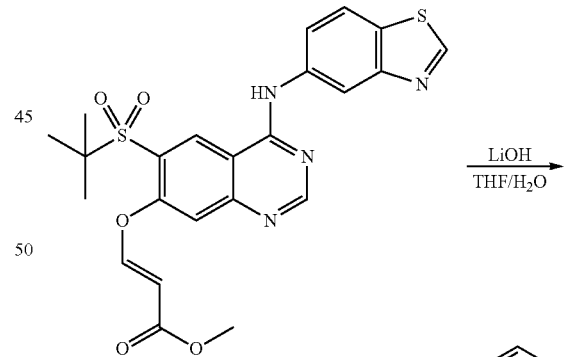

Example 63

(E)-3-((4-(benzo[d]thiazol-5-ylamino)-6-(tert-butylsulfonyl)quinazolin-7-yl)oxy)acrylic acid

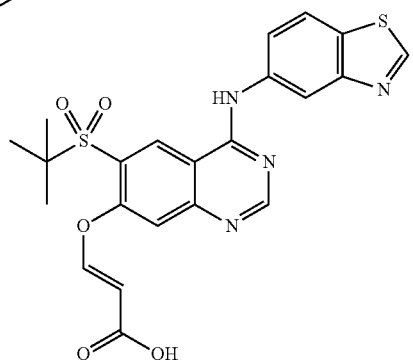

A suspension of (E)-methyl 3-((4-(benzo[d]thiazol-5-ylamino)-6-(tert-butylsulfonyl)quinazolin-7-yl)oxy)acrylate (115 mg, 0.23 mmol) in THF (1.2 mL) and water (1.2 mL) was stirred with LiOH (11 mg, 0.46 mmol) for 2 h at 50° C. Water and 10% citric acid (10 mL) were added and the mixture was extracted with EtOAc and DCM/20% EtOH (2× each). The combined organics were washed with brine and the organics concentrated to dryness. The residue was purified via Gilson reverse phase chromatography (10% to 75% of 0.1% TFA in MeCN in 0.1% TFA in water; Sum 30×150 mm Waters Sunfire column). Pure fractions were partitioned between EtOAc and saturated sodium bicarbonate followed by brine. The organic layer was dried over magnesium sulfate and concentrated in vacuo to provide (E)-3-((4-(benzo[d]thiazol-5-ylamino)-6-(tert-butylsulfonyl)quinazolin-7-yl)oxy)acrylic acid (10.5 mg, 9% yield). $^1$H NMR (400 MHz, DMSO-d$_6$) δ ppm 11.01-11.17 (m, 1 H), 9.45 (s, 1 H), 9.29 (s, 1 H), 8.72-8.84 (m, 1 H), 8.49-8.60 (m, 1 H), 8.24 (d, J=8.6 Hz, 1 H), 7.97 (d, J=12.0 Hz, 1 H), 7.81-7.84 (m, 1 H), 7.68 (s, 1 H), 5.73 (d, J=12.0 Hz, 1 H), 1.37 (s, 9 H); MS (m/z) 484.9 (M+H$^+$).

Example 64

N-(6-(tert-butylsulfonyl)-7-(vinyloxy)quinazolin-4-yl)benzo[d]thiazol-5-amine

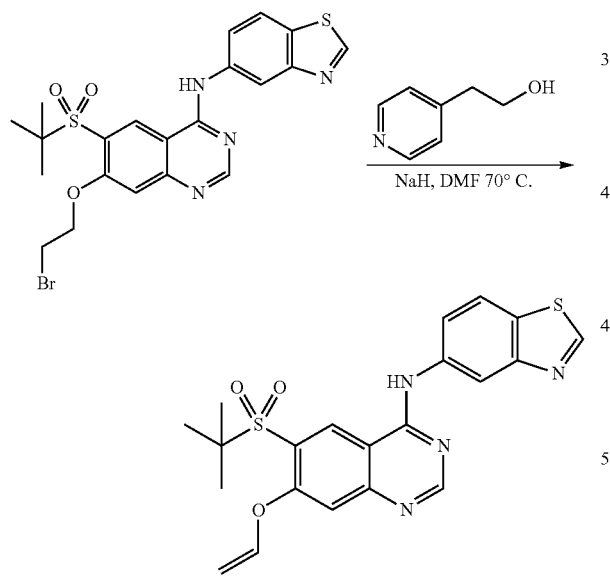

A solution of N-(7-(2-bromoethoxy)-6-(tert-butylsulfonyl)quinazolin-4-yl)benzo[d]thiazol-5-amine (25 mg, 0.05 mmol) and 2-(pyridin-4-yl)ethanol (15 mg, 0.12 mmol) was heated in DMF (939 µl) at 70° C. After 10 minutes, 60% NaH (10 mg, 0.25 mmol) was added and heated 1 min. The residue was filtered, then purified via Gilson reverse phase chromatography (10% to 75% of 0.1% TFA in MeCN in 0.1% TFA in water; Sum 30×100 mm Waters Sunfire column). Pure fractions were partitioned between EtOAc and sat'd sodium bicarbonate, then washed with brine. The organic layer was dried over magnesium sulfate and concentrated in vacuo to provide N-(6-(tert-butylsulfonyl)-7-(vinyloxy)quinazolin-4-yl)benzo[d]thiazol-5-amine (7.5 mg, 36% yield).

$^1$H NMR (400 MHz, DMSO-d$_6$) δ ppm 10.63-10.69 (m, 1 H), 9.43 (s, 1 H), 9.17-9.33 (m, 1 H), 8.65-8.70 (m, 1 H), 8.50-8.63 (m, 1 H), 8.18 (d, J=8.8 Hz, 1 H), 7.89 (d, J=9.1 Hz, 1 H), 7.48 (s, 1 H), 7.17 (dd, J=13.3, 5.8 Hz, 1 H), 5.02 (dd, J=13.3, 2.0 Hz, 1 H), 4.81 (dd, J=5.8, 2.0 Hz, 1 H), 1.37 (s, 9 H); MS (m/z) 441.0 (M+H$^+$).

Example 65

4-(benzo[d]thiazol-5-ylamino)-7-methoxy-N,N-dimethylquinazoline-6-sulfonamide

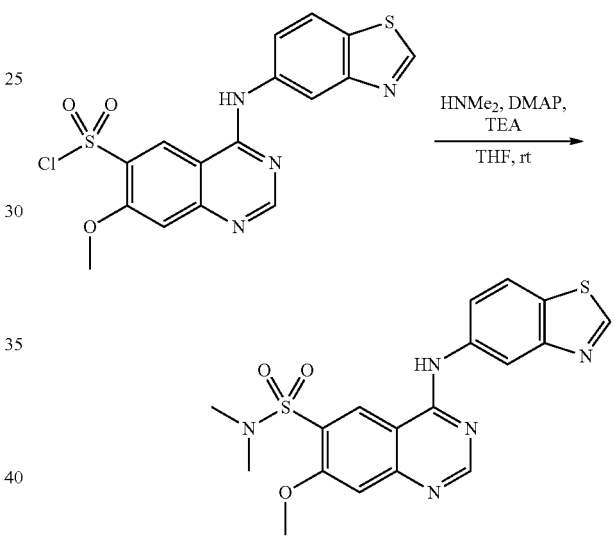

To a vial was added DMAP (3.75 mg, 0.03 mmol) followed by a suspension of 4-(benzo[d]thiazol-5-ylamino)-7-methoxyquinazoline-6-sulfonyl chloride (125 mg, 0.31 mmol) in THF (2 mL), then TEA (0.17 mL, 1.23 mmol), and finally dimethylamine (2.0 M in THF, 0.30 mL). The reaction was stirred at rt overnight. It was then concentrated and the crude material was dissolved in 1:1 DMSO:MeOH and purified by RP HPLC (10->50% MeCN in water with 0.1% TFA) on a 5 µM C18 OBD Sunfire 30×100 mm. Desired fractions were combined, concentrated, and the residue was redissolved in MeOH and treated with MP-carbonate resin. The solution was pipetted off the resin and concentrated to afford the title compound (19 mg, 14%). $^1$H NMR (DMSO-d6) d 11.05 (br. s., 1H), 9.45 (s, 1H), 9.18 (s, 1H), 8.76 (s, 1H), 8.55 (d, J=1.5 Hz, 1H), 8.21 (d, J=8.8 Hz, 1H), 7.85 (dd, J=8.7, 1.9 Hz, 1H), 7.41 (s, 1H), 4.08 (s, 3H), 2.83 (s, 6H); MS (m/z) 416.1 (M+H$^+$).

The following compound was prepared using procedures analogous to those described above using the appropriate amine.

| Example | Structure/Name | MS (M + H)+ | NMR | Method |
|---|---|---|---|---|
| 66 | 4-(benzo[d]thiazol-5-ylamino)-N-isopropyl-7-methoxyquinazolin-6-sulfonamide | 430 | $^1$H NMR (DMSO-d6) δ 11.29 (br. s., 1H), 9.46 (s, 1H), 9.21 (s, 1H), 8.81 (s, 1H), 8.53 (d, J = 1.8 Hz, 1H), 8.23 (d, J = 8.8 Hz, 1H), 7.83 (dd, J = 8.8, 1.8 Hz, 1H), 7.59 (d, J = 7.8 Hz, 1H), 7.39 (s, 1H), 4.10 (s, 3H), 3.28-3.43 (m, 1H), 1.00 (d, J = 6.6 Hz, 6H) | as in Ex. 65 |
| 67 | N-(7-methoxy-6-(pyrrolidin-1-ylsulfonyl)quinazolin-4-yl)benzo[d]thiazol-5-amine | 442 | $^1$H NMR (DMSO-d6) δ 10.97 (br. s., 1H), 9.44 (s, 1H), 9.19 (s, 1H), 8.74 (s, 1H), 8.57 (s, 1H), 8.20 (d, J = 8.8 Hz, 1H), 7.86 (d, J = 8.6 Hz, 1H), 7.40 (s, 1H), 4.09 (s, 3H), 3.33 (t, J = 6.4 Hz, 4H), 1.73-1.86 (m, 4H) | as in Ex. 65 |
| 68 | N-(7-methoxy-6-(morpholinosulfonyl)quinazolin-4-yl)benzo[d]thiazol-5-amine | 458 | $^1$H NMR (DMSO-d6) δ 10.73 (br. s., 1H), 9.43 (s, 1H), 9.14 (s, 1H), 8.70 1H), 8.58 (s, 1H), 8.19 (d, J = 8.6 Hz, 1H), 7.87 (d, J = 8.6 Hz, 1H), 7.40 (s, 1H), 4.07 (s, 3H), 3.58-3.67 (m, 4H), 3.18-3.24 (m, 4H) | as in Ex. 65 |
| 69 | 4-(benzo[d]thiazol-5-ylamino)-N-(2-hydroxyethyl)-7-methoxyquinazolin-6-sulfonamine | 432 | $^1$H NMR (DMSO-d6) δ 11.34 (br. s., 1H), 9.47 (s, 1H), 9.20 (s, 1H), 8.83 (s, 1H), 8.52 (d, J = 2.0 Hz, 1H), 8.24 (d, J = 8.5 Hz, 1H), 7.83 (dd, J = 8.5, 2.0 Hz, 1H), 7.52 (t, J = 5.8 Hz, 1H), 7.41 (s, 1H), 4.09 (s, 3H), 3.38 (t, J = 6.4 Hz, 2H), 2.87-2.97 (m, 2H) | as in Ex. 65 |
| 70 | 4-(benzo[d]thiazol-5-ylamino)-7-methoxy-N-(tetrahydro-2H-pyran-4-yl)quinazolin-6-sulfonamine | 472 | $^1$H NMR (DMSO-d6) δ 11.52 (br. s., 1H), 9.48 (s, 1H), 9.24 (s, 1H), 8.87 (s, 1H), 8.51 (s, 1H), 8.26 (d, J = 8.8 Hz, 1H), 7.87 (d, J = 7.8 Hz, 1H), 7.82 (dd, J = 8.7, 1.4 Hz, 1H), 7.41 (s, 1H), 4.12 (s, 3H), 3.74 (d, J = 11.5 Hz, 2H), 3.27-3.34 (m, 1H), 3.14-3.28 (m, 2H), 1.40-1.60 (m, 4H) | as in Ex. 65 |

| Example | Structure/Name | MS (M + H)+ | NMR | Method |
|---|---|---|---|---|
| 71 | 4-(benzo[d]thiazol-5-ylamino)-N-(2-hydroxy-2-methylpropyl)-7-methoxyquinazoline-6-sulfonamine | 460 | ¹H NMR (DMSO-d6) δ 10.84 (br. s., 1H), 9.44 (s, 1H), 9.14 (s, 1H), 8.72 (s, 1H), 8.59 (s, 1H), 8.19 (d, J = 8.5 Hz, 1H), 7.87 (d, J = 8.5 Hz, 1H), 7.40 (s, 1H), 7.13 (t, J = 6.1 Hz, 1H), 4.08 (s, 3H), 2.72 (d, J = 6.0 Hz, 2H), 1.07 (s, 6H) | as in Ex. 65 |
| 72 | 1-((4-(benzo[d]thiazol-5-ylamino)-7-methoxyquinazolin-6-yl)sulfonyl)pyrrolidin-3-ol | 458 | ¹H NMR (DMSO-d6) δ 10.46 (s, 1H), 9.42 (s, 1H), 9.12 (s, 1H), 8.64 (d, J = 4.3 Hz, 2H), 8.16 (d, J = 8.5 Hz, 1H), 7.91 (d, J = 8.5 Hz, 1H), 7.38 (s, 1H), 5.00 (d, J = 2.8 Hz, 1H), 4.26 (br. s., 1H), 4.04 (s, 3H), 3.46 (dd, J = 8.5, 5.3 Hz, 3H), 3.18 (d, J = 9.5 Hz, 1H), 1.69-1.93 (m, 2H) | as in Ex. 65 |
| 73 | 4-(benzo[d]thiazol-5-ylamino)-N-(2-hydroxypropyl)-7-methoxyquinazoline-6-sulfonamide | 446 | ¹H NMR (DMSO-d6) δ 10.49 (br. s., 1H), 9.42 (s, 1H), 9.10 (s, 1H), 8.64 (d, J = 5.5 Hz, 2H), 8.16 (d, J = 8.8 Hz, 1H), 7.91 (d, J = 8.5 Hz, 1H), 7.38 (s, 1H), 7.27 (t, J = 6.0 Hz, 1H), 4.68 (br. s., 1H), 4.06 (s, 3H), 3.59 (d, 1H), 2.64-2.87 (m, 2H), 1.00 (d, J = 6.3 Hz, 3H), 1.01 (d, J = 6.3 Hz, 3H) | as in Ex. 65 |
| 74 | 4-(benzo[d]thiazol-5-ylamino)-7-methoxy-N-(2-methoxyethyl)quinazolin-6-sulfonamide | 446 | ¹H NMR (DMSO-d6) δ 10.48 (br. s., 1H), 9.42 (s, 1H), 9.09 (s, 1H), 8.64 (br. s., 2H), 8.16 (d, J = 8.8 Hz, 1H), 7.91 (d, J = 8.5 Hz, 1H), 7.47 (t, J = 5.9 Hz, 1H), 7.38 (s, 1H), 4.06 (s, 3H), 3.28 (t, J = 5.8 Hz, 2H), 3.09 (s, 3H), 3.03 (q, 2H) | as in Ex. 65 |

| Example | Structure/Name | MS (M + H)⁺ | NMR | Method |
|---|---|---|---|---|
| 75 | 4-(benzo[d]thiazol-5-ylamino)-7-methoxy-N-(oxetan-3-yl)quinazolin-6-sulfonamide | 444.1 | $^1$H NMR (DMSO-d6) δ 10.60 (br. s., 1H), 9.43 (s, 1H), 9.12 (s, 1H), 8.64 (d, J = 17.8 Hz, 2H), 8.56 (d, J = 7.5 Hz, 1H), 8.17 (d, J = 8.5 Hz, 1H), 7.90 (d, J = 8.5 Hz, 1H), 7.37 (s, 1H), 4.37-4.63 (m, 5H), 4.09 (s, 3H) | as in Ex. 65 |
| 76 | 4-(benzo[d]thiazol-5-ylamino)-N-(2-(dimethylamino)ethyl)-7-methoxyquinazolin-6-sulfonamide | 459 | $^1$H NMR (DMSO-d6) δ 11.30 (br. s., 1H), 10.07 (br. s., 1H), 9.46 (s, 1H), 9.24 (s, 1H), 8.82 (s, 1H), 8.54 (s, 1H), 8.23 (d, J = 8.8 Hz, 1H), 7.92-8.02 (m, 1H), 7.85 (d, J = 8.5 Hz, 1H), 7.46-7.53 (m, 1H), 4.12 (s, 3H), 3.15-3.29 (m, 4H), 2.80 (br. s., 6H) | as in Ex. 65 |
| 77 | 1-((4-(benzo[d]thiazol-5-ylamino)-7-methoxyquinazolin-6-yl)sulfonyl)pyrrolidine-2-carboxylic acid | 486 | $^1$H NMR (DMSO-d6) δ 9.47 (s, 1H), 9.25 (s, 1H), 8.83 (s, 1H), 8.52 (s, 1H), 8.24 (d, J = 8.5 Hz, 1H), 7.95 (d, J = 7.3 Hz, 1H), 7.83 (d, J = 8.8 Hz, 1H), 7.47-7.58 (m, 2H), 4.48 (dd, J = 8.7, 3.1 Hz, 1H), 3.39-3.52 (m, 1H), 3.20-3.33 (m, 1H), 2.10-2.21 (m, 1H), 1.72-2.04 (m, 3H) | as in Ex. 65 |
| 78 | 1-(4-((4-(benzo[d]thiazol-5-ylamino)-7-methoxyquinazolin-6-yl)sulfonyl)piperazin-1-yl)ethanone | 499 | $^1$H NMR (DMSO-d6) δ 11.62 (br. s., 1H), 9.48 (s, 1H), 9.26 (s, 1H), 8.87 (s, 1H), 8.50 (s, 1H), 8.26 (d, J = 8.8 Hz, 1H), 7.95 (d, J = 7.3 Hz, 1H), 7.82 (d, J = 8.5 Hz, 1H), 7.45-7.59 (m, 1H), 4.09 (s, 3H), 3.16-3.31 (m, 4H), 1.99 (s, 3H) | as in Ex. 65 |

| Example | Structure/Name | MS (M + H)+ | NMR | Method |
|---|---|---|---|---|
| 79 | N-(2-(1H-tetrazol-5-yl)ethyl)-4-(benzo[d]thiazol-5-ylamino)-7-methoxyquinazolin-6-sulfonamide | 484 | $^1$H NMR (DMSO-d6) δ 11.38 (br. s., 1H), 9.47 (s, 1H), 9.21 (s, 1H), 8.84 (s, 1H), 8.53 (s, 1H), 8.24 (d, J = 8.5 Hz, 1H), 7.91 (t, J = 5.6 Hz, 1H), 7.84 (d, J = 8.8 Hz, 1H), 7.42 (s, 1H), 4.05 (s, 3H), 3.32 (q, J = 6.7 Hz, 2H), 3.04 (t, 2H) | as in Ex. 65 |
| 80 | 4-(benzo[d]thiazol-5-ylamino)-7-methoxy-N-((tetrahydro-2H-pyran-4-yl)methyl)quinazolin-6-sulfonamide | 486 | $^1$H NMR (DMSO-d6) δ 9.47 (s, 1H), 9.22 (s, 1H), 8.85 (s, 1H), 8.52 (s, 1H), 8.25 (d, J = 8.8 Hz, 1H), 7.95 (d, J = 7.0 Hz, 1H), 7.80-7.86 (m, 1H), 7.74 (t, J = 5.8 Hz, 1H), 7.47 (s, 1H), 4.09 (s, 3H), 3.81 (dd, J = 11.3, 2.8 Hz, 2H), 3.19-3.27 (m, 2H), 2.72 (t, J = 6.3 Hz, 2H), 1.51-1.71 (m, 3H), 1.00-1.16 (m, 2H) | as in Ex. 65 |

Pharmaceutical Compositions

Example A

Tablets are prepared using conventional methods and are formulated as follows:

| Ingredient | Amount per tablet |
|---|---|
| Compound | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
|---|---|
| Compound | 15 mg |
| Dried starch | 178 mg |
| Magnesium stearate | 2 mg |
| Total | 195 mg |

Biological Assay:

A fluorescent polarization based binding assay was developed to quantitate interaction of novel test compounds at the ATP binding pocket of RIPK2, by competition with a fluorescently labeled ATP competitive ligand. Full length FLAG His tagged RIPK2 was purified from a Baculovirus expression system and was used at a final assay concentration of twice the KDapparent. A fluorescent labeled ligand (5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl) benzoic acid, prepared as described in WO2011/120025) was used at a final assay concentration of 5 nM. Both the enzyme and ligand were prepared in solutions in 50 mM HEPES pH7.5, 150 mM NaCl, 10 mM MgCl$_2$, 1 mM DTT, and 1 mM CHAPS. Test compounds were prepared in 100% DMSO and 100 nL was dispensed to individual wells of a multiwell plate. Next, 5 ul RIPK2 was added to the test compounds at twice the final assay concentration, and incubated at rt for 10 min. Following the incubation, 5 ul of the fluorescent labeled ligand solution, was added to each reaction, at twice the final assay concentration, and incubated at rt for at least 10 min. Finally, samples were read on an instrument capable of measuring fluorescent polarization. Test compound inhibition was expressed as percent (%) inhibition of internal assay controls.

For concentration/dose response experiments, normalized data were fit and pIC$_{50s}$ determined using conventional techniques. The pIC$_{50s}$ are averaged to determine a mean value, for a minimum of 2 experiments.

As determined using the above method, the compounds of Examples 1-80 exhibited a pIC$_{50}$ between approximately 5.0 and 9.0. For instance, the compounds of Examples 4 and 16 inhibited RIP2 kinase in the above method with a mean pIC$_{50}$ of approximately 7.5 and 8.5, respectively. The compounds of Examples 4, 6, 16, 21, and 23 inhibited RIP2 kinase in the above method with a mean pIC$_{50}$ in the range of approximately 7.0-9.0.

FLAG his Tagged RIPK2 Preparation:

Full-length human RIPK2 (receptor-interacting serine-threonine kinase 2) cDNA was purchased from Invitrogen (Carlsbad, Calif., USA, Clone ID:IOH6368, RIPK2-pENTR 221). Gateway® LR cloning was used to site-specifically recombine RIPK2 downstream to an N-terminal FLAG-6His contained within the destination vector pDEST8-FLAG-His6 according to the protocol described by Invitrogen. Transfection into *Spodoptera frugiperda*(Sf9) insect cells was performed using Cellfectin® (Invitrogen), according to the manufacturer's protocol.

Sf9 cells were grown in Excell 420 (SAFC Biosciences, Lenexa, Kans., US; Andover, Hampshire UK) growth media at 27° C., 80 rpm in shake flask until of a sufficient volume to inoculate a bioreactor. The cells were grown in a 50 litre working volume bioreactor (Applikon, Foster City, Calif., US; Schiedam, Netherlands) at 27° C., 30% dissolved oxygen and an agitation rate of 60-140 rpm until the required volume was achieved with a cell concentration of approximately 3.7×e6 cells/mL. The insect cells were infected with Baculovirus at a multiplicity of infection (MOI) of 12.7. The cultivation was continued for a 43 hour expression phase. The infected cells were removed from the growth media by centrifugation at 2500 g using a Viafuge (Carr) continuous centrifuge at a flow rate of 80 litres/hour. The cell pellet was immediately frozen and subsequently supplied for purification.

Purification Procedure I: $9.83 \times 10^{10}$ Insect cells were re-suspended in 1.4 L lysis buffer (50 mM Tris (pH 8.0), 150 mM NaCl, 0.5 mM NaF, 0.1% Triton X-100, 1 mL/litre Protease Inhibitor Cocktail Set III (available from EMD Group; CalBiochem/Merck Biosciences, Gibbstown, N.J., US; Damstadt, Germany) and processed by dounce homogenization on ice. The suspension was then clarified by centrifugation at 47,900 g for 2 h, at 4° C. The lysate was decanted from the insoluble pellet and loaded at a linear flow rate of 16 cm/h onto a 55 mL FLAG-M2 affinity column (2.6×10.4 cm) that had been pre-equilibrated with 10 column volumes buffer A (50 mM Tris (pH 8.0), 150 mM NaCl, 0.5 mM NaF, 1 mL/litre Protease Inhibitor Cocktail Set III). The column was then washed with 15 column volumes buffer A, and eluted with 6 column volumes buffer B (buffer A+150 µg/mL 3× FLAG peptide) at a linear flow rate of 57 cm/h. Fractions identified by SDS-PAGE as containing protein of interest were dialyzed to remove the 3× FLAG peptide from the preparation against 5 L of Buffer A (not containing the Protease Inhibitor Cocktail) overnight, using 10 kDa MWCO SnakeSkin Pleated Dialysis Tubing. The purification process yielded 11.3 mg of total protein, with the RIPK2 present at 40% purity by gel densitometry scanning, and identity confirmed by peptide mass fingerprinting. The main contaminating proteins in the preparation were identified as lower molecular weight degraded species of RIPK2.

Purification Procedure II: 100 g cells (10 liter scale fermentation) were frozen, thawed, and re-suspended in 1 L lysis buffer (50 mM Tris HCL pH7.5, 250 mM NaCl, 0.1 mM TCEP, 3 ml Protease inhibitor cocktail) and lysed by high pressure homogenization at 10,000 psi once (Avestin). The suspension was then clarified by centrifugation at 35,000 g for 45 minutes at 4° C. The supernatant was collected by centrifugation and incubated with 5 ml anti-FLAG-M2 resin which was pre-equilibrated with buffer A (50 mM Tris HCL pH7.5, 250 mM NaCl, 0.1 mM TCEP). After protein binding at 4 C degree for 1 hour, the resin was packed into two 25 ml disposable columns. Each column was washed with 25 ml buffer A and eluted with 10 ml (buffer A+200 ug/ml Flag peptide). The elution pool was concentrated to 1 ml and applied to a superdex 200 (16/60) sizing column. Fractions containing full length RIPK2 were collected according to SDS-PAGE analysis results. The purification process yielded 1.36 mg/L 80% pure RIPK2 protein and identity was confirmed by peptide mass fingerprinting.

Biological In Vivo Assay

The efficacy of RIP2 inhibitors may also be evaluated in vivo in rodents. Intraperitoneal (i.p.) or intravenous (i. v.) administration of L18-MDP in mice has been shown to induce an inflammatory response through activation of the NOD2 signaling pathway (Rosenweig, H. L., et al. 2008. Journal of Leukocyte Biology 84:529-536). The level of the inflammatory response in the L18-MDP treated mice/rats is monitored using conventional techniques by measuring increases in cytokine levels (IL8, TNFα, IL6 and IL-1β) in serum and/or peritoneal lavage fluid and by measuring neutrophil influx into the peritoneal space (when L18-MDP is dosed i.p.). Inhibition of the L18-MDP induced inflammatory response in treated rodents may be shown by orally pre-dosing with selected compounds of this invention, then measuring and comparing cytokine levels (IL8, TNFα, IL6 and IL-1β) in serum and/or peritoneal lavage fluid and neutrophil influx into the peritoneal space (when L18-MDP is dosed i.p.) using conventional techniques.

For example, rats were orally pre-dosed with a compound of Example 4, 6, 16, or 21, at a dose of 2 mg/kg or 10 mg/kg (8 rats) and with prednisolone (8 rats, used as a positive control), followed by dosing with L18-MDP (50 µg/rat) 0.25 h/min after pre-dosing. Combined cytokine levels (IL8, TNFα, IL6 and IL-1β) in whole blood samples taken from the rats in this study were measured using an antibody based detection (Meso-Scale Discovery platform). The combined cytokine response was calculated as the averaged response for the 4 cytokines measured relative to the response observed in the vehicle-treated mice, and are depicted in the figures as the mean±standard error of the mean (n=8 rats/group).

REFERENCES

WO2011/011522, WO2009080200, WO2008/33747, WO2008/33749, U.S. Pat. No. 6,046,206, WO96/09294, CA2086968, WO93/07124, EP1199070, CAS Registry No. 1347460-85-8, J. Med. Chem. (2010), 53(3) 2000-2009.

What is claimed is:
1. A compound according to Formula (I):

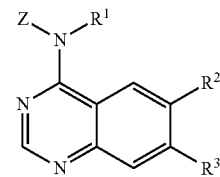

wherein:
$R^1$ is H, —$SO_2(C_1$-$C_4)$alkyl, —$CO(C_1$-$C_4)$alkyl, or ($C_1$-$C_4$)alkyl;
$R^2$ is —$SR^a$, —$SOR^a$, or —$SO_2R^a$, wherein $R^a$ is ($C_1$-$C_6$)alkyl, halo($C_1$-$C_6$)alkyl, ($C_3$-$C_7$)cycloalkyl, 4-7 membered heterocycloalkyl, aryl, or heteroaryl, wherein: said ($C_1$-$C_6$)alkyl is optionally substituted by one or two groups each independently selected from cyano, hydroxyl, ($C_1$-$C_6$)alkoxy, ($C_1$-$C_6$)alkoxy($C_2$-$C_6$)alkoxy, —$CO_2H$, —$CO_2(C_1$-$C_4$)alkyl, —$SO_2(C_1$-$C_4$)alkyl, ($C_3$-$C_7$)cycloalkyl, phenyl, 5-6 membered heteroaryl, 9-10 membered heteroaryl, 4-7 membered heterocycloalkyl and (phenyl)($C_1$-$C_4$ alkyl)amino-, wherein said ($C_3$-$C_7$)cycloalkyl, phenyl, (phenyl)($C_1$-$C_4$ alkyl)amino-, 5-6 membered heteroaryl, 9-10 membered heteroaryl or 4-7 membered heterocycloalkyl is optionally substituted by 1-3 groups each independently selected from halogen, —$CF_3$, hydroxyl, amino, (($C_1$-$C_4$)alkyl)amino-, (($C_1$-$C_4$)alkyl)(($C_1$-$C_4$)alkyl)amino-, ($C_1$-$C_4$)alkyl, phenyl($C_1$-$C_4$)alkyl-, hydroxy($C_1$-$C_4$)alkyl and ($C_1$-$C_4$)alkoxy, said ($C_3$-$C_7$)cycloalkyl or 4-7 membered heterocycloalkyl is optionally substituted by 1-3 groups each independently selected from halogen, —$CF_3$, hydroxyl, amino, (($C_1$-$C_4$)alkyl)amino-, (($C_1$-$C_4$)alkyl)(($C_1$-$C_4$)alkyl)amino-, ($C_1$-$C_4$)alkyl, phenyl($C_1$-$C_4$)alkyl-, hydroxy($C_1$-$C_4$)alkyl-, oxo and ($C_1$-$C_4$)alkoxy, and said aryl or heteroaryl is optionally substituted by 1-3 groups each independently selected from halogen, —$CF_3$, hydroxyl, amino, (($C_1$-$C_4$)alkyl)amino-, (($C_1$-$C_4$)alkyl)(($C_1$-$C_4$)alkyl)amino-, ($C_1$-$C_4$)alkyl, phenyl($C_1$-$C_4$)alkyl-, hydroxy($C_1$-$C_4$)alkyl- and ($C_1$-$C_4$)alkoxy;

$R^3$ is H, halogen, hydroxy, ($C_1$-$C_4$)alkyl-, ($C_2$-$C_4$)alkenyl-, halo($C_1$-$C_4$)alkyl-, ($C_1$-$C_4$)alkoxy-, halo($C_1$-$C_4$)alkoxy-, ($C_1$-$C_4$)alkoxy($C_1$-$C_6$)alkyl-, halo($C_1$-$C_4$)alkoxy($C_1$-$C_6$)alkyl-, ($C_1$-$C_4$)alkoxy($C_2$-$C_6$)alkoxy-, halo($C_1$-$C_4$)alkoxy($C_2$-$C_6$)alkoxy-, hydroxy($C_1$-$C_6$)alkyl-, hydroxy($C_2$-$C_6$)alkoxy-, cyano($C_1$-$C_4$)alkyl-, cyano($C_2$-$C_6$)alkoxy-, carboxy-($C_1$-$C_6$)alkoxy-, ($C_1$-$C_4$)alkoxycarbonyl($C_1$-$C_6$)alkoxy-, ($C_3$-$C_6$)cycloalkyl($C_1$-$C_4$)alkoxy-, ($C_3$-$C_6$)cycloalkoxy-, 4-6 membered-heterocycloalkyl($C_1$-$C_4$)alkoxy-, or 4-6 membered-heterocycloalkoxy-, wherein the halo($C_1$-$C_4$)alkyl-, halo($C_1$-$C_4$)alkoxy-, halo($C_1$-$C_4$)alkoxy($C_1$-$C_6$)alkyl-, or halo($C_1$-$C_4$)alkoxy($C_2$-$C_6$)alkoxy-groups contain 2 or 3 halo atoms; and wherein the ($C_3$-$C_6$)cycloalkyl moiety of the ($C_3$-$C_6$)cycloalkyl($C_1$-$C_4$)alkoxy- or ($C_3$-$C_6$)cycloalkoxy-, is optionally substituted by a group selected from cyano, halo, hydroxyl, ($C_1$-$C_6$)alkoxy and ($C_1$-$C_4$)alkoxy($C_2$-$C_6$)alkoxy;

wherein the 4-6 membered-heterocycloalkyl moiety of the 4-6 membered-heterocycloalkyl($C_1$-$C_4$)alkoxy-, or 4-6 membered-heterocycloalkoxy-, is optionally substituted by a group selected from cyano, halo, hydroxyl, ($C_1$-$C_6$)alkoxy and ($C_1$-$C_4$)alkoxy($C_2$-$C_6$)alkoxy;

Z is pyrazolyl, having the formula:

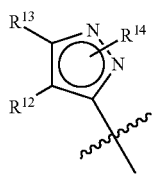

wherein:
$R^{12}$ is H or methyl;
$R^{13}$ is methyl or trifluoromethyl (—$CH_3$ or —$CF_3$);
$R^{14}$ is H or ($C_1$-$C_3$)alkyl; or
$R^{12}$ and $R^{13}$, taken together with the atoms to which they are attached, form a 6 membered carbocyclic ring or heterocyclic ring substituted by $R^{15}$ and $R^{16}$, wherein the heterocyclic ring contains 1 nitrogen atom;
wherein $R^{15}$ and $R^{16}$ are each independently selected from H, halogen, cyano, ($C_1$-$C_4$)alkyl, halo($C_1$-$C_4$)alkyl, ($C_1$-$C_4$)alkoxy, phenoxy, phenyl($C_1$-$C_4$)alkoxy, hydroxyl, hydroxy($C_1$-$C_4$)alkyl-, and aminocarbonyl, wherein the phenyl moiety of said phenoxy or phenyl ($C_1$-$C_4$)alkoxy is optionally substituted by 1-3 substituents each independently selected from halogen, —$CF_3$, ($C_1$-$C_4$)alkyl and ($C_1$-$C_4$)alkoxy;

or a salt thereof.

2. The compound or salt according to claim 1, wherein $R^1$ is H.

3. The compound or salt according to claim 1, wherein $R^2$ is or —$SO_2R^a$.

4. The compound or salt according to claim 1, wherein $R^3$ is H.

5. The compound or salt according to claim 1, wherein $R^{12}$ and $R^{13}$ are both methyl, and $R^{14}$ is H.

6. The compound or salt according to claim 1, wherein $R^{12}$ is H or methyl, $R^{13}$ is methyl or trifluoromethyl, and $R^{14}$ is H or methyl.

7. The compound or salt according to claim 1, wherein Z is 5-(trifluoromethyl)-1H-pyrazol-3-yl, 1,3,4-trimethyl-1H-pyrazol-5-yl, or 4,5-dimethyl-1H-pyrazol-3-yl.

8. The compound or salt according to claim 1, wherein Z is pyrazolyl, substituted by $R^{12}$ and $R^{13}$ wherein:
$R^{12}$ and $R^{13}$ are located on adjacent carbon atoms and taken together with the atoms to which they are attached form a 6 membered carbocyclic ring or heterocyclic ring substituted by $R^{15}$ and $R^{16}$;
wherein $R^{15}$ is H, halogen, cyano, ($C_1$-$C_4$)alkyl, —$CF_3$, ($C_1$-$C_4$)alkoxy, phenoxy, phenyl($C_1$-$C_4$)alkoxy, hydroxyl, hydroxy($C_1$-$C_4$)alkyl-, or aminocarbonyl, wherein the phenyl moiety of said phenoxy or phenyl ($C_1$-$C_4$)alkoxy is optionally substituted by 1-3 substituents each independently selected from the group consisting of halogen, —$CF_3$, ($C_1$-$C_4$)alkyl and ($C_1$-$C_4$)alkoxy; and
$R^{16}$ is H, hydroxyl, halogen, —$CF_3$, hydroxy($C_1$-$C_4$)alkyl, ($C_1$-$C_4$)alkyl or ($C_1$-$C_4$)alkoxy.

9. A compound having the structure of
6-(tert-butylsulfonyl)-N-(5-fluoro-1H-indazol-3-yl)quinazolin-4-amine
N-(5-fluoro-1H-indazol-3-yl)-6-[(1-methylethyl)sulfonyl]-4-quinazolinamine
N-(4,5-dimethyl-1H-pyrazol-3-yl)-6-[(1-methylethyl)sulfonyl]-4-quinazolinamine
6-(tert-butylsulfonyl)-N-(5-(trifluoromethyl)-1H-pyrazol-3-yl)quinazolin-4-amine
6-(tert-butylsulfonyl)-N-(1,3,4-trimethyl-1H-pyrazol-5-yl)quinazolin-4-amine
6-(tert-butylsulfonyl)-7-chloro-N-(4,5-dimethyl-1H-pyrazol-3-yl)quinazolin-4-amine
6-[(1,1-dimethylethyl)sulfonyl]-N-(5-fluoro-1H-pyrazolo[3,4-b]pyridin-3-yl)-7-(methyloxy)-4-quinazolinamine,
6-(tert-butylsulfonyl)-N-(4,5-dimethyl-1H-pyrazol-3-yl)-7-methoxyquinazolin-4-amine,
or a pharmaceutically acceptable salt thereof.

10. The compound, or salt thereof, according to claim 1, wherein the salt is a pharmaceutically acceptable salt of said compound.

11. A pharmaceutical composition comprising the compound or pharmaceutically acceptable salt thereof according to claim 1, and one or more pharmaceutically acceptable excipients.

* * * * *